United States Patent [19]

Tagawa et al.

[11] Patent Number: 5,204,255

[45] Date of Patent: Apr. 20, 1993

[54] HYBRID TISSUE PLASMINOGEN ACTIVATOR/UROKINASE POLYPEPTIDES

[75] Inventors: Michito Tagawa; Masakatsu Wada; Masayuki Yamada; Midori Yokoyama; Naganori Numao, all of Sagamihara, Japan

[73] Assignees: Sagami Chemical Research Center, Tokyo; Central Glass Company, Limited, Ube; Hodogaya Chemical Co., Ltd., Tokyo; Nippon Soda Company, Limited, Tokyo; Nissan Chemical Industries, Limited, Tokyo; Toyo Soda Manufacturing Co., Ltd., Shinnanyo, all of Japan

[21] Appl. No.: 726,129

[22] Filed: Jul. 3, 1991

Related U.S. Application Data

[63] Continuation of Ser. No. 7,865, Jan. 28, 1987, abandoned.

[30] Foreign Application Priority Data

Jan. 31, 1986 [JP] Japan ................................. 61-017734

[51] Int. Cl.$^5$ .......................... C12N 9/48; C12N 9/64; C12N 9/72
[52] U.S. Cl. .................................... 435/215; 435/212; 435/219; 435/226
[58] Field of Search ............... 435/212, 219, 226, 215, 435/172.3

[56] References Cited

U.S. PATENT DOCUMENTS

| 4,752,581 | 6/1988 | Robinson et al. ............... 435/212 X |
| 4,753,879 | 6/1988 | Rosa et al. ....................... 435/212 X |
| 4,992,274 | 2/1991 | Robinson et al. ................ 424/94.63 |

FOREIGN PATENT DOCUMENTS

| 86-53302 | 8/1986 | Australia . | |
| 0093619 | 5/1983 | European Pat. Off. ............ | 435/212 |
| 0151308 | 8/1985 | European Pat. Off. ............ | 435/188 |
| 0155387 | 9/1985 | European Pat. Off. . | |
| 200451 | 11/1986 | European Pat. Off. . | |
| 0213794 | 3/1987 | European Pat. Off. . | |
| 0277313 | 6/1988 | European Pat. Off. . | |
| 0275606 | 7/1988 | European Pat. Off. . | |
| 0271003A | 10/1988 | European Pat. Off. . | |
| 8604351 | 7/1986 | World Int. Prop. O. . | |
| WO8804690 | 6/1988 | World Int. Prop. O. . | |

OTHER PUBLICATIONS

Van Zonneveld, A. et al., International Congress for the Society on Thrombosis & Haemostasis, San Diego, Ca. Abstract 022 from Talk, Jul. 15, 1985.
Van Zonneveld, A., et al., Proc. Natl. Acad. Sci., vol. 83, pp. 4760–4674, Jul. 1986.
Pennica, D. et al., Nature, vol. 301, pp. 214-221, 1983.
N.Y., T. et al., Proc. Natl. Acad. Sci., vol. 81, pp. 5355-5359, 1984.
Holmes, W. et al., Bio/Technology, vol. 3, pp. 923-929, Oct., 1985.
Gheysen, D. et al., J. Biol. Chem., vol. 262, pp. 11779-11784, Aug. 1987.
Pierardi, L. et al., J. Biol. Chem., vol. 262, pp. 11771-11778, Aug., 1987.
Nelles, L. et al., J. Biol. Chem., vol. 262, pp. 5682-5689, Apr., 1987.
Tor Ny, et al., "The Structure of the Human Tissue-Type Plasminogen Activator Gene: Correlation of Intron and Exon Structures to Functional and Structural Domains", Proc. Natl. Acad. Sci., vol. 81, pp. 5355-5359, Sep. 1984.
William E. Holmes, et al., "Cloning and Expression of the Gene for Pro-Urokinase in Escherichia Coli", Biotechnology, vol. 3, pp. 923-929 Oct. 1985.

Primary Examiner—Robert J. Hill, Jr.
Assistant Examiner—Marianne Ponta Allen
Attorney, Agent, or Firm—Wegner, Cantor, Mueller & Player

[57] ABSTRACT

A hybrid plasminogen activator-like polypeptide comprising a polypeptide region responsible for an affinity to fibrin derived from a tissue plasminogen activator polypeptide and a polypeptide region responsible for an enzyme activity derived from a prourokinase polypeptide; a DNA segment coding for the hybrid polypeptide; plasmid containing the DNA segment; a microorganism transformed with the DNA; and a process for production of the hybrid polypeptide comprising culturing the microorganism and recovering the hybrid polypeptide from the cultured cells.

5 Claims, 35 Drawing Sheets

Fig 1-1

```
CCACCGACCCCCACCCCCTGCCTGGAAACTTAAAGGAGGCCGAGCTGTGGGAGCTCAGAGCTGAGATCCTACAGGAGT
1                                                 50 met
CCAGGGCTGGAGAGAAACCTCTGCGAGGAAGGGAAGGAGCAAGCCGTGAATTTAAGGGACGCTGTGAAGCAATCATG
                       100                                            150
```

|   | | | | | | | | | |
|---|---|---|---|---|---|---|---|---|---|
| asp | ala | met | lys | arg | gly | leu | cys | cys | val | leu | leu | cys | gly | ala | val | phe | val | ser |
| GAT | GCA | ATG | AAG | AGA | GGG | CTC | TGT | TGC | GTG | CTG | CTG | TGT | GGA | GCA | GTC | TTC | GTT | TCG |
|     |     |     |     |     |     |     |     |     | 200 |     |     |     |     |     |     |     |     |     |

(6)

| pro | ser | gln | glu | ile | his | ala | arg | phe | arg | arg | gly | ala | arg | SER | TYR | GLN | GLY | CYS | SER |
|---|---|---|---|---|---|---|---|---|---|---|---|---|---|---|---|---|---|---|---|
| CCC | AGC | CAG | GAA | ATC | CAT | GCC | CGA | TTC | AGA | AGA | GGA | GCC | AGA | TCT | TAC | CAA | GGT | TGC | AGC |
|     |     |     |     |     |     |     |     |     |     | 250 |     |     |     |     |     |     |     |     |     |

(26)

| GLU | PRO | ARG | CYS | PHE | ASN | GLY | GLY | THR | CYS | GLN | ALA | LEU | TYR | PHE | SER | ASP | PHE | VAL |
|---|---|---|---|---|---|---|---|---|---|---|---|---|---|---|---|---|---|---|
| GAG | CCA | AGG | TGT | TTC | AAC | GGG | GGC | ACC | TGC | CAG | GCC | CTG | TAC | TTC | TCA | GAT | TTC | GTG |
|     |     |     |     |     |     |     | 300 |     |     |     |     |     |     |     |     |     |     |     |

(46)

| CYS | GLN | CYS | PRO | GLU | GLY | PHE | ALA | GLY | LYS | CYS | GLU | ILE | ASP | THR | ARG | ALA | THR | CYS |
|---|---|---|---|---|---|---|---|---|---|---|---|---|---|---|---|---|---|---|
| TGC | CAG | TGC | CCC | GAA | GGA | TTT | GCT | GGG | AAG | TGC | GAA | ATA | GAT | ACC | AGG | GCC | ACG | TGC |
|     |     |     | 350 |     |     |     |     |     |     |     |     |     |     |     |     |     |     |     |

(66)

| TYR | GLU | ASP | GLN | GLY | ILE | SER | TYR | ARG | GLY | THR | TRP | SER | THR | ALA | GLU | SER | GLY | ALA | GLU |
|---|---|---|---|---|---|---|---|---|---|---|---|---|---|---|---|---|---|---|---|
| TAC | GAG | GAC | CAG | GGC | ATC | AGC | TAC | AGG | GGC | ACG | TGG | AGC | ACA | GCG | GAG | AGT | GGC | GCC | GAG |
| 400 |     |     |     |     |     |     |     |     |     |     |     |     |     |     |     |     | 450 |     |     |

Fig. 1-2

```
CYS THR ASN TRP ASN SER SER ALA LEU ALA GLN LYS PRO TYR SER GLY ARG ARG PRO ASP
TGC ACC AAC TGG AAC AGC AGC GCG TTG GCC CAG AAG CCC TAC AGT GGG CGG AGG CCA GAC    86
                                                        500

ALA ILE ARG LEU GLY LEU GLY ASN HIS ASN TYR CYS ARG ASN PRO ASP ARG ASP SER LYS
GCC ATC AGG CTG GGC CTG GGG AAC CAC AAC TAC TGC AGA AAC CCA GAT CGA GAC TCA AAG   106
                                        550

PRO TRP CYS TYR VAL PHE LYS ALA GLY LYS TYR SER SER GLU PHE CYS SER THR PRO ALA
CCC TGG TGC TAC GTC TTT AAG GCG GGG AAG TAC AGC TCA GAG TTC TGC AGC ACC CCT GCC   126
                                600

CYS SER ASP CYS TYR PHE GLY ASN GLY SER ALA TYR ARG GLY THR HIS
        ⇧
CYS SER GLU GLY ASN SER ASP CYS TYR PHE GLY ASN GLY SER ALA TYR ARG GLY THR HIS
TGC TCT GAG GGA AAT AGT GAC TGC TAC TTT GGG AAT GGG TCA GCC TAC CGT GGC ACG CAC   146
                    650

SER LEU THR GLU SER GLY ALA SER CYS LEU PRO TRP ASN SER MET ILE LEU ILE GLY LYS
AGC CTC ACC GAG TCG GGT GCC TCC TGC CTC CCG TGG AAT TCC ATG ATC CTG ATA GGC AAG   166
700                                             ⇧              750

VAL TYR THR ALA GLN ASN PRO SER ALA GLN ALA LEU GLY LEU GLY LYS HIS ASN TYR CYS
GTT TAC ACA GCA CAG AAC CCC AGT GCC CAG GCA CTG GGC CTG GGC AAA CAT AAT TAC TGC   186
                                            800

ARG ASN PRO ASP GLY ASP ALA LYS PRO TRP CYS HIS VAL LEU LYS ASN ARG ARG LEU THR
CGG AAT CCT GAT GGG GAT GCC AAG CCC TGG TGC CAC GTG CTG AAG AAC CGC AGG CTG ACG   206
                                        850
```

Fig. 1-3

```
TRP GLU TYR CYS ASP VAL PRO SER CYS SER THR CYS GLY LEU ARG GLN TYR SER GLN PRO
TGG GAG TAC TGT GAT GTG CCC TCC TGC TCC ACC TGC GGC CTG AGA CAG TAC AGC CAG CCT     226
                            900                                ⇩

GLN PHE ARG ILE LYS GLY GLY LEU PHE ALA ASP ILE ALA SER HIS PRO TRP GLN ALA ALA
CAG TTT CGC ATC AAA GGA GGG CTC TTC GCC GAC ATC GCC TCC CAC CCC TGG CAG GCT GCC     246
                    950

ILE PHE ALA LYS HIS ARG ARG SER PRO GLY GLU ARG PHE LEU CYS GLY ILE LEU ILE
ATC TTT GCC AAG CAC AGG AGG TCG CCC GGA GAG CGG TTC CTG TGC GGG ATA CTC ATC         266
1000                                                           1050

SER SER CYS TRP ILE LEU SER ALA ALA HIS CYS PHE GLN GLU ARG PHE PRO PRO HIS HIS
AGC TCC TGC TGG ATT CTC TCT GCC GCC CAC TGC TTC CAG GAG AGG TTT CCG CCC CAC CAC     286
                                                    1100

LEU THR VAL ILE LEU GLY ARG THR TYR ARG VAL VAL PRO GLY GLU GLU GLU GLN LYS PHE
CTG ACG GTG ATC TTG GGC AGA ACA TAC CGG GTG GTC CCT GGC GAG GAG GAG CAG AAA TTT     306
                                            1150

GLU VAL GLU LYS TYR ILE VAL HIS LYS GLU PHE ASP ASP ASP THR TYR ASP ASN ASP ILE
GAA GTC GAA AAA TAC ATT GTC CAT AAG GAA TTC GAT GAT GAC ACT TAC GAC AAT GAC ATT     326
                            1200

ALA LEU LEU GLN LEU LYS SER ASP SER SER ARG CYS ALA GLN GLU SER SER VAL VAL ARG
GCG CTG CTG CAG CTG AAA TCG GAT TCC TCC CGC TGT GCC CAG GAG AGC AGC GTG GTC CGC     346
                    1250
```

Fig.1-4

| | | | | | | | | | | |
|---|---|---|---|---|---|---|---|---|---|---|
| THR | VAL | CYS | LEU | PRO | GLU | ASP | LEU | GLN | LEU | PRO | ASP | TRP | THR | GLU | CYS | LEU | SER |
| ACT | GTG | TGC | CTT | CCC | GAG | GAC | CTG | CAG | CTG | CCG | GAC | TGG | ACG | GAG | TGT | CTC | TCC | 366 |
| 1300 | | | | | | | | | | | | | | 1350 | | | |

| GLY | TYR | GLY | LYS | HIS | GLU | ALA | LEU | SER | PRO | PHE | TYR | SER | GLU | ARG | LEU | LYS | GLU | ALA | HIS |
|---|---|---|---|---|---|---|---|---|---|---|---|---|---|---|---|---|---|---|---|
| GGC | TAC | GGC | AAG | CAT | GAG | GCC | TTG | TCT | CCT | TTC | TAT | TCG | GAG | CGG | CTG | AAG | GAG | GCT | CAT | 386 |
| | | | | | | | | | | | | | 1400 | | | | | | |

| VAL | ARG | LEU | TYR | PRO | SER | SER | ARG | CYS | THR | SER | GLN | HIS | LEU | LEU | ASN | ARG | THR | VAL | THR |
|---|---|---|---|---|---|---|---|---|---|---|---|---|---|---|---|---|---|---|---|
| GTC | AGA | CTG | TAC | CCA | TCC | AGC | CGC | TGC | ACA | TCA | CAA | CAT | TTA | CTT | AAC | AGA | ACA | GTC | ACC | 406 |
| | | | | | | | | 1450 | | | | | | | | | | | |

| ASP | ASN | MET | LEU | CYS | ALA | GLY | ASP | SER | GLY | GLY | PRO | LEU | VAL | CYS | LEU | ASN | ASP | GLY | ARG | MET | THR | LEU |
|---|---|---|---|---|---|---|---|---|---|---|---|---|---|---|---|---|---|---|---|---|---|---|
| GAC | AAC | ATG | CTG | TGT | GCT | GGA | GAC | TCG | GGC | GGG | CCC | CTG | GTG | TGT | CTG | AAC | GAT | GGC | CGC | ATG | ACT | TTG | 426 |
| | | | | | | 1500 | | | | | | | | | | | | | | | | |

| ALA | CYS | GLN | GLY | ASP | SER | GLY | GLY | PRO | LEU | VAL | CYS | LEU | ASN | ASP | GLY | ARG | MET | THR | LEU |
|---|---|---|---|---|---|---|---|---|---|---|---|---|---|---|---|---|---|---|---|

(continuing)

| ALA | CYS | GLN | GLY | ASP | SER | GLY | GLY | PRO | LEU | VAL | CYS | GLY | GLN | LYS | ASP | VAL | PRO | GLY | VAL | TYR | THR |
|---|---|---|---|---|---|---|---|---|---|---|---|---|---|---|---|---|---|---|---|---|---|
| GCC | TGC | CAG | GGC | GAT | TCG | GGA | GGC | CCC | CTG | GTG | TGT | GGA | CAG | AAG | GAT | GTC | CCG | GGT | GTG | TAC | ACC | 466 |
| | | | | | 1550 | | | | | | | | | | | | | | 1650 | | |

| LYS | VAL | THR | ASN | TYR | LEU | ASP | TRP | ILE | ARG | ASP | ASN | MET | ARG | PRO | XXX |
|---|---|---|---|---|---|---|---|---|---|---|---|---|---|---|---|
| AAG | GTT | ACC | AAC | TAC | CTA | GAC | TGG | ATT | CGT | GAC | AAC | ATG | CGA | CCG | TGA | CCAGGAACACCCGA |
| 1600 | | | | | | | | | | | | | | 1700 | |

```
CTCCTCAAAAGCAAATGAGATCCCGCCTCTTCTTCAGAAGACACTGCAAAGGCGCAGTGCTTCTCTACAGACTTCTC
                                                                         1800
                   1750
CAGACCCACCACCCGCAGAAGCGGGACGAGACCCTACAGGAGAGGGAAGAGTGCATTTCCCTGATACTTCCCATTTTG
                                       1850
GAAGTTTTCAGGACTTGGTCTGATTTCAGGATACTCTGTCAGATGGGAAGACACATGAATGCACACTAGCCTCTCCAGGAAT
          1900                                                1950
GCCTCCTCCCTGGGCAGAAGTGGCCATGCCACCCTGTTTCGCTAAAGCCCAACCTCCCTGACCTGTCACCGTGAGCAGCT
                              2000
TTGGAAACAGGACCACAAAAATGAAAGCATGTGTCAATAGTAAAGATAACAAGATCTTTCAGGAAAGACGGATTGCATT
        2050                                        2100
AGAAATAGACAGTATATTTATAGTCACAAGAGCCCAGCAGGGCTCAAAGTTGGGGCAGGCTGGCCCGTCATGTTCC
                       2150                                           2200
TCAAAAGCACCCTTGACGTCAAGTCTCCCTTCCCCACTCCCCTGGCTCTCAGAAGGTATTCCTTTTGTGTACAGT
                                     2250
GTGTAAAGTGTAAATCCTTTTCTTTATAAACTTTAGAGTAGCATGAGAGAATTGTATCATTGAACAACTAGGCTTCAG
               2300                                               2350
CATATTTATAGCAATCCATGTTAGTTTTCTGTTGCCACAACCCTGTTTTATACTGTACTTAATAAATTCAGATA
                        2400
TATTTTTCACAGTTTTTCC
       2450
```

Fig. 2-1

```
                                                                              met arg ala    3
CAGGCGCCGGCTCGCCCCTCCTGCCGCCCGTCTAGCGCCCCGACCTCGCCACC                         ATG AGA GCC
1                               50                                             1 leu leu ala arg leu leu leu cys val leu val val ser asp ser lys gly SER ASN GLU    23
CTG CTG GCG CGC CTG CTT CTC TGC GTC CTG GTC AGC GAC TCC AAA GGC AGC AAT GAA
                    100

LEU HIS GLN VAL PRO SER ASN CYS ASP CYS LEU ASN GLY THR CYS VAL SER ASN LYS    43
CTT CAT CAA GTT CCA TCG AAC TGT GAC TGT CTA AAT GGA ACA TGT GTG TCC AAC AAG
                150

TYR PHE SER ASN ILE HIS TRP CYS ASN CYS PRO LYS PHE GLY GLY GLN HIS CYS GLU    63
TAC TTC TCC AAC ATT CAC TGG TGC AAC TGC CCA AAG TTC GGA GGG CAG CAC TGT GAA
        200                                             250

ILE ASP LYS SER LYS THR CYS TYR GLU GLY ASN GLY HIS PHE TYR ARG GLY LYS ALA SER    83
ATA GAT AAG TCA AAG ACC TGC TAT GAG GGG AAT GGT CAC TTT TAC CGA GGA AAG GCC AGC
                                            300

THR ASP THR MET CLY ARG PRO CYS LEU PRO TRP ASN SER ALA THR VAL LEU GLN GLN THR    103
ACT GAC ACC ATG GGC CGG CCC TGC CTG CCC TGG AAC TCT GCC ACT GTC CTT CAG CAA ACG
                                                        350

TYR HIS ALA HIS ARG SER ASP ALA LEU GLN LEU GLY LEU GLY LYS HIS ASN TYR CYS ARG
TAC CAT GCC CAC AGA TCT GAT GCT CTT CAG CTG GGG CTG GGG AAA CAT AAT TAC TGC AGG
                            400
```

Fig. 2-2

```
ASN PRO ASP ASN ARG ARG ARG PRO TRP CYS TYR VAL GLN VAL GLY LEU LYS LEU PRO VAL   123
AAC CCA GAC AAC CGG AGG CGA CCC TGG TGC TAT GTG CAG GTG GGC CTA AAG CCG CTT GTC
                        450                        ⇩

GLN GLU CYS MET VAL HIS ASP CYS ALA ASP GLY LYS LYS PRO SER SER PRO PRO GLU GLU   143
CAA GAG TGC ATG GTG CAT GAC TGC GCA GAT GGA AAA AAG CCC TCC TCT CCA GAA GAA
    500                                                        550

LEU LYS PHE GLN CYS GLY LYS THR LEU ARG PRO ARG PHE LYS ILE ILE GLY GLY GLU       163
TTA AAA TTT CAG TGT GGC AAG ACT CTG AGG CCC CGC TTT AAG ATT ATT GGG GGA GAA
                        ⇩                                  600

PHE THR THR ILE GLU ASN GLN PRO TRP PHE ALA ALA ILE TYR ARG ARG HIS ARG GLY GLY   183
TTC ACC ACC ATC GAG AAC CAG CCC TGG TTT GCG GCC ATC TAC AGG AGG CAC CGG GGC
                                            650

SER VAL THR TYR VAL CYS GLY GLY SER LEU ILE SER PRO CYS TRP VAL ILE SER ALA THR   203
TCT GTC ACC TAC GTG TGT GGA GGC AGC CTC ATC AGC CCT TGC TGG GTG ATC AGC GCC ACA
                                700

HIS CYS PHE ILE ASP TYR PRO LYS LYS GLU ASP TYR ILE VAL TYR LEU GLY ARG SER ARG   223
CAC TGC TTC ATT GAT TAC CCA AAG AAG GAG GAC TAC ATC GTC TAC CTG GGT CGC TCA AGG
                    750

LEU ASN SER ASN THR GLN GLY GLU MET LYS PHE GLU VAL GLU ASN LEU ILE LEU HIS LYS   243
CTT AAC TCC AAC ACG CAA GGG GAG ATG AAG TTT GAG GTG GAA AAC CTC ATC CTA CAC AAG
800                                                                     850
```

Fig. 2-3

| ASP GAC | TYR TAC | SER AGC | ALA GCT | ASP GAC | THR ACG | LEU CTT | ALA GCT | HIS CAC | HIS CAC | ASN AAT | ASP GAC | ILE ATT | ALA GCC | LEU TTG | LEU CTG | LYS AAG | ILE ATC | ARG CGT | SER TCC | 263 |
|---|---|---|---|---|---|---|---|---|---|---|---|---|---|---|---|---|---|---|---|---|
| | | | | | | | | | | | | | | 900 | | | | | | |
| LYS AAG | GLY GGA | ARG AGG | CYS TGT | ALA GCG | GLN CAG | PRO CCA | SER TCC | ARG CGG | THR ACT | ILE ATA | GLN CAG | THR ACC | ILE ATC | CYS TGC | LEU CTG | PRO CCC | SER TCG | MET ATG | | 283 |
| | | | | | | | | | | 950 | | | | | | | | | | |
| TYR TAT | ASN AAC | ASP GAT | PRO CCC | GLN CAG | PHE TTT | GLY GGC | THR ACA | SER AGC | CYS TGT | GLN CAG | ILE ATC | THR ACT | GLY GGA | PHE TTT | LYS AAA | GLU GAG | ASN AAT | SER TCT | | 303 |
| | | | | | | | | | 1000 | | | | | | | | | | | |
| THR ACC | ASP GAC | TYR TAT | LEU CTC | TYR TAT | PRO CCG | GLU GAG | GLN CAG | LEU CTG | LYS AAA | MET ATG | THR ACT | VAL GTT | VAL GTG | LYS AAG | LEU CTG | ILE ATT | SER TCC | HIS CAC | ARG CGG | 323 |
| | | | | | | 1050 | | | | | | | | | | | | | | |
| GLU GAG | CYS TGT | GLN CAG | PRO CCA | HIS CAC | TYR TAC | TYR TAC | GLY GGC | SER TCT | GLU GAA | VAL GTC | THR ACC | THR ACC | LYS AAA | MET ATG | LEU CTG | CYS TGT | ALA GCT | ALA GCT | | 343 |
| 1100 | | | | | | | | | | | | | | | | | | 1150 | | |
| ASP GAC | PRO CCA | GLN CAG | TRP TGG | LYS AAA | THR ACA | ASP GAT | SER TCA | CYS TGC | GLN CAG | GLY GGA | ASP GAC | SER TCA | GLY GGA | GLY GGA | PRO CCC | LEU CTC | VAL GTC | CYS TGT | SER TCC | 363 |
| | | | | | | | | | | | | | | 1200 | | | | | | |
| LEU CTC | GLN CAA | GLY GGC | ARG CGC | MET ATG | THR ACT | LEU TTG | THR ACT | GLY GGA | ILE ATT | VAL GTG | SER AGC | TRP TGG | GLY GGC | ARG CGT | MET ATG | CYS TGT | ALA GCC | LEU CTG | LYS AAG | 383 |
| | | | | | | | | 1250 | | | | | | | | | | | | |

Fig. 2-4

```
                                                                        403
ASP LYS PRO GLY VAL TYR THR ARG VAL SER HIS PHE LEU PRO TRP ILE ARG SER HIS THR
GAC AAG CCA GGC GTC TAC ACG AGA GTC TCA CAC TTC TTA CCC TGG ATC CGC AGT CAC ACC
                    1300

411
LYS GLU ASN GLY LEU ALA LEU XXX
AAG GAA GAG AAT GGC CTG GCC CTC TGA GGGTCCCCAGGGAGGAAACGGGCACCACCCGCTTTCTTGCTGG
                    1350                                                  1400

TTGCTATTTGCAGTAGACTCATCTCCATCAGCTGTAAGAAGAGACTGGGAAGATAGGCTCTGCACAGATGGATTTGCC
                                        1450

TGTGCCCACCACCAGGGCGAACGACAATAGCTTTACCCTCAGGCATAGGCCTGGGTGCTGGCTGCCCAGACCCCTGG
              1500                                          1550

CCAGGAGTGGAGGGGTGGTGTCCTGACTCAACATGTTACTGACCAGCAACTTGTCTTTTTCTGGACTGAAGCCTGCAGGAGT
                            1600

TAAAAAGGGCAGGGCATCTCCTGTGCATGGGCTCGAAGGAGAGCCAGCTCCCCGAGCGGTGGCATTTGTGAGGCCC
        1650                                    1700

ATGGTTGAGAAATGAATAATTCCCAATTAGGAAGTGTAAGCAGCTGAGGTCTCTTGAGGAGCTTAGCCAATGTGGGA
                            1750

GCAGCGGTTTGGGGAGCAGAGACACTAACGACTTCAGGGCAGGGCTCTGATATTCCATGAATGTATCAGGAAATATATA
1800                                                1850

TGTGTGTGTATGTTTGCACACTTGTGTGTGGGCTGTGAGTGTAAGTGTGAGAAAGAGCTGGTGTCTGATTGTTAAGTCT
                1900                                              1950
```

Fig. 2-5

```
AAATATTTCCTTAAACTGTGTGGACTGTGATGCCACACAGAGTGGTCTTTCTGGAGAGGTTATAGGTCACTCCTGGGGC
                                    2000

CTCTTGGGTCCCCCACGTGACAGTGCCTGGGAATGTATTATTCTGCAGCATGACCTGTGACCAGCACTGTCTCAGTTTC
                2050                                              2100

ACTTTCACATAGATGTCCCTTCTTGGCCAGTTATCCCTTCCTTTAGCCTAGTTCATCCAATCCCTCACTGGGTGGGGT
                        2150

GAGGACCACTCCTGTACACTGAATATTTATATTTCACTATTTTATTTATATTTTTGTAATTTTAAATAAAAGTGATCA
        2200                                                  2250

ATAAAATGTGATTTTTCTGATGAAAAA
        2294
```

Fig. 3 (Continue)

| N-Terminal Fibrin-Affinity Region Corresponding to Plasminogen Activator | C-Terminal Fibrinolytic Active Region Corresponding to Urokinase | Symbol of Polypeptide |
|---|---|---|
| 1─Ser ──────── 215 132 135 ─Cys Ala Gln─ | 157 ─Acidic Amino Acid─ 411 ─Pro | HPA 21L |
| 1─Ser ──────── 215 132 135 ─Cys Ala Gln─ | 157 ─Acidic Amino Acid─ 411 ─Pro | HPA 24L |
| 128─Ser ────── 215 132 135 ─Cys Ala Gln─ | 157 ─Acidic Amino Acid─ 411 ─Pro | HPA 11L |
| 128─Ser ────── 215 132 135 ─Cys Ala Gln─ | 157 ─Acidic Amino Acid─ 411 ─Pro | HPA 14L |
| 161─Met ────── 215 132 135 ─Cys Ala Gln─ | 157 ─Acidic Amino Acid─ 411 ─Pro | HPA 01L |
| 161─Met ────── 215 132 135 ─Cys Ala Gln─ | 157 ─Acidic Amino Acid─ 411 ─Pro | HPA 04L |

HYBRID TISSUE PLASMINOGEN ACTIVATOR/UROKINASE POLYPEPTIDES

This application is a continuation of U.S. application Ser. No. 07/007,865 filed Jan. 28, 1987, now abandoned.

BACKGROUND OF THE INVENTION

1. Field of the Invention

The present invention relates to hybrid plasminogen activator-like polypeptides, and a process for production thereof using genetic engineering. The hybrid plasminogen activator-like polypeptides according to the present invention can be used for the prevention and treatment of various kinds of cardiovascular disorders or diseases.

2. Description of the Related Art

Plasminogen activator hydrolyses, in a limited fashion, inactive-type enzyme plasminogen present in plasma, to convert it into active-type enzyme plasmin. The plasmin can hydrolyse fibrin clots generated in a blood vessel and resulting in lysis of thrombus, i.e., fibrinolysis. Since the plasmin is rapidly inactivated in vivo by a plasmin inhibitor present in plasma, a plasminogen activator is clinically used as a thrombolytic agent.

As a plasminogen activator, at present, urokinase isolated from human urine is clinically used. However, urokinase has a disadvantage in that, when administered in a large amount, it can result in systemic hemorrhage. The systemic hemorrhage depends on the ratio of fibrinogen-degradation activity and fibrin-degradation activity of the plasminogen activator. Namely, the systemic hemorrhage depends on the affinity of the plasminogen activator to fibrin. Therefore, attempts have been made to produce urokinase having an affinity to fibrin.

On the other hand, a tissue plasminogen activator has a high affinity to fibrin, and therefore, has been considered as a replacement for urokinase. However, the tissue plasminogen activator has an enzyme activity lower than the urokinase, and is less stable in the blood.

Therefore, there is a demand for a new type of plasminogen activator having a satisfactory affinity to fibrin and a sufficient enzyme activity, as well as a satisfactory stability in vivo.

SUMMARY OF THE INVENTION

The present invention, therefore, provides hybrid plasminogen activator-like polypeptides comprising a polypeptide region responsible for an affinity to fibrin derived from tissue plasminogen activator, and a polypeptide region responsible for enzyme activity derived from prourokinase.

The present invention also provides a gene system used for the production of the above-mentioned polypeptide, including DNA segments coding for the polypeptide, plasmids containing the DNA segment, and microorganisms transformed with the plasmid.

There is also provided a process for the production of the hybrid plasminogen activator-like polypeptide comprising culturing the above-mentioned microorganism, and recovering the polypeptide from the cultured product.

BRIEF DESCRIPTION OF THE DRAWINGS

FIGS. 2-1 to 2-5 represent a nucleotide sequence of a cDNA insert coding for human prourokinase in plasmid pKU22, and a corresponding amino acid sequence in an open reading frame contained in the cDNA insert. In the amino acid sequence, a part of the sequence shown by lower-case letters represents a leader sequence, and a part of the sequence represented by capital letters represents an amino acid sequence of human prourokinase;

FIG. 3 is a schematic illustration of embodiments of the hybrid polypeptide of the present invention;

FIG. 4 is a flow chart showing the construction of plasmids containing a gene coding for human prourokinase;

FIG. 5 is a flow chart showing the construction of plasmids containing a gene coding for a hybrid polypeptide of the present invention;

FIGS. 18-1 to 18-4 represent elution profiles of affinity chromatography showing the fibrin-affinity of various kinds of plasminogen activators;

DESCRIPTION OF THE PREFERRED EMBODIMENT

A. Hybrid plasminogen activator-like polypeptide

The hybrid plasminogen activator-like polypeptide of the present invention comprises a polypeptide region responsible for an affinity to fibrin derived from tissue plasminogen activator and a polypeptide region responsible for enzyme activity derived from prourokinase.

The tissue plasminogen activator is a protein comprising a polypeptide consisting of about 500 amino acids, and including a polypeptide region responsible for the affinity to fibrin at its N-terminal half. The hybrid plasminogen activator-like polypeptide of the present invention includes, as its N-terminal part, a polypeptide region responsible for the affinity to fibrin. This part of the present polypeptide is derived from a native tissue plasminogen activator polypeptide. That is, this part of the present polypeptide may be a whole polypeptide of the native tissue plasminogen activator, or a part thereof responsible for its affinity to fibrin, or a modification thereof. This modification is carried out by the addition of one or same amino acids to the native form, or the deletion of one or some amino acids from the native form, or the replacement of one or some amino acids in the native form, substantially maintaining the fibrin affinity of the native form. When a part of the native tissue plasminogen activator polypeptide is used for the region responsible for the fibrin affinity, the length of that part can differ widely to an extent wherein the fibrin affinity is maintained.

Figure 3:
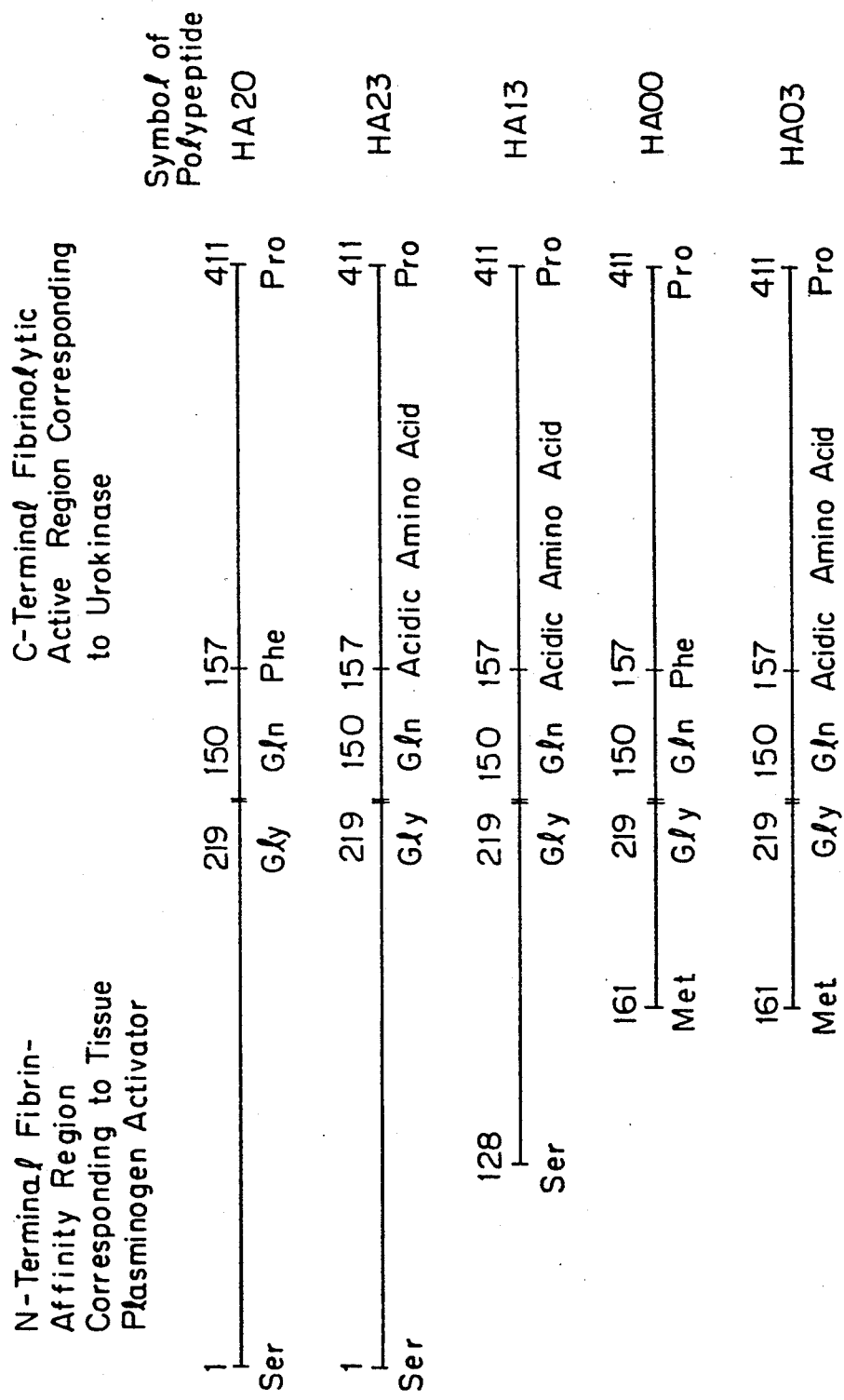
FIGS. 1-1 to 1-5 represent a nucleotide sequence of a cDNA insert coding for human tissue plasminogen activator in plasmid pDPA3, and a corresponding amino acid sequence in an open reading frame contained in the cDNA insert. In the amino acid sequence, a part of the sequence shown by lower-case letters represents a leader sequence, and a part of the sequence shown by capital letters represents an amino acid sequence of the tissue plasminogen activator.
Figure 1:
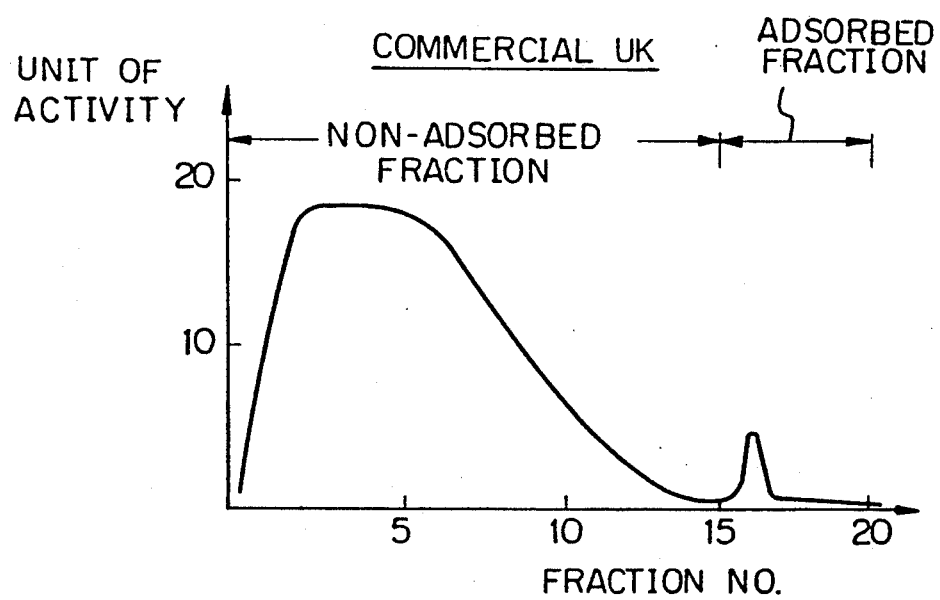
Figure 18:
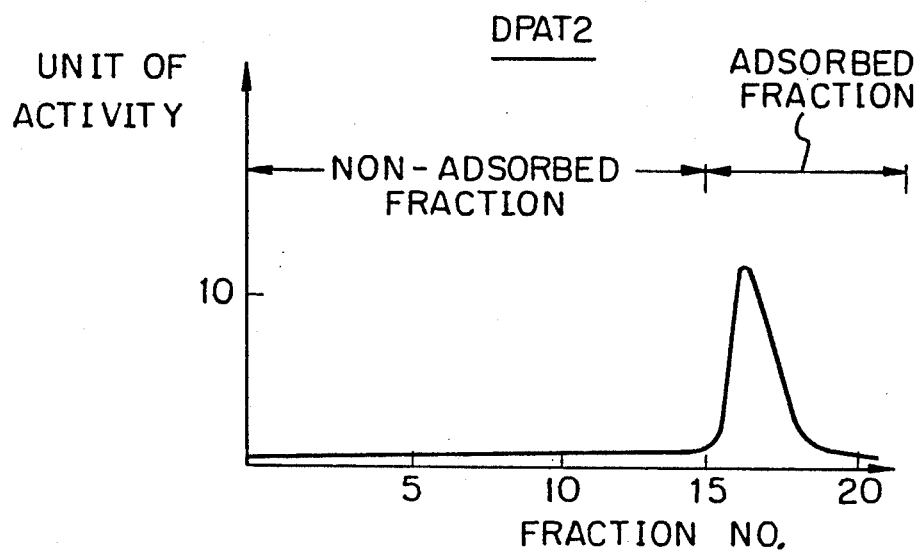
Figure 2:
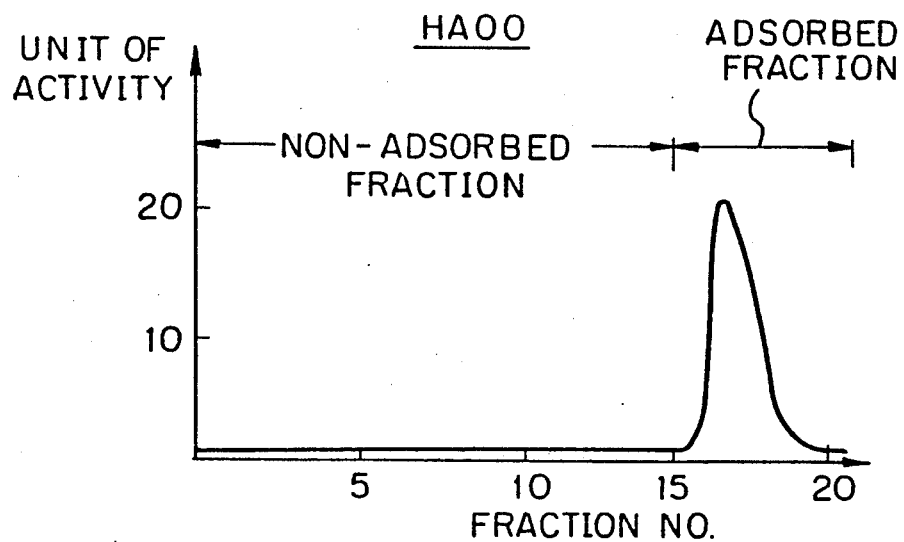
Figure 18:
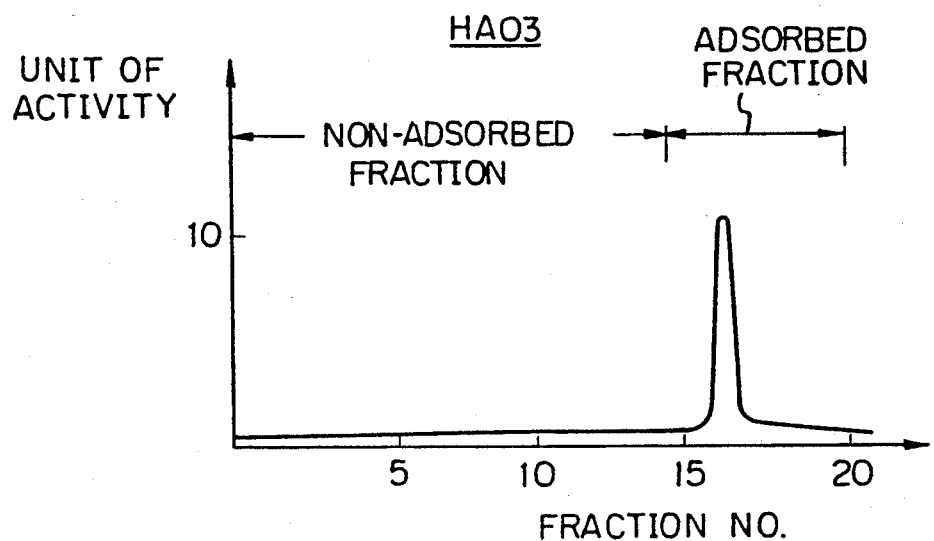
Figure 3:
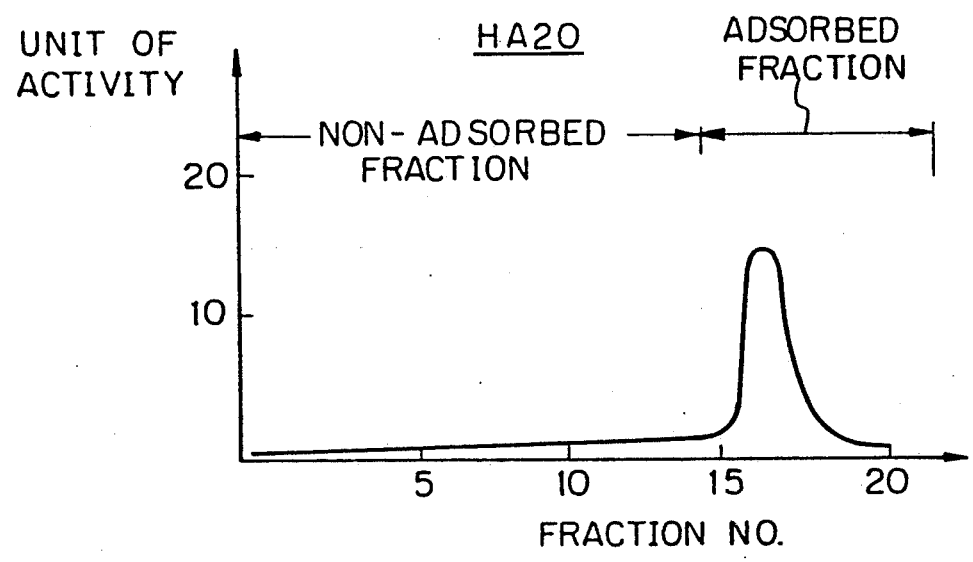
Figures 4, 18:
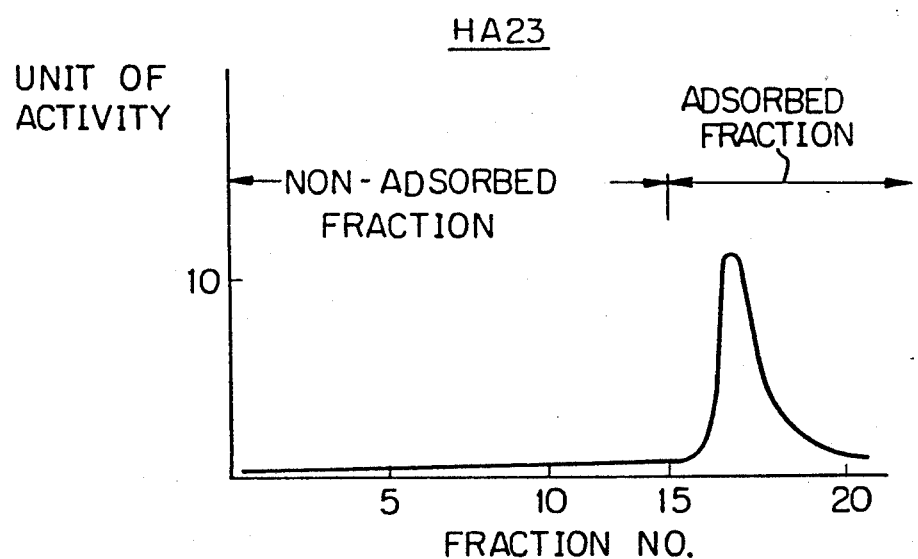

For example, the present inventors prepared hybrid polypeptides which contain, as an N-terminal half, about two kringles consisting of an amino acid sequence from N-terminal first serine to 219th glycine of the human tissue plasminogen activator calculated from the N-terminal serine as shown in FIGS. 1-1 to 1-3; about one kringle consisting of an amino acid sequence from 128th serine to 219th glycine calculated from N-terminal serine as the first amino acid, as shown in FIGS. 1-2 to 1-3; or about a half of a kringle consisting of an amino acid sequence from 161th methionine to 219th glycine calculated from N-terminal serine as the first amino acid, as shown in FIGS. 1-2 to 1-3. These polypeptides were then tested for their affinity to fibrin, and it was confirmed that all of these polypeptides have fibrin affinity. Therefore, the fibrin affinity region of the present hybrid polypeptide can be any polypeptide region of the tissue plasminogen activator containing a region responsible for the fibrin affinity. FIGS. 1-1 to 1-5 represent an nucleotide sequence coding for human tissue plasminogen activator and a corresponding amino acid sequence used as the fibrin affinity region of the present hybrid polypeptide, wherein first serine, 128th serine, 161th methionine, and 219th glycine are shown by arrows.

The prourokinase is a protein comprising a polypeptide consisting of 411 amino acids from N-terminal serine to C-terminal leucine, and including a polypeptide region responsible for enzyme activity at its C-terminal half. The hybrid plasminogen activator-like polypeptides of the present invention includes, as its C-terminal half, a polypeptide region responsible for enzyme activity. This part of the present polypeptide is derived from a prourokinase polypeptide. That is, this part of the present polypeptide may be a whole polypeptide of the native prourokinase or a part thereof responsible for its enzyme activity, or a modification thereof. This modification is carried out by the addition of one or some amino acids to the native form, or the deletion of one or some amino acids from the native form, or the replacement of one or some amino acids in the native form, substantially maintaining the enzyme activity. When, a part of the prourokinase polypeptide is used for the region responsible for the enzyme activity, the length of the part can differ widely to an extent wherein the enzyme activity is maintained.

Figure 4:
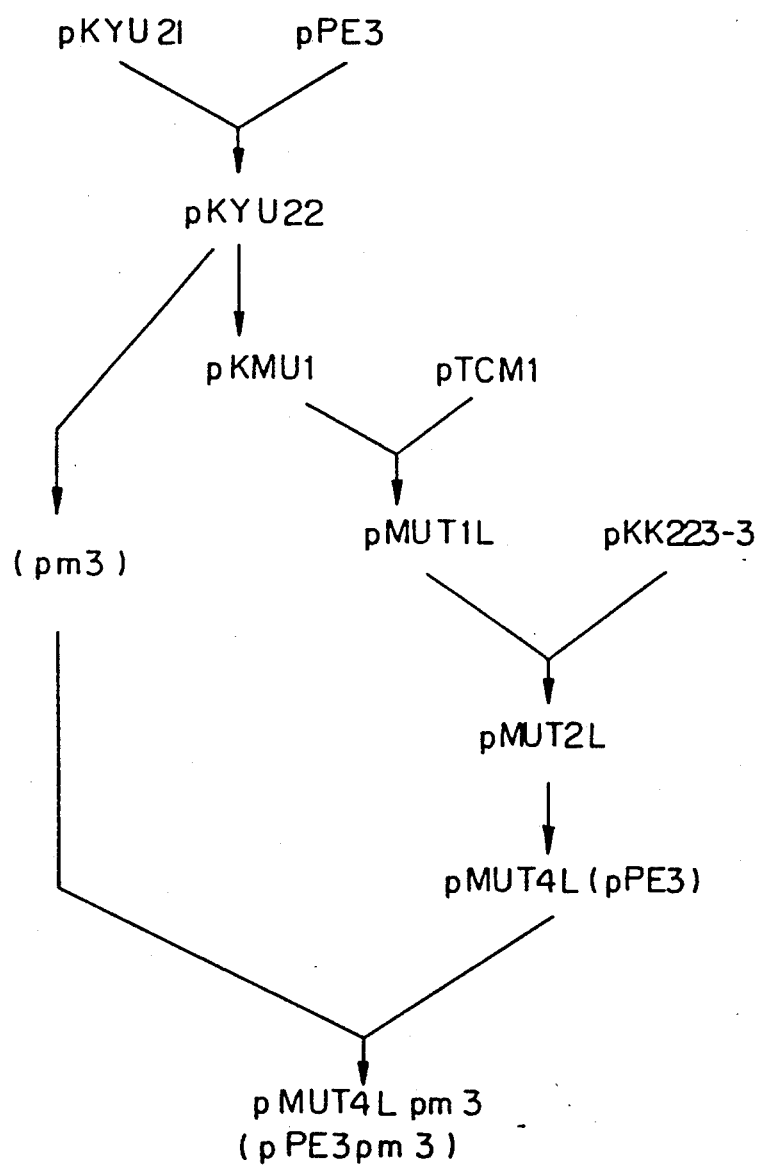
Figure 5:
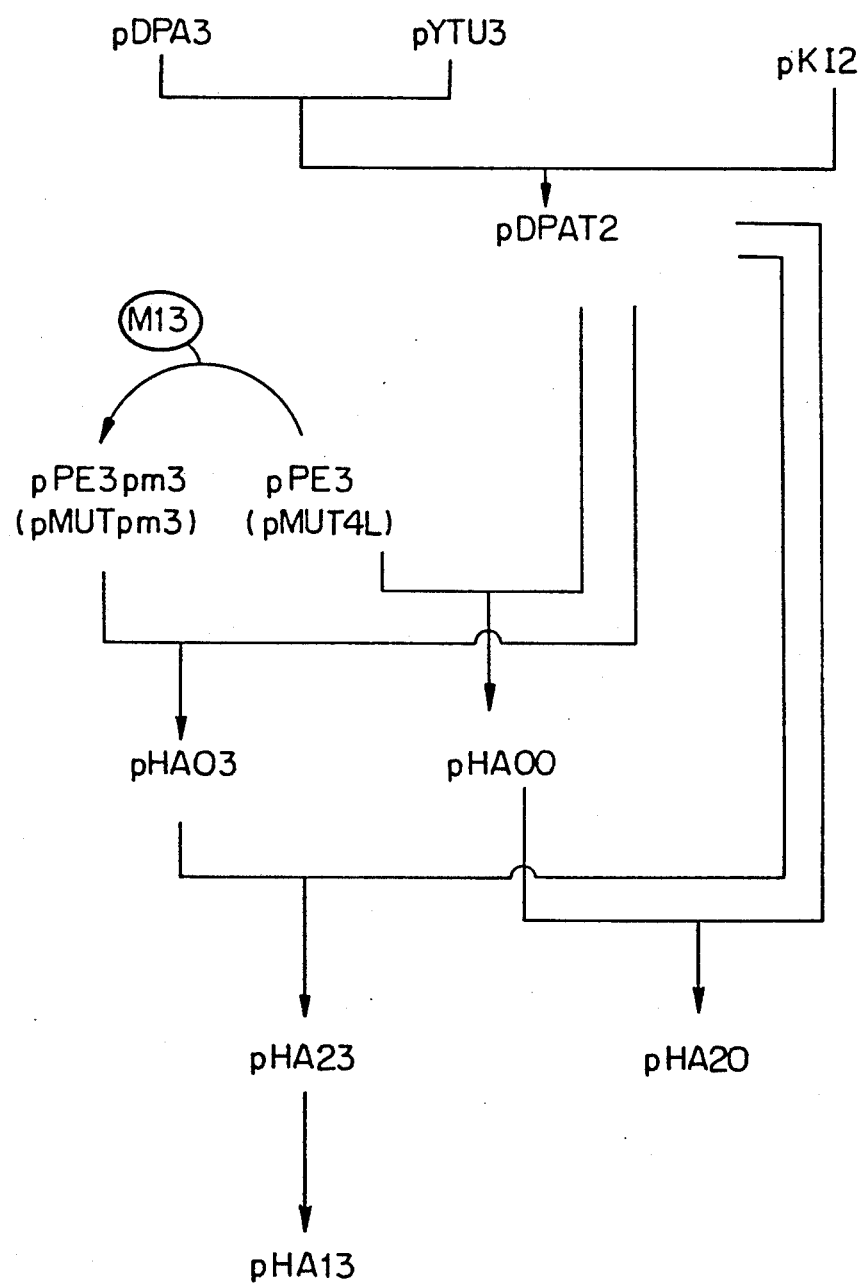

For example, considering the convenience of gene manipulation, the present inventor prepared hybrid polypeptides which contain, as a C-terminal half, an amino acid sequence from 150th glutamine to C-terminal 411th leucine calculated from N-terminal serine as the first amino acid, as shown in FIGS. 2-2 to 2-4, or an amino acid sequence from 132th alanine to C-terminal 411th leucine calculated from N-terminal serine as the first amino acid, as shown in FIGS. 2-2 to 2-4. These hybrid polypeptides were then tested for enzyme activity, and it was confirmed that these polypeptides have enzyme activity.

Prourokinase, which is an inactive form, is activated by cleavage of the polypeptide between 158th lysine and 159th isoleucine to generate active urokinase, and the active urokinase is degraded rather rapidly. Therefore, it is expected that a hybrid plasminogen activator-like polypeptide, which it is difficult to cleave at the above-mentioned position, is sustained in vivo. The present inventor prepared a hybrid plasminogen-like polypeptide wherein 157th phenylalanine shown in FIG. 2-2 is changed to an acidic amino acid such as aspartic acid or glutamic acid, and confirmed that such polypeptides have an enhanced resistance against proteases such as plasmin, thrombin, and trypsin. Therefore, in a preferable embodiment of the present polypeptide, 157th phenylalanine is replaced by an acidic amino acid such as aspartic acid or glutamic acid. FIGS. 2-1 to 2-5 represent an nucleotide sequence coding for human prourokinase and a corresponding amino acid sequence used on the enzyme activity region of the present hybrid polypeptide, wherein 132th alanine, 150th glutamine, and 157th phenylalanine are shown by arrows.

Therefore, in a preferable embodiment, the hybrid plasminogen activator-like polypeptide of the present invention comprises an N-terminal region corresponding to an N-terminal region of human tissue plasminogen activator containing a polypeptide region responsible for its affinity to fibrin and a C-terminal region corresponding to the C-terminal region of human prourokinase containing a polypeptide region responsible for its enzyme activity, wherein 157th phenylalanine shown in FIG. 2-2 is optionally replaced by aspartic acid or glutamic acid. In the prourokinase, a peptide bond between 135th lysine and 136th lysine is susceptible to trypsin-type protease such as plasmin. Therefore, to prevent the cleavage of the peptide band, in a preferable embodiment of the present invention, 135th amino acid lysine is replaced with an amino acid other than basic amino acid. As the amino acid other than basic amino acid, any neutral amino acid or acidic amino acid which does not adversely affect the physiological property of the desired polypeptide may be used and, for example, alanine, asparagine, aspartic acid, glutamine, glutamic acid, phenylalanine, glycine, isoleucine, leucine, methionine, serine, threonine, valine, tryptophan, tyrosine, and proline may be cited. Embodiments of the present hybrid polypeptides are shown in FIG. 3.

B. Gene systems

The present invention also provides gene systems for the production of the above-mentioned hybrid plasminogen activator-like polypeptide, including gene segments coding for the hybrid polypeptides, plasmides containing such gene segments, and microorganisms transformed with such plasmids.

Gene coding for the hybrid polypeptide

The gene codes for the above-mentioned hybrid plasminogen activator-like polypeptide consist of codons which can be expressed in a host microorganism chosen for the gene expression such as *E. coli*. For convenience in the construction of the gene, it is preferably obtained by linking a relevant part of cDNA derived from mRNA coding for human tissue plasminogen activator to a relevant part of cDNA derived from mRNA coding for human prourokinase. FIGS. 1-1 to 1-5 show cDNA coding for human tissue plasminogen activator, together with a corresponding amino acid sequence; and FIGS. 2-1 to 2-5 show cDNA coding for human prourokinase together with a corresponding amino acid sequence.

Plasmid

Although plasmids that function in yeast or animal cells may be used for expression of the hybrid plasminogen activator-like polypeptide of the present invention, the use of a plasmid containing along with said coding region the expression control region necessary for expressing said genes in microorganisms, particularly in *E. coli* and the region necessary for replication in *E. coli* is preferred. As the expression control region any system useful for expressing the foreign gene in *E. coli* may be used arbitrarily. For example, as the promoter/operator systems, tac, $P_L$, lacUV5, $P_R$, trp, and lpp are used. In particular, tac promoter/operator, $P_L$ promoter/operator, and trp promoter/operator are preferred. As an example of SD sequences, the SD sequence of the metapyrocatechase gene (C230SD) (literature 1) and lacSD may be used.

Host Microorganism

Although animal cells and such microorganisms as bacteria and yeast may be used as hosts for introducing said plasmids, the use of bacteria, particularly *E. coli*, is preferred.

As host *E. coli* of the present invention, such strains of nonenterositic, nontoxic *E. coli* as those derived from *E. coli* K-12 may be used, e.g., JM83, JM103, JM105, RB791, SM32, N99, RR1, W3110, and X1776.

Construction of Gene System

An example of the process for constructing genes involved in the present invention comprises the following steps:

(1) preparing a gene coding for a tissue plasminogen activator, and obtaining a DNA fragment coding for a polypeptide region having an affinity to fibrin;

(2) preparing a gene coding for prourokinase, and obtaining a DNA fragment coding for a polypeptide region having enzyme activity; and (3) joining together the DNA fragments obtained in steps (1) and (2) in an appropriate plasmid to construct a gene coding for the hybrid plasminogen activator-like polypeptide.

In the case wherein 157th phenylalanine is replaced by an acidic amino acid such as aspartic acid or glutamic acids, during step (2) a codon coding for the 157th phenylalanine is converted to a codon coding for aspartic acid or glutamic acid.

As an origin of a DNA region coding for a polypeptide region having enzyme activity, plasmid pMUT4L (also designated as pPE3) containing a gene coding for a native human prourokinase, and plasmid pMUT4Lpm3 (also designated as pPE3pm3) containing a gene coding for a stabilized human prourokinase-like polypeptide wherein the 157th amino acid is an acidic amino acid are constructed according to a flow chart shown in FIG. 4. Detailed construction processes for these plasmids are disclosed in reference examples 4 to 15.

As an origin of a DNA region coding for a polypeptide region having the fibrin affinity, plasmid pDPA3 containing a gene coding for a human tissue plasminogen activator is constructed according to processes disclosed in detail in reference examples 1 to 3.

Plasmids containing a gene coding for the hybrid plasminogen activator-like polypeptide of the present invention can be constructed from the above-mentioned plasmids pDPA3, pMUT4L (pPE3) and pMUT4Lpm3 (pPE3pm3), and vector plasmids pYTU3 and pK12.

The plasmid pYTU3 contains $P_L$ promoter and C230 SD sequence, and was constructed according to a procedure described in Japanese Unexamined Patent Publication No. 61-158787; and *E. coli* HB101/pYTU3 containing the plasmid pYTU3 was deposited with the Fermentation Research Institute, Agency of Industrial Science and Technology (1-3, Higashi 1-chome, Yatabe-cho, Tsukuba-gun, Ibaraki-ken, Japan) (F.R.I.), on Dec. 11, 1984, as FERM P-7992. The plasmid pK12 contains tac promoter/operator and C230 SD sequence, and was constructed according to a procedure described in Japanese Unexamined Patent Publication No. 61-158787; and *E. coli* JM103/pK12 containing the plasmid pK12 was deposited with the F.R.I. on December 11, 1984 as FERM P-7996.

Plasmid pDPAT2 constructed in Example 1 contains a gene coding for mature human tissue plasminogen activator under the control by the tac promoter/operator and C230 SD sequence, and can express the mature human tissue plasminogen activator, or is used as an origin of a gene region coding for a polypeptide having the fibrin affinity for the construction of plasmids of the present invention, as described hereinafter. *E. coli* JM103/pDPAT2 containing the plasmid pDPAT2 was deposited with the Deutsche Sammlung von Microorganismen Gesellschaft fur Biotechnologische Forschung mbH (DSM) as an international deposition under the Budapest Treaty on the International Recognition of the Deposit of Microorganisms for the Purpose of Patent Procedure (Budapest Treaty) on Dec. 28, 1985, and has the deposition number DSM 3629.

Plasmid pHA00 constructed in Example 2 contains a gene coding for a hybrid plasminogen activator-like polypeptide (HA00) comprising as its N-terminal half, a polypeptide region from 161th methionine to 219th glycine of a human tissue plasminogen activator calculated from N-terminal serine as the first amino acid, and as its C-terminal half, a polypeptide region from 150th glutamine to 411 C-terminal leucine of human prourokinase calculated from N-terminal serine as the first amino acid, under the control by the tac promoter and C230 SD sequence, and can express the above-mentioned hybrid polypeptide in *E. coli*. *E. coli* JM103/pHA00 containing the plasmid pHA00 was deposited with DSM as DSM3628 on Dec. 28, 1985 under the Budapest Treaty.

Plasmid pH03 constructed in Example 3 contains a gene coding for a hybrid plasminogen activator-like polypeptide comprising as its N-terminal half, a polypeptide region from 161th methionine to 219th glycine of human tissue plasminogen activator calculated from N-terminal serine as the first amino acid, and as its C-terminal half, a polypeptide region from 150th glutamine to 411th N-terminal leucine of human prourokinase calculated from N-terminal serine as the first amino acid wherein 157th phenylalanine is replaced by aspartic acid, under the control by the tac promoter/operator and C230 SD sequence, and can express the above-mentioned hybrid polypeptide in *E. coli*. *E. coli* JM103/pHA03 containing the plasmid pHA03 was deposited with DSM as DSM3627 on December 28, 1985 under the Budapest Treaty.

Plasmid pHA20 constructed in Example 4 contains a gene coding for a hybrid plasminogen activator-like polypeptide (HA20) comprising as its N-terminal half, a polypeptide region from N-terminal serine at amino acid position 1 to 219th glycine of human tissue plasminogen activator, and as its C-terminal half, a polypeptide region from 150th glutamine to 411th C-terminal leucine of human prourokinase calculated from N-terminal serine as the first amino acid, under the control by the tac promoter/operator and C230 SD sequence, and can express the above-mentioned hybrid polypeptide in *E. coli*. *E. coli* JM103/pHA20 containing the plasmid pHA20 was deposited with DSM as DSM3626 on December 28, 1985 under the Budapest Treaty.

Plasmid pHA23 constructed in Example 5 contains a gene coding for a hybrid plasminogen activator-like polypeptide (HA23) comprising as its N-terminal half, a polypeptide region from N-terminal serine at amino acid position 1 to 219th glycine of human tissue plasminogen activator, and as its C-terminal half, a polypeptide region from 150th glutamine to 411th C-terminal leucine of human prourokinase calculated from N-terminal serine as the first amino acid wherein 157th phenylalanine is replaced by aspartic acid, under the control by the tac promoter and C230 SD sequence, and can express the above-mentioned hybrid polypeptide in *E. coli*. *E. coli* JM103/pHA23 containing the plasmid pHA23 was deposited with DSM as DSM3625 on Dec. 28, 1985 under the Budapest Treaty.

Plasmid pHA13 constructed in Example 6 contains a gene coding for a hybrid plasminogen activator-like polypeptide comprising as its N-terminal half, a polypeptide region from 128th serine to 219th glycine of human tissue plasminogen activator calculated from N-terminal serine as the first amino acid, and as its C-terminal half, a polypeptide region from 150th glutamine to 411th C-terminal leucine of human prourokinase calculated from N-terminal serine on the first amino acid wherein 157th phenylalanine is replaced by aspartic acid, under the control by the tac promoter/operator and C230 SD sequence, and can express the above-mentioned hybrid polypeptide.

Plasmid pHA21L constructed in Example 11 contains a gene coding for a hybrid plasminogen activator-like polypeptide (HPA21L) comprising as its N-terminal half, a polypeptide region from N-terminal serine at amino acid position 1 to 215th cysteine of human tissue plasminogen activator calculated from N-terminal serine as the first amino acid, and as its C-terminal half, a polypeptide region from 132th alanine to 411th N-terminal leucine of human prourokinase calculated from N-terminal serine as the first amino acid wherein 135th lysine is replaced by glutamine, under the control by the tac promoter/operator and C230 SD sequence, and can express the above-mentioned hybrid polypeptide in *E. coli*. *E. coli* JM103/pHA21L containing the plasmid pHA21L was deposited with DSM as DSM3951 on Jan. 6, 1987 under the Budapest Treaty.

Plasmid pHA24L constructed in Example 12 contains a gene coding for a hybrid plasminogen activator-like polypeptide (HPA24L) comprising as its N-terminal half, a polypeptide region from N-terminal serine at amino acid position 1 to 215th cysteine of human tissue plasminogen activator, and as its C-terminal half, a polypeptide region from 132th alanine to 411th C-terminal leucine of human prourokinase calculated from N-terminal serine as the first amino acid, under the control by the tac promoter/operator and C230 SD sequence wherein 135th lysine is replaced by glutamine and 157th phenylalanine is replaced by aspartic acid, and can express the above-mentioned hybrid polypeptide in *E. coli*. *E. coli* JM103/pHA24L containing the plasmid pHL24L was deposited with DSM as DSM3952 on Jan. 6, 1987 under the Budapest Treaty.

Plasmid pHA11L constructed in Example 13 contains a gene coding for a hybrid plasminogen activator-like polypeptide (HPA11L) comprising as its N-terminal half, a polypeptide region from 128th serine to 215th cysteine of human tissue plasminogen activator, and as its C-terminal half, a polypeptide region from 132th alanine to 411th C-terminal leucine of human prourokinase calculated from N-terminal serine as the first amino acid wherein 135th lysine is replaced by glutamine, under the control by the tac promoter and C230 SD sequence, and can express the above-mentioned hybrid polypeptide in *E. coli*.

Plasmid pHA14L constructed in Example 14 contains a gene coding for a hybrid plasminogen activator-like polypeptide (HPA14L) comprising as its N-terminal half, a polypeptide region from 128th serine to 215th cysteine of human tissue plasminogen activator calculated from N-terminal serine as the first amino acid, and as its C-terminal half, a polypeptide region from 132th alanine to 411th C-terminal leucine of human prourokinase calculated from N-terminal serine as the first amino acid wherein 135th lysine is replased by glutamine and 157th phenylalanine is replaced by aspartic acid, under the control by the tac promoter/operator and C230 SD sequence, and can express the above-mentioned hybrid polypeptide.

Plasmid pHA01L constructed in Example 15 contains a gene coding for a hybrid plasminogen activator-like polypeptide (HPA01L) comprising as its N-terminal half, a polypeptide region from 161th methionine to 215th cysteine of human tissue plasminogen activator calculated from N-terminal serine as the first amino acid, and as its C-terminal half, a polypeptide region from 132th alanine to 411th N-terminal leucine of human prourokinase calculated from N-terminal serine as the first amino acid wherein 135th lysine is replaced by glutamine, under the control by the tac promoter/operator and C230 SD sequence, and can express the above-mentioned hybrid polypeptide in E. coli.

Plasmid pHA04L constructed in Example 16 contains a gene coding for a hybrid plasminogen activator-like polypeptide (HPA04L) comprising as its N-terminal half, a polypeptide region from 161th methionine to 215th cysteine of human tissue plasminogen activator calculated from N-terminal serine as the first amino acid, and as its C-terminal half, a polypeptide region from 132th alanine to 411th N-terminal leucine of human prourokinase calculated from N-terminal serine as the first amino acid wherein 135th lysine is replaced by glutamine and 157th phenylalanine is replaced by aspartic acid, under the control by the tac promoter/operator and C230 SD sequence, and can express the above-mentioned hybrid polypeptide in E. coli.

D. Expression of gene and purification of hybrid polypeptides

E. coli transformed with the above-mentioned cultured, for example, in L-medium supplemented with 100 μg/ml of ampicillin, and when the cell concentration reaches an absorbance of 0.3 to 0.6 at 550 mm, an inducer isopropyl-$\beta$-D-thiogalactopyranoside is added to the medium as 1 mM inducer, and culturing is carried out for an additional several hours to accumulate the hybrid polypeptide in the cultured cells.

To recover and purify the target hybrid polypeptide, any conventional procedure used for recovery and purification of a polypeptide accumulated in cells may be used. For example, cultured cells are collected, and the collected cells are disrupted by any conventional means, and the disrupted cells are centrifuged to collect a precipitate. The target polypeptide is recovered in the precipitate. Next, the precipitate is treated with guanidine hydrochloride to dissolve the target polypeptide. The target polypeptide is then purified by an appropriate combination of conventional procedures for the purification of protein, such as liquid chromatography, ion exchange chromatography, affinity chromatography and the like. An embodiment of recovery and purification of the hybrid polypeptide of the present invention is described in Example 7.

E. Property of hybrid polypeptide (1) Analysis by electrophoresis

Samples of the expression products prepared as above-mentioned are subjected to an SDS-polyacrylamide gel electrophoresis, and the gel is stained with Coomassic Blue. An example of the result is shown in FIG. 17A. In FIG. 17A, lanes 1, 2, and 3 represent the results of expression products obtained from E. coli JM103/pPE3, E. coli JM103/pHA03, and E. coli JM101/pDPAT2, respectively.

(2) Immunological confirmation

Figure 17:
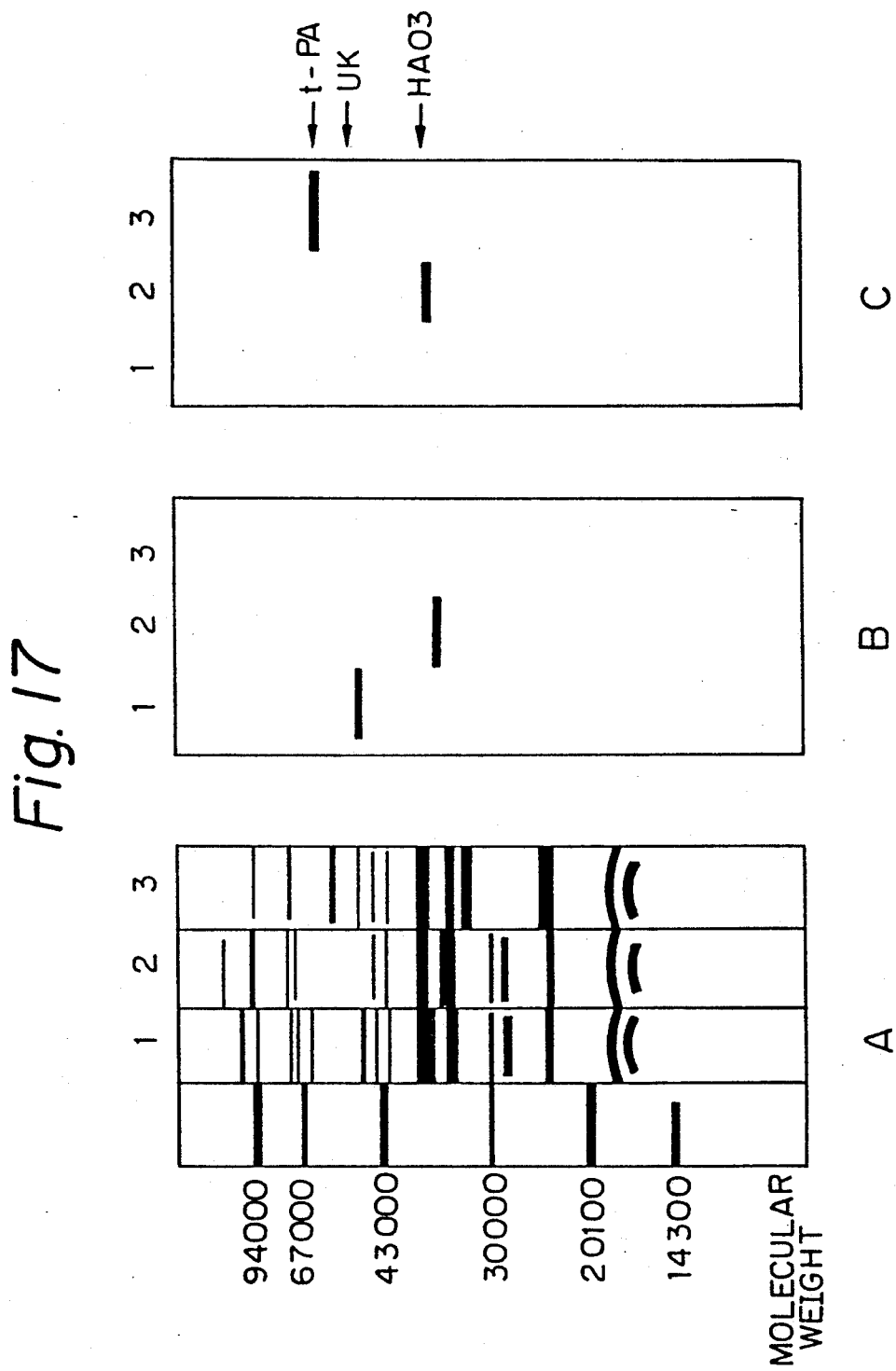
FIG. 17 represents a result of electrophoresis wherein an expression product from *Escherichia coli* JM103/pHA03 (lane 2) is compared with an expression product from *E. coli* JM103/pPE3 (pMUT4L) producing native human prourokinase (UK) (lane 1), and an expression product from *E. coli* JM103/pDPAT2 producing native human tissue plasminogen activator (t-PA) (lane 3). In this figure, A represents a composition of proteins stained by Coomassie Blue; B represents products reactive with an anti-urokinase antibody developed by a enzyme stain method; and C represents products reactive with an anti-tissue plasminogen activator antibody developed by a enzyme stain method.

Next, the reactivity of the products separated by the above-mentioned electrophoresis with an anti-tissue plasminogen activator antiserum or with an anti-urokinase antiserum was tested on a nitrocellulose sheet, and the reaction patterns shown in FIG. 17 B and C were obtained. As seen from the figures, it was confirmed that the hybrid polypeptide HA03 of the present invention is reactive with both the above-mentioned antisera.

For other hybrid polypeptides, similar results were obtained.

(3) Affinity to fibrin

Figure 18:
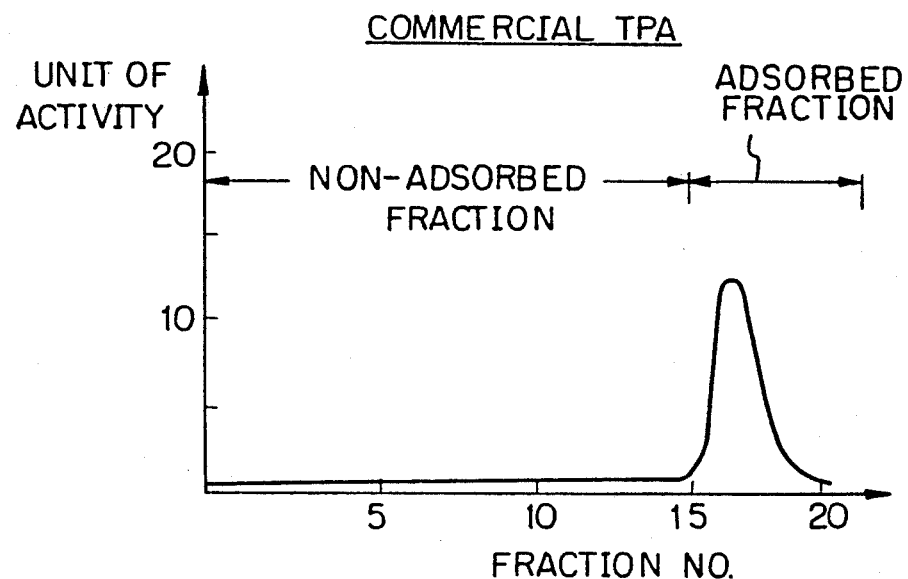

Fibrin affinity columns were prepared, and the sample of the expression product applied to the column, and elution was carried out first with Tris-HCl buffer (A) and then with Tris-HCl buffer containing 2M KSCN(B). The elute was fractionated, and fractions eluted with (A) designated as non-adsorbed fractions; and fractions eluted with (B) designated as adsorbed fractions. Each fraction thus obtained was tested for plasminogen activating action on a fibrin plate containing plasminogen. The results are shown in FIGS. 18-1 to 18-4. As seen from these figures, while a commercially available urokinase (UK) was eluted in non-adsorbed fractions, hybrid polypeptides of the present invention and a commercially available tissue plasminogen activator (TPA) were eluted in adsorbed fractions. Therefore, it is evident that the hybrid polypeptide of the present invention have the same level of fibrin affinity as that of native tissue plasminogen activator.

(4) Measurement of Km value on synthetic substrate S-2288

To confirm enzyme activity of the present hybrid polypeptide, Km values of an expression product HA03 from plasmid pHA03 and an expression product HA20 from plasmid pHA20 after activation with plasmin, which are representatives of hybrid polypeptides containing as its fibrin affinity region about two kringles or about a half kringle of polypeptide, and as its enzyme activity region, an enzyme activity region of native human prourokinase or a corresponding region wherein 157th phenylalanine is replaced by aspartic acid, were compared with the Km value of a commercially available urokinase. The Km values of three polypeptides were the same, $2.0 \times 10^{-4}$ mol/l. Therefore, it was confirmed that the hybrid polypeptides of the present invention, after activation, exhibit the same level of enzyme activity as that of native urokinase.

(5) Stability against plasmin and thrombin

Among the hybrid polypeptides of the present invention, those wherein 157th phenylalanine is replaced by aspartic acid, i.e., hybrid polypeptide HA03, HA13, and HA23, are difficult to inactivate by thrombin, and are activated by plasmin at a lower speed.

As seen from the above description, the hybrid plasminogen activator-like polypeptides of the present invention exhibit a fibrin affinity at the same level as a tissue plasminogen activator, and when activated, exhibit an enzyme activity at the same level as urokinase. Moreover, the hybrid plasminogen activator-like polypeptides wherein 157th phenylalanine is replaced by an acidic amino acid are stable against plasmin, thrombin and other proteases, and therefore, when administered in vivo, are expected to exhibit a sustained fibrinolytic activity.

At present, plasminogen activators having such properties have not been known, and the present plasminogen activator-like polypeptides are a new type.

EXAMPLES

The present invention will now be further illustrated by, but is by no means limited to, the following Reference examples and Examples.

REFERENCE EXAMPLE 1. ISOLATION OF POLY A+RNA

Cells of human pharyngeal cancer cell line Detroit 562 were grown in a modified Eagle's medium supplemented with 10% fetal calf serum, 0.1 mM nonessential amino acids, 1 mM sodium pyruvate, and 0.1% lactalbumin on a plastic plate under the presence of carbon dioxide at a concentration of 5%. When a confluent state was reached, the medium was removed, and 2 ml each of a denatured solution (6 M guanidinium thiocyanate, 5 mM sodium citrate, 0.5% sarcosine, and 0.1 M 2-mercaptoethanol) was added to the plastic plate 9 cm in diameter to denature a cellular material to obtain an extract. According to a method of Chirgwin et al (literature 2), the extract thus obtained was overlaid on a 5.7 M CsCl solution, and the whole was centrifuged to isolate RNA. Typically, 12 mg of RNA was recovered from 60 plastic plates.

Next, poly A+RNA was isolated by oligo dT cellulose chromatography (literature 3). Finally, about 600 μg of an RNA preparation was obtained.

REFERENCE EXAMPLE 2. PREPARATION OF cDNA LIBRARY

According to a method of Okayama and Berg (literature 4), cDNA was synthesized. That is, 2 μg of a vector primer and 3 μg of the above-mentioned poly A+RNA were mixed, and cDNA extention reaction was carried out at 37° C. for 40 minutes using 12 units of reverse transcriptase. Subsequently, according to the literature, the addition of oligo dC, digestion with Hind III, annealing and cyclization with a linker DNA, and replacement of RNA chain were carried out. The final reaction mixture thus prepared was stored as a cDNA library at −20° C. This preparation can be thawed immediately before use for transformation of E. coli. Typically, about 100,000 transformants were obtained using E. coli χ1776 as competent cells, from the above-mentioned reaction mixture.

REFERENCE EXAMPLE 3. SCREENING

To isolate clones which contain plasmid carrying a gene coding for a plasminogen activator-like protein from the above-mentioned transformants, synthetic DNA fragments were used as a probe. The DNA fragments have the following nucleotide sequences:

Probe I
5'                                3'
  AATCGGGCATGGATTTCCTG , and

Probe II
5'                          3'
  GCCCCCGCACAGGAACCG.

These nucleotide sequences are complementary to partial sequences of cDNA coding for a melanoma plasminogen activator reported by Pennica (literature 6) (Probe I: nucleotide number 154-173; Probe II: nucleotide number 1099-1116 in the literature).

These fragments were labeled with $^{32}$P-γ-ATP at their 5'-end. The labeled probes were hybridized with the transformant E. coli grown on a nitrocellulose filter and denatured with an alkali, on the filter in a hybridization buffer of 900 mM NaCl, 90 mM sodium citrate, 10 ×Denhart's solution (literature 7), at 45° C., for 20 hours. Next, the nitrocellulose filter was washed in a solution of 300 mM NaCl and 30 mM sodium citrate, and the filter was placed in contact with an X-ray film to obtain an autoradiogram, and hybridization-positive clones were detected. By using a mixture of the probes I and II, from about 50,000 clones more than ten hybridization-positive clones were isolated. Among these hybridization positive clones, one clone E. coli χ1776 (pDPA3) was hybridized with both probes. From this clone, plasmid pDPA3 was obtained according to a conventional procedure.

E. coli χ1776 (pDPA3) containing the plasmid pDPA3 was deposited with F.R.I. on November 8, 1984 as FERM P-7931.

Figure 13:
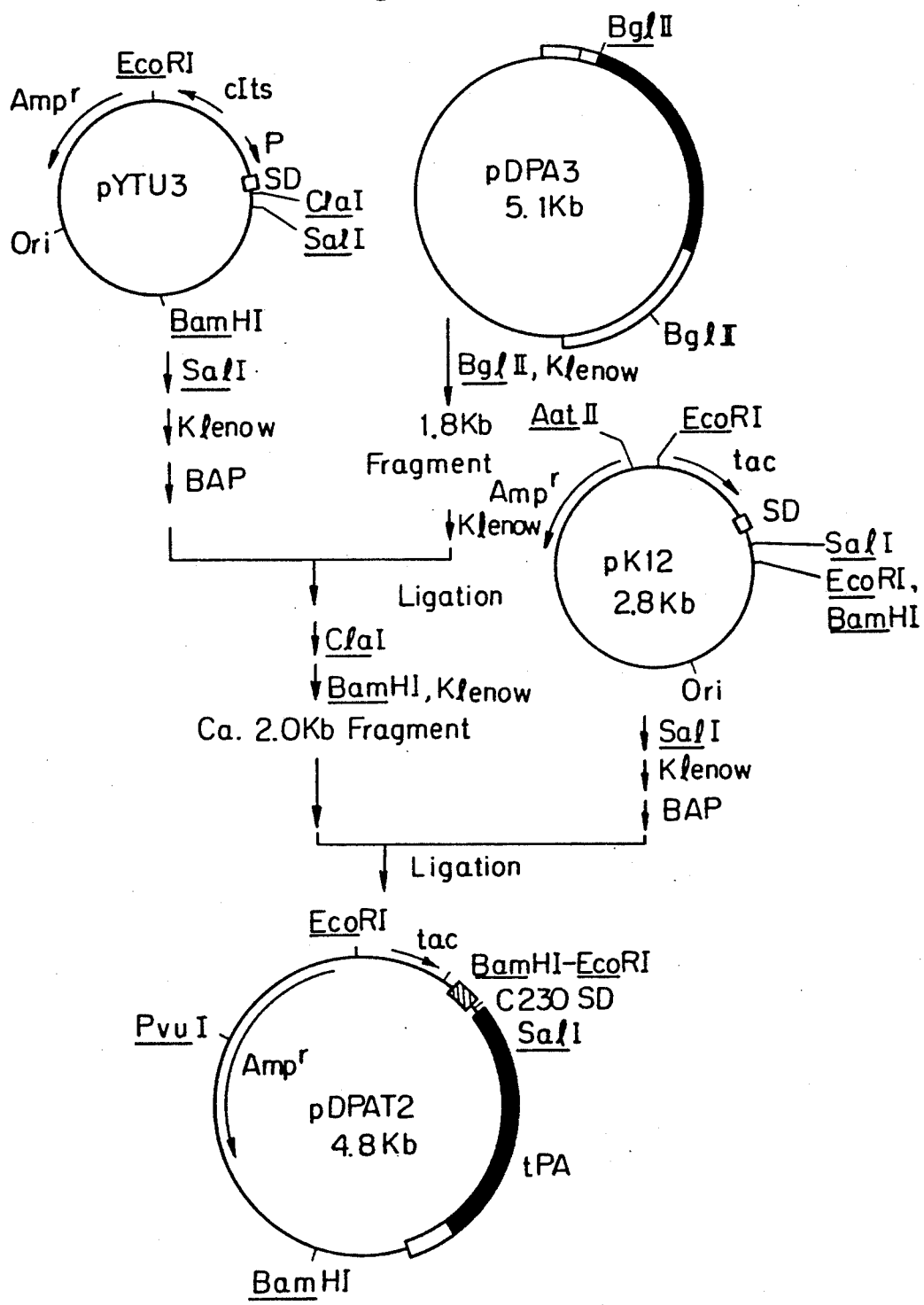
FIG. 13 represents the construction of plasmid pDPAT2 from plasmids pYTU3, pDPA3 and pK12.

A restriction endonuclease map of the plasmid pDPA3 is shown in FIG. 13. In this figure, a thick circle part corresponds to the cDNA insert. This cDNA insert was sequenced by a method of Maxam and Gilbert (literature 8), and the results thereof are shown in FIGS. 1-1 to 1-5. The cDNA sequence consists of 2459 base pairs excluding a poly A sequence present at 3'-terminal. Among them, 1548 bp encode 516 amino acids. This coding region includes, in addition to a sequence coding for a mature plasminogen activator (nucleotide number 261-1703), an upstream preprosequence (nucleotide number 156-260). There is a 5'-non-coding region (nucleotide number 1-155) upstream of the coding region, and a 3'-non-coding region (nucleotide number 1704-2459) downstream of the coding region.

REFERENCE EXAMPLE 4. PREPARATION OF mRNA mRNA was prepared by the method of J.M. Chirgwin et al (literature 2) using guanidine thiocyanate.

Twenty g of kidney tissue cells frozen at −80° C. was crushed with a Waring blender in liquid nitrogen and suspended in 80 ml of a 5 M guanidine thiocyanate solution (5 M guanidine thiocyanate, 0.5% sodium N-lauroylsarcosine, 25 mM sodium tartrate, 0.1 M mercaptoethanol, and 0.1% antifoam A). The suspension was homogenized with a Teflon homogenizer and nucleic acid was shared with a 20G ½ injection needle. Twenty-four ml of said solution was layered over 12 ml of 5.7 M CsCl and after centrifugation with a Beckman centrifuge in SW28 rotor for 24 hours at 15° C. and at 25,000 rpm the whole crude RNA was recovered.

The total crude RNA was dissolved in 2% potassium acetate solution and twice its volume of ethanol was added. The mixture was allowed to stand overnight at −20° C and centrifuged to recover precipitate.

In accordance with the method of H. Aviv et al (literature 3), poly(A)+RNA was isolated and purified by oligo (dT) cellulose column chromatography. Ten g of the kidney tissue cells yielded about 3 mg of the total RNA, of which 2 to 3% was poly(A)+RNA.

REFERENCE EXAMPLE 5. CONSTRUCTION OF cDNA LIBRARY (I)

cDNA synthesis was carried out using 40 μg of the poly(A)+RNA obtained in Reference Example 4. Using 40 μg of oligo (dT)$_{12-18}$ as a primer, reaction was carried out with 40 units of reverse transcriptase for 2 hours at 42° C. to synthesize the first chain and after removal of the template mRNA by alkali treatment the synthesis of the second chain was carried out with 100 units of E. coli DNA polymerase I Klenow fragment.

After elimination of the hairpin loop with S1 nuclease, the (dC)$_{10-20}$ chain was bonded to the 3' end of the double-stranded cDNA with terminal deoxynucleotidyl transferase, and about 400 ng of (dC) tailed cDNA was obtained.

This material was annealed together with 800 ng of a commercially available (dG) tailed pBR322 (PstI site) (New England Nuclear Inc.), and E. coli χ1776 was transformed by the Hanahan method (literature 9). A cDNA library (I) consisting of about 2×10$^5$ tetracycline-resistant and ampicillin-sensitive transformants was thus obtained.

The size of cDNA insert fragments was determined by the rapid isolation method (literature 10) using the alkali lytic procedure on these transformants.

REFERENCE EXAMPLE 6. PREPARATION OF SYNTHETIC DNA OLIGOMERS FOR USE AS cDNA LIBRARY SCREENING PROBES

The following 16 different DNA oligomers consisting of 14 nucleotides which are complementary to the mRNA corresponding to the amino acid sequence of the human urokinase: Asn$^{169}$, Gln, Pro, Trp, Phe$^{173}$ which has been reported by G.J. Steffens et al (literature 11) and Gunzler et al (literature 12) were synthesized by the phosphotriester method:

AACCAAGGTTGATT

AACCAAGGTTGGTT

AACCAGGGTTGATT

AACCACGGTTGATT

AACCACGGTTGGTT

AACCATGGTTGATT

AACCATGGTTGGTT

AACCAAGGCTGATT

AACCAAGGCTGGTT

AACCAGGGCTGATT

AACCAGGGCTGGTT

AACCACGGCTGATT

AACCACGGCTGGTT

AACCATGGCTGATT

AACCATGGCTGGTT

AACCAGGGTTGGTT

These 16 different DNA oligomers are referred to hereinafter as UK probe I.

For use as confirmatory probes, the following 8 different DNA oligomers consisting of 14 nucleotides which are complementary to the mRNA corresponding to Met$^{238}$, Try, Asn, Asp, Pro$^{287}$ were synthesized in the same manner:

5'GGATCATTATACAT 3'

GGATCGTTATACAT

GGATCGTTGTACAT

GGATCATTGTACAT

GGGTCATTATACAT

GGGTCGTTATACAT

GGGTCGTTGTACAT

GGGTCATTGTACAT.

These 8 different DNA oligomers are referred to hereinafter as UK probe II.

By use of T4 polynucleotidekinase, 200 ng each of the UK probes I and II was radioactively labeled at the 5'end with 3000 Ci/mmole $^{32}$P-γ-ATP to prepare probes for colony hybridization.

REFERENCE EXAMPLE 7. SCREENING OF cDNA LIBRARY (I)

(1) Screening

An autoclaved nitrocellulose filter (0.45 μm, Type-TM-2 made by Toyo Roshi Co.) was placed on an LB agar medium containing 15 μg/ml of tetracycline and the medium was inoculated with the transformants prepared in Reference Example 5 so as to allow about 2,000 transformant colonies to grow. After 8 hours of incubation at 37° C. the colonies were replicated on two nitrocellulose filters, which were incubated further for 3 hours at 37° C. The original nitrocellulose filter was used as a master filter, while two second filters were transferred to LB agar media containing 15 μg/ml of tetracycline and 100 μg/ml of chloramphenicol and were subjected to overnight incubation at 37° C. In accordance with the modified method of Grustein Hogness (literature 13) the filters were then placed over 0.5 M NaOH and 1.5 M NaCl for 3 minutes to effect colony lysis and DNA denaturation, and after neutralization over 0.5 M Tris-HCl (pH 7.6) and 1.5 M NaCl, were air-dried and baked for 2 hours at 80° C.

After washing the filters in 4×SSC for 30 minutes each at 60° C., prehybridization was carried out in 4×SSC, 10 ×Denhardt and 50 μg/ml denatured E. coli-DNA for one hour at 60° C., and after addition of 0.1 mM ATP and the radioactively labeled UK probe I (about 10$^7$ cpm/filter), hybridization was carried out for 16 hours at 37° C. After washing 6 to 8 times in 4 ×SSC at 39° C., the filters were air-dried and screened for transformants hybridizing with the UK probe I to obtain 21 candidate clones from 8×10$^4$ colonies. Plasmids of these clones are hereinafter referred to as plasmids pKYU1 to PKYU21.

Figure 6:
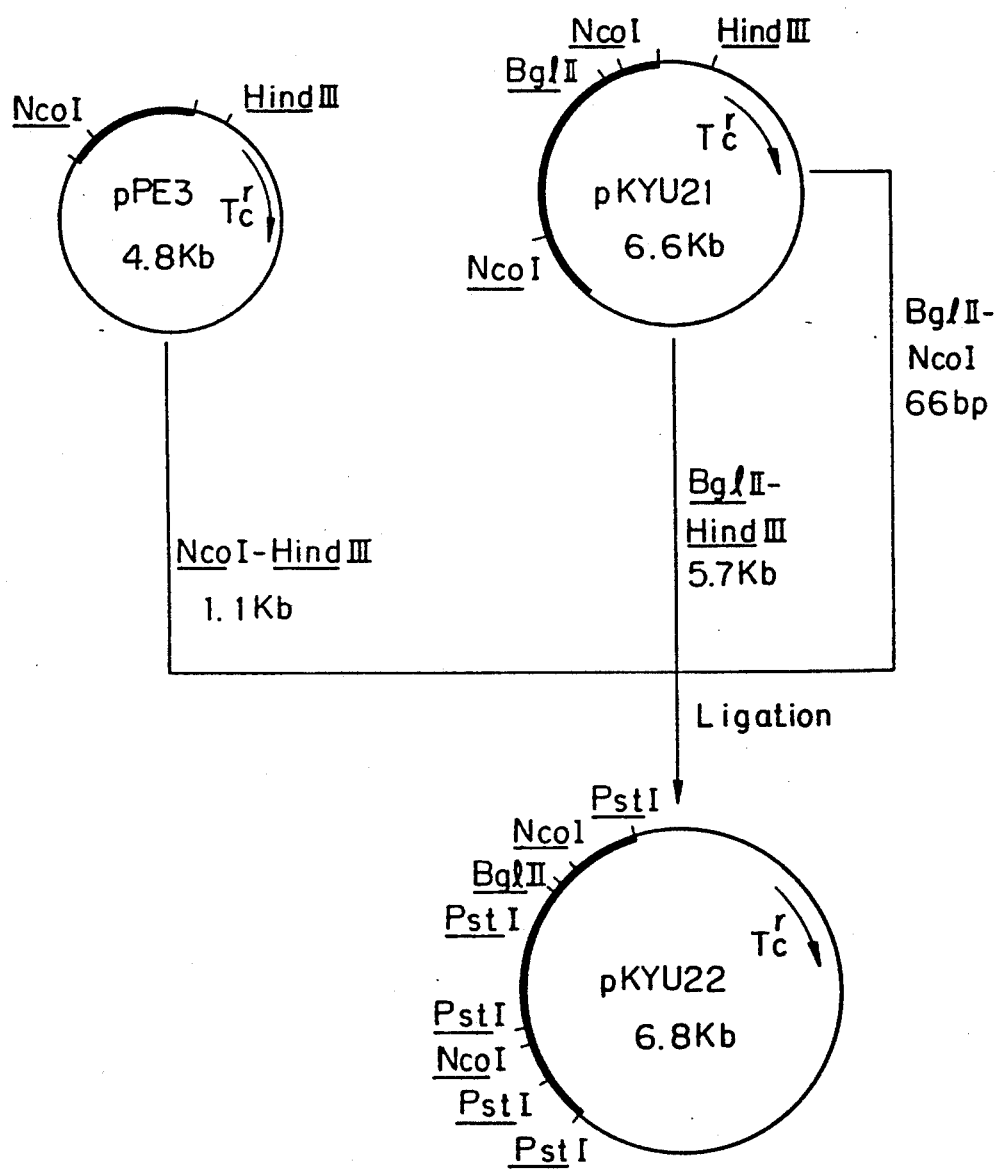
FIG. 6 represents the construction of plasmid pKYU22 from plasmids pPE3 and pKYU21.

The 21 candidate clones obtained were treated in the same manner as described above and clones hybridizing with the UK probe II were obtained. The plasmids in these clones are hereinafter referred to as plasmid pKYU21 (FIG. 6).

(2) Characteristics of pKYU21 Plasmid DNA

After digesting the pKYU21 plasmid DNA with various restriction endonucleases and subcloning them to M13mp8 by the Maxam-Gilbert method (literature 8), determination of the nucleotide sequence was carried out by the dideoxy chain termination method (literature 14). On contrasting this sequence with the well-known amino acid sequence of urokinase it was confirmed that although the cDNA contains th entire code region of low molecular weight urokinase, about 100 bp long DNA in the 5'-end region of the coding region of high molecular weight urokinase is lacking.

REFERENCE EXAMPLE 8. CONSTRUCTION OF cDNA LIBRARY (II) BY PRIMER EXTENSION REACTION

Based on the nucleotide sequence determined in Paragraph (2) of Reference Example 7, the following DNA oligomer:

5'CTGAAGAGCATCAGA 3' consisting of 15 nucleotides which are complementary to the mRNA sequence corresponding to $^{89}$Ser, Asp, Ala, Leu, Glu$^{93}$ was synthesized by the phosphotoresister method.

Employing 100 μg of poly(A)+RNA as a template and complying with the method of Agarwall et al (literature 15) or the method of Stewad et al (literature 16), the first cDNA chain was synthesized using 100 units of reverse transcriptase together with 1 μg of 5'$^{32}$P-labeled primer followed by the synthesis of the second chain with 100 units of E. coli DNA polymerase I Klenow fragment. Then the single-stranded DNA was digested with S1 nuclease and (dC)n chain was added at the 3'-end using terminal deoxynucleotidyl transferase. After annealing this dC tailed insert (cDNA) and a dG tailed vector (pBR322) together, E. coli χ1776 was transformed to obtain a cDNA library (II) consisting of about 5×10$^4$ transformants.

REFERENCE EXAMPLE 9. SCREENING OF cDNA LIBRARY (II)

The transformants obtained in Reference Example 8 were subject to hybridization in the same manner as that described in Paragraph (1) of Reference Example 7. In this case, a 150 bp PstI-BglIII 5 'digestion fragment from pKYU21 radioactivity labeled by the nick translation method (literature 9) using $^{32}$p-α-dCTP (3000 Ci/mole) was used as a probe. The hybridization was carried out at 60° C.

Figure 7:
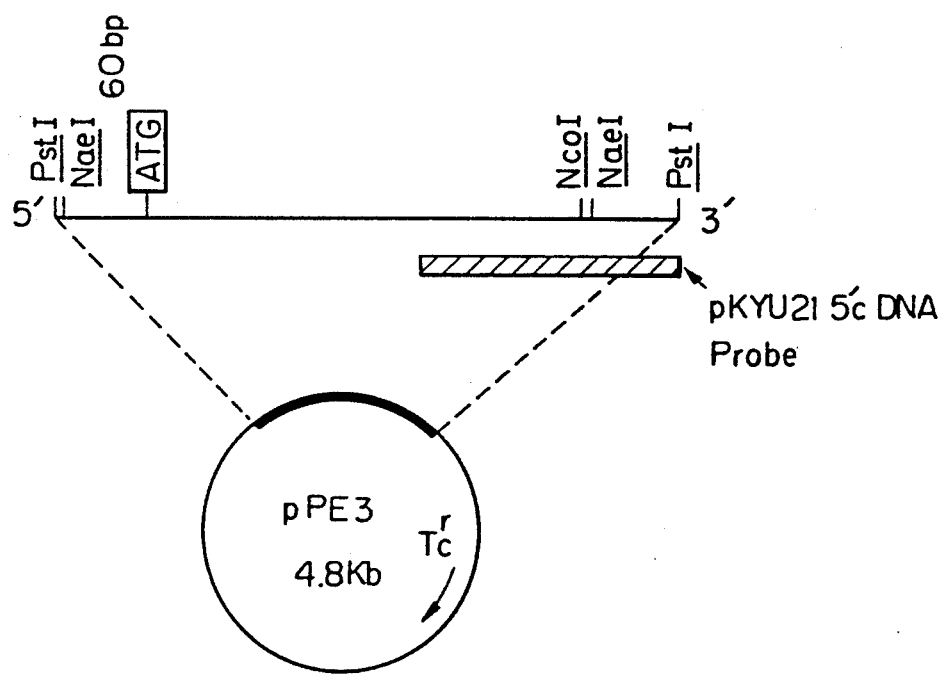
FIG. 7 represents the restriction endonuclease map of plasmid pPE3.

The filter was air-dried after washing two or three times with 2 ×SSC at 60° C., and clones hybridizing with said probe were retrieved by autoradiography. Eight positive clones were obtained out of about 3×10$^4$ clones. The plasmids in these clones are hereinafter referred to as plasmids pPE1 to pPE8. On digestion of these plasmid DNAs with restriction enzyme PstI it was confirmed that Plasmid pPE3 (FIG. 7) contains an approximately 40 bp long cDNA insert.

The fragments obtained through digestion of DNA of plasmid pPE3 with restriction endonuclease PstI were subcloned into M13pm8, and determination of the base sequence was carried out by the dideoxy chain termination method (literature 14). As the result, it was confirmed that the cDNA contains not only a sufficiently long coding region on the 5'-end side of the prourokinase gene but also a 66 bp long 5'-nontranslation region upstream of the translation initiation codon ATG (FIG. 2-1 to 2-5).

REFERENCE EXAMPLE 10. CONSTRUCTION OF PROUROKINASE GENE (FIG. 6)

Five μg of DNA of plasmid pKYU12 containing an entire coding region of the low molecular weight urokinase was digested with 10 units each of restriction endonucleases BglIII and HindIII and then electrically eluted to give about 5.7 Kbp DNA fragment, while DNA of said plasmid pKYU21 was digested with 10 units each of BglII and NcoI and ten eluted to give a 66 bp DNA fragment. Then again 5 μg of DNA of plasmid pPEP3 obtained in Reference Example 6 was digested with 10 units each of NcoI and HindIII to give about 1.1 Kbp DNA fragment. These three different DNA fragments were repeatedly extracted with phenol/chloroform, precipitated with 2 volumes of ethanol so as to purify and recover the precipitate. These three different DNA fragments were ligated together with T4 DNA ligase for transformation into E. coli χ1776. The resultant transformants were screened by the rapid isolation method using the alkali lysis procedure and a clone carrying plasmid pKYU22 that contains the entire gene for prourokinase was obtained.

The clone, E. coli χ1776/pKYU22 was deposited on Jan. 11, 1985 with F.R.I. as FERM P-8041 and on Jan. 22, 1986 was placed under international deposition as FERM BP-968 pursuant to the provisions of the Budapest Treaty.

REFERENCE EXAMPLE 11. NUCLEOTIDE SEQUENCE DETERMINATION OF PLASMID pKYU 22 INSERT SITE

The nucleotide sequence at the insert site of plasmid pKYU22 was determined by the Maxam-Gilbert method, and the dideoxy chain termination method preceded by subcloning to M13mp8. The result is presented in FIGS. 2-1 to 2-5.

As seen from these figures, the insert consists of a 66 bp 5'-non-coding region, a leader sequence ATG(Met)-GGC(Gly), a prourokinase coding region AGC(Ser)-CTC(Lev), a translation stop codon TGA(XXX), and a 3'-non-translation codon downstream of the stop on.

Figure 8:
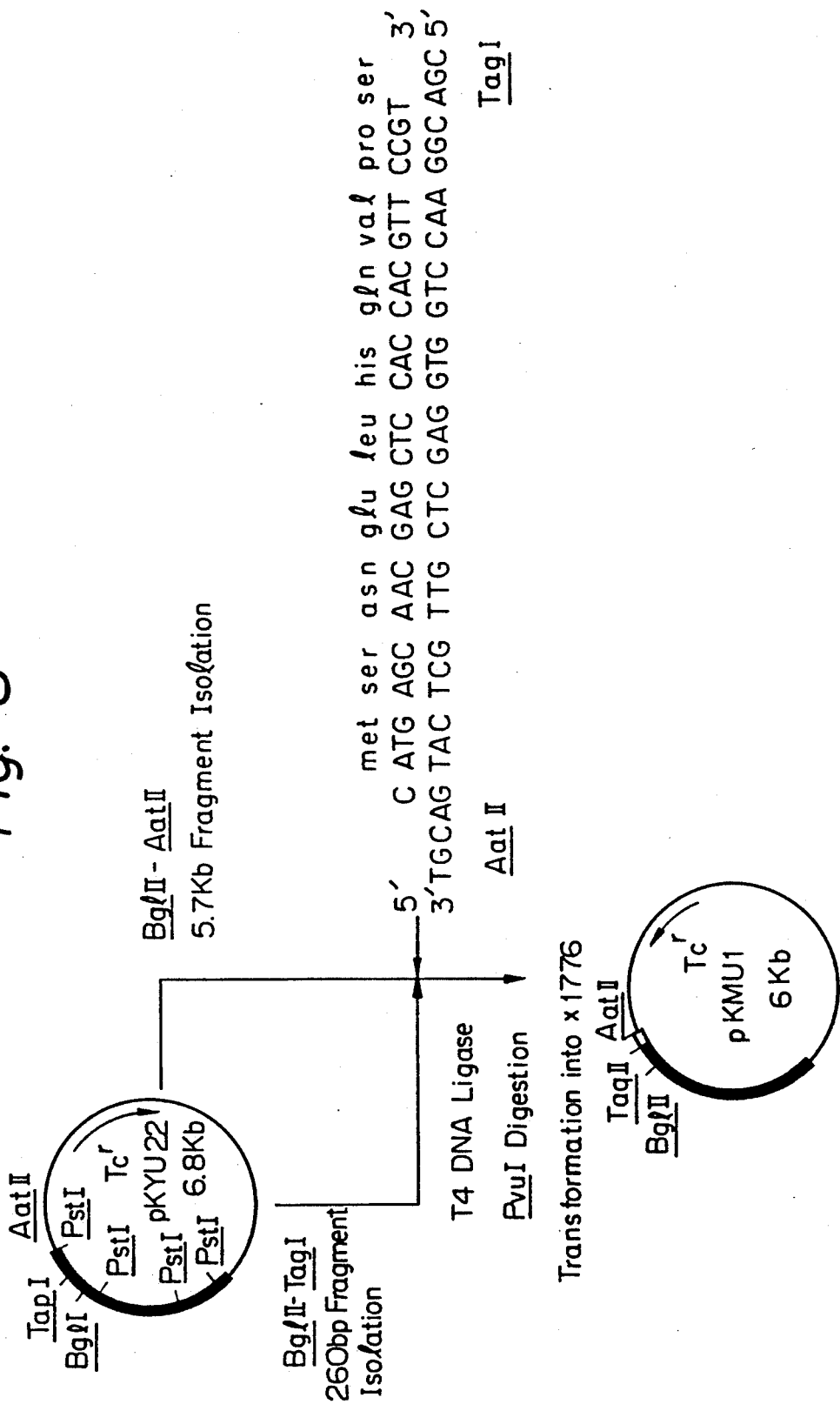
FIG. 8 represents the construction of plasmid pKMU1 from plasmid pKYU22 and a synthetic oligodeoxyribonucleotide.

REFERENCE EXAMPLE 12. SYNTHESIS OF PROUROKINASE GENE MODIFIED AT 5' END REGION (FIG. 8)

Codons of a 5'-terminal region of native cDNA coding for prourokinase were replaced so as to permit the prourokinase gene to be efficiently expressed in E. coli under the SD sequence of the Pseudomonas putide-derived C230 gene; a translation start codon ATG(Met) was provided adjacent to and upstream of a codon for the first amino acid (Ser) so that prourokinase could be directly expressed; and a restriction enzyme recognition site AatII was provided to join the coding region near to an SD sequence of the expression vector. For this purpose, a double stranded DNA oligomer shown in FIG. 8 was synthesized by a phosphotriester method. This double stranded synthetic DNA has an AatII site at one end to insert it into a vector, and a TaqI site at another end to join it to the prourokinase gene.

The following three single-chain DNA oligomers comprising 29, 15, and 20 nucleotides respectively were synthesized by the phosphotriester method:

5' CATGAGCAACGAGCTCCACCAGGTTCCGT 3'
3' TGCAGTACTCGTTGC 5'
3' TCGAGGTGGTCCAAGGCAGC 5'

Next, 1 μg each of the synthetic DNA oligomers was heated for 2 minutes at 95° C., phosphorylated at the 5' end with T4 polynucleotide kinase and purified using a Sep Pak (C18) column (Waters). After drying, the purified material was dissolved in 50 μl of 20 mM Tris-HCl (pH 7.6) and 10 mM MgCl$_2$, and annealed by heating for 2 minutes at 95° C., cooling slowly to room temperature, and then maintaining the solution overnight at 12° C. to give the following double-stranded DNA:

```
5' CATGAGCAACGAGCTCCACCAGGTTCCGT 3'
3' TGCAGTACTCGTTGCTCGAGGTGGTCCAAGGCAGC
     AatII      SstI      BstNI      TaqI
```

On the one hand, 5 μg of DNA of plasmid pKYU22 was digested with restriction endonucleases BglII and AatII, and about 5.7 Kb DNA fragment was recovered by electric elution. On the other hand, 5 μg of DNA of the same plasmid pKYU22 was digested with restriction endonucleases PstI and BglII and about 400 bp DNA fragment was obtained by electric elution. This fragment was again digested with restriction endonucleases TaqI and about 260 bp DNA fragment was recovered by electric elution. These two different DNA fragments were recovered and purified by phenol/chloroform extraction, and precipitation with 2 volumes of ethanol.

These two different DNA fragments and the aforesaid double-stranded synthetic DNA oligomer were ligated together using T4 DNA ligase and the ligation product was used to transform *E. coli* χ1776. Then the transformants were screened by the rapid isolation method by the alkali lysis procedure, and a clone *Escherichia coli* χ1776/pKMU1 carrying plasmid pKMU1 that contains a modified prourokinase gene was obtained. The clone *E. coli* χ1776/pKMU1 has been deposited with F.R.I. on Jan. 11, 1985 as FERM P-8040.

Figure 9:
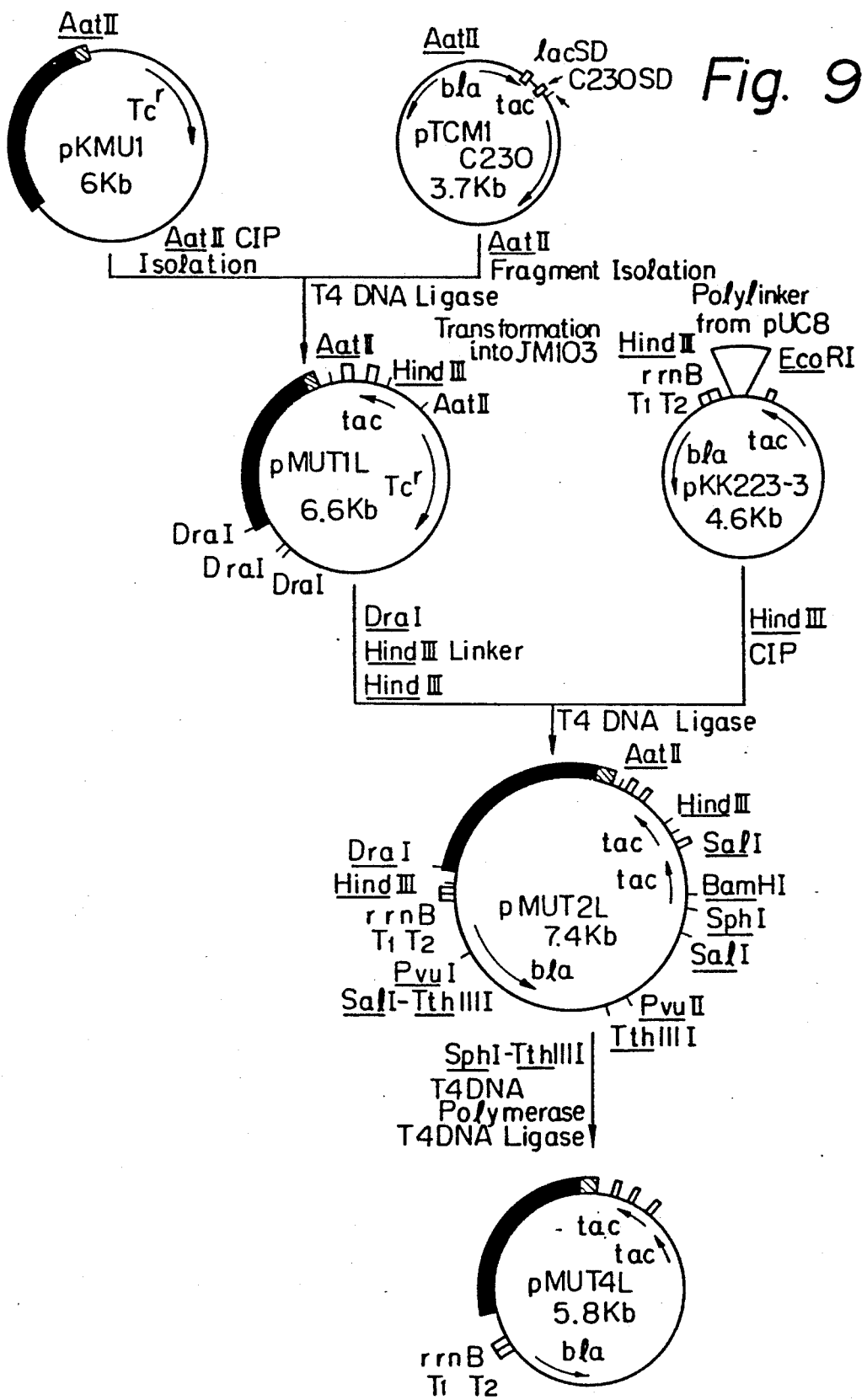
FIG. 9 represents the construction of plasmid pMUT4L.

REFERENCE EXAMPLE 13. CONSTRUCTION OF PLASMID pMUT4L (FIG. 9)

Expression plasmid pMUT4L containing a human prourokinase gene without a point mutation was constructed from the above-mentioned plasmid pKMU1, and an expression vector pTCM1. *E. coli* JM103/pTCM1 containing the plasmid pTCM1 was deposited with F.R.I. on Aug. 17, 1984 as FERM P-7779.

Five μg of plasmid pKMU1 from Reference Example 12 was digested with 10 units of restriction endonuclease AatII and the digest was isolated after treatment with calf intestinal phosphatase (CIP). On the other hand, 5 μg of plasmid pTCM1 was digested with 10 units of restriction endonuclease AatII and about 500 bp DNA fragment was isolated by the electric elution. These two different DNA fragments were purified by repeated phenol/chloroform extraction and ethanol precipitation.

Both of these DNA fragments were joined together using T4 DNA ligase and were transformed into *E. coli* JM103. The transformants were screened by the rapid isolation method by the alkali lysis procedure, and a clone carrying plasmid pMUT1L in which tac promoter/operator and C230SD sequence having the normal orientation with reference to the prourokinase gene was obtained.

Next, 5 μg of plasmid pKK223-3 (literature 17, 18 and 19) was digested with 10 units of restriction endonuclease HindIII, and the digest was treated with calf intestinal phosphatase (P.L. Biochemicals).

On the other hand, 1 μg of the plasmid pMUT1L obtained as above was digested with 4 units of restriction endonuclease DraI and the digestion fragment and 1 μg of 5'-phosphorylated HindIII linker (dCAAGCTTG) were ligated with T4 DNA ligase. Digestion was carried out using 12 units of restriction endonuclease HindIII, and the digest was dissolved in 0.15 M NaCl. The solution was extracted with an equal volume of phenol/chloroform and the DNA was precipitated by the addition of 2 volumes of ethanol. The precipitate was collected at 16,000 rpm and at 4° C. and was dried.

The resultant pMUT1L digestion fragment and the HindIII digestion fragment of aforesaid pKK223-3 were ligated using T4 DNA ligase and were transformed into *E. coli* JM103. The transformants were screened by the alkali lysis procedure and a clone, *E. coli* JM103/pMUT2L containing plasmid pMUT2L was obtained.

Five μg of plasmid pMUT2L was digested with 10 units each of restriction endonucleases SphI and Tth111I, and after extraction with phenol/chloroform DNA was precipitated with ethanol. The DNA thus recovered was blunt-ended using T4 polymerase in the presence of 0.1 mM dGTP, dCTP, dATP and TTP, and was recyclized by T4 DNA ligase. The DNA was transformed into *E. coli* JM103 and colonies were allowed to form on an LB agar medium containing 50 μg/ml of ampicillin. The transformants were screened by the alkali lysis procedure (literature 10) and a clone, *E. coli* JM103/pMUT4L was obtained.

Figure 10:
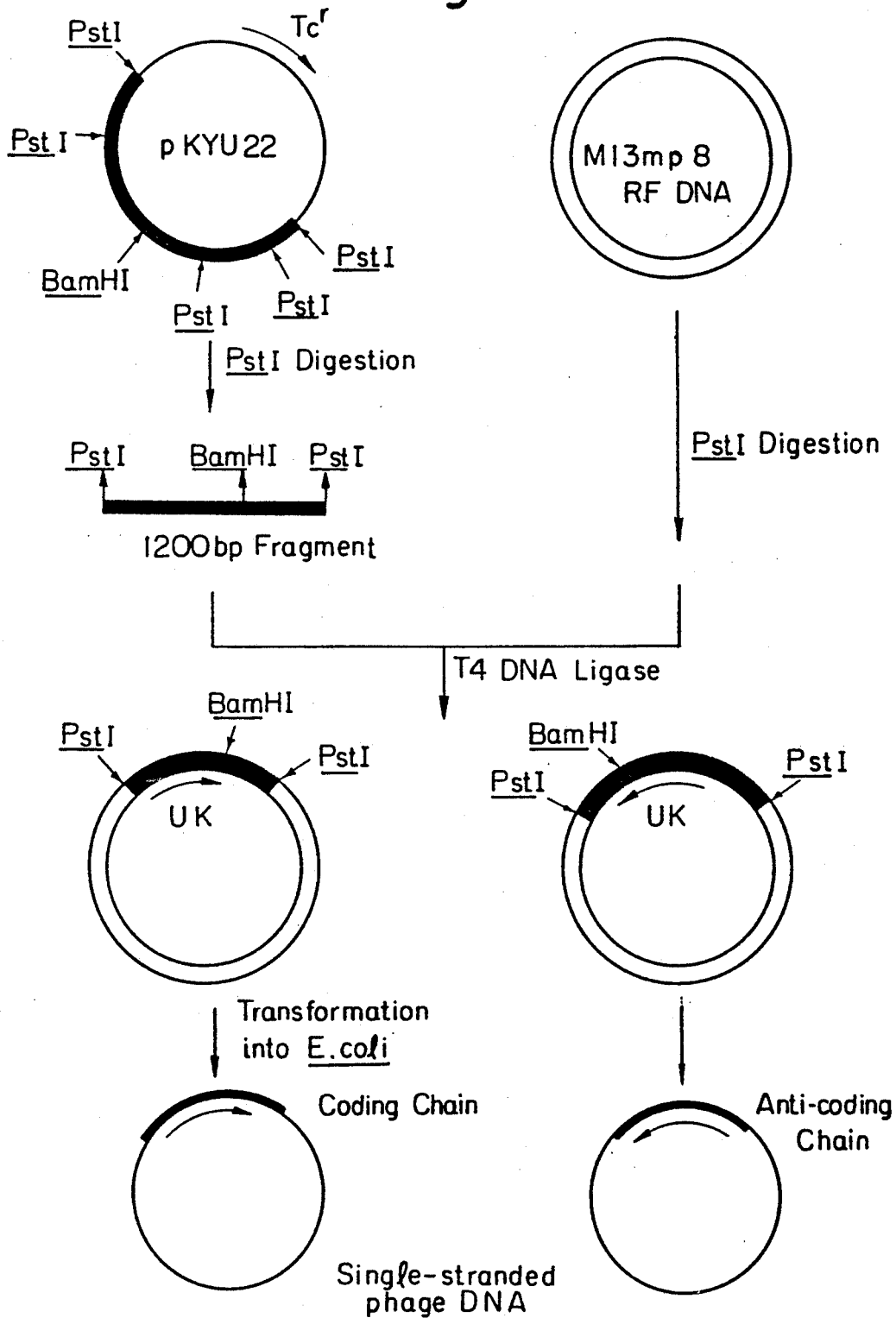
FIG. 10 represents the construction of a single-stranded phage DNA containing a 1200 bp insert from plasmid pKYU22 and a phage M13pm8 RF DNA.

REFERENCE EXAMPLE 14. INTRODUCTION OF SPECIFIC BASE SUBSTITUTION MUTATION INTO CODON FOR AMINO ACID 157 USING M13 PHAGE (1) Preparation of Single-strand Template DNA (FIG. 10)

One μg each of plasmid pKYU22 and phage M13mp8 double-stranded DNA was digested in 20 μl of a solution containing 10 mM Tris-HCl (pH 7.5), 7 mM MgCl$_2$, 7 mM β-melcaptoethanol, and 50 mM NaCl for one hour at 37° C. using 5 units of PstI. The respective DNA fragments were recovered after treatment with phenol and precipitation with ethanol. A mixture of these two different DNA fragments was subjected to ligation reaction in 20 μl of a solution containing 66 mM Tris-RCl (pH 7.5), 5 mM MgCl$_2$, 5 mM DTT, and 1 mM ATP for 16 hours at 12° C. using T4 DNA ligase. Transformation into *E. coli* JM103 was carried out using the reaction mixture in accordance with the method of Messing et al (literature 19) and the transformants were plated with soft agar containing 0.02% X-gal and 1 mM IPTG. The plates were incubated overnight at 37° C. Single-stranded DNA was prepared from white plaques formed by the recombinant.

Using some of the resultant single-strand DNA as a template the base sequence was determined using the dideoxy procedure in accordance with the method of Messing et al (literature 20) and sequence of the cloned single-strand DNA was confirmed. The coding chain and anticoding chain were obtained as shown in FIG. 10.

Figure 11:
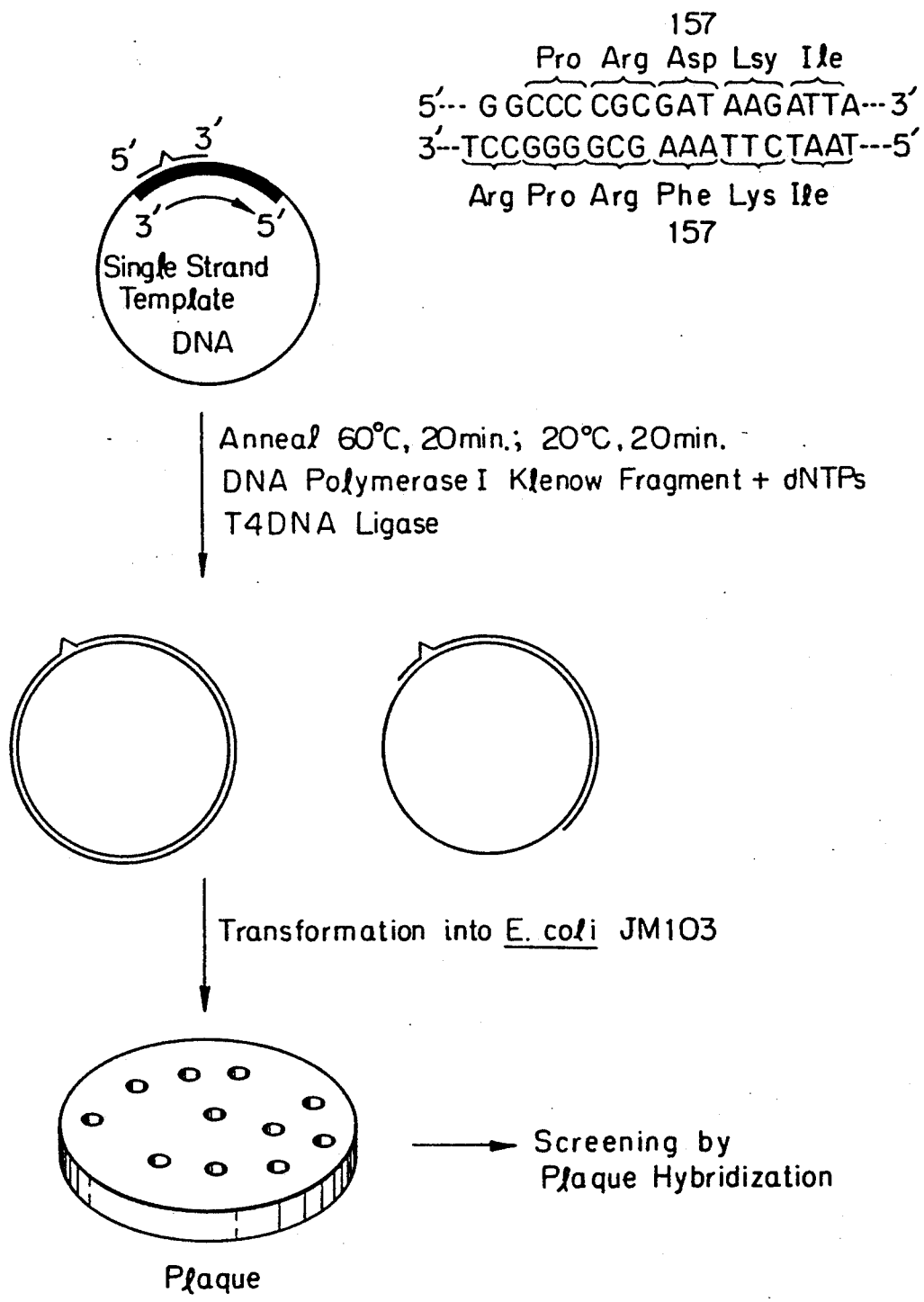
FIG. 11 represent a process for the introduction of a point mutation using a primer.

(2) Introduction of Specific Base Substitution Mutation (FIG. 11)

Using the resulting recombinant M13 phage single-strand DNA (an anticoding chain of the urokinase gene has been cloned) as a template, introduction of site-directed mutagenesis was carried with a another oligonucleotide mutagen. In this case, the following synthetic oligonucleotide:

5'GGCCCCGCGATAAGATTA 3' was used as a primer. Although this 18-base oligonucleotide is complementary to the urokinase gene in the single-strand template DNA, two base have undergone changes wherein codon TTT which specifies phenylalanine has changed to codon GAT specifying aspartic acid.

Using the aforesaid oligonucleotide as a primer, double-strand DNA was synthesized in vitro. That is, 2 pmole of 5'-phosphorylated primer was added to 0.5 pmole of the template single-strand DNA and the mixture was incubated in 10 µl of a solution containing 7 mM Tris-HCl (pH 7.5), 0.1 mM EDTA, 20 mM NaCl, and 7 mM MgCl$_2$ for 20 minutes at 60° C. followed by further incubation for 20 minutes at 23° C. Next, to the reaction mixture was added 0.5 mM each of dATP, dGTP, dTTP and dCTP to a combined volume of 20 µl to which was added 2 units of DNA polymerase Klenow fragment. The mixture was incubated for 20 minutes at 23° C., and after the addition of 1 µl of 10 mM ATP and 1 unit of T4 DNA ligase the mixture was incubated overnight at 12° C. In accordance with the method of Messing et al (literature 20) the aforesaid reaction mixture was directly transformed into E. coli JM103. About 10,000 phage plaques per microliter of said reaction mixture were thus obtained.

After the transfer of the resulting plaques from a soft agar medium to a nitrocellulose filter in accordance with the method of Benton and Davis et al (literature 21), the filter was baked in vacuo for 2 hours at 80° C. The nitrocellulose filter was hybridized with the primer oligonucleotide labeled with $^{32}$P as a probe in a mixture of 6 ×SSC and 10 ×Denhardt overnight at 37° C. The filter was then washed in 6 ×SSC at 52° C. and mutant phage plaques giving positive signals were autoradiographically isolated. From the mutant phage, mutant phage DNA of the double-strand type (pm3) was obtained. Using the mutant phage DNA as a template according to the dideoxy method, the nucleotide sequence of the mutant DNA was determined, and the occurrence of the desired single base substitution mutation was confirmed.

In addition, it is possible to replace codon TTT specifying phenylalanine at 157 position with the Glu-specifying codon GAA using the following oligonucleotide:

5'GGCCCCGCGAAAAGATTA 3' as a mutagen.

Figure 12:
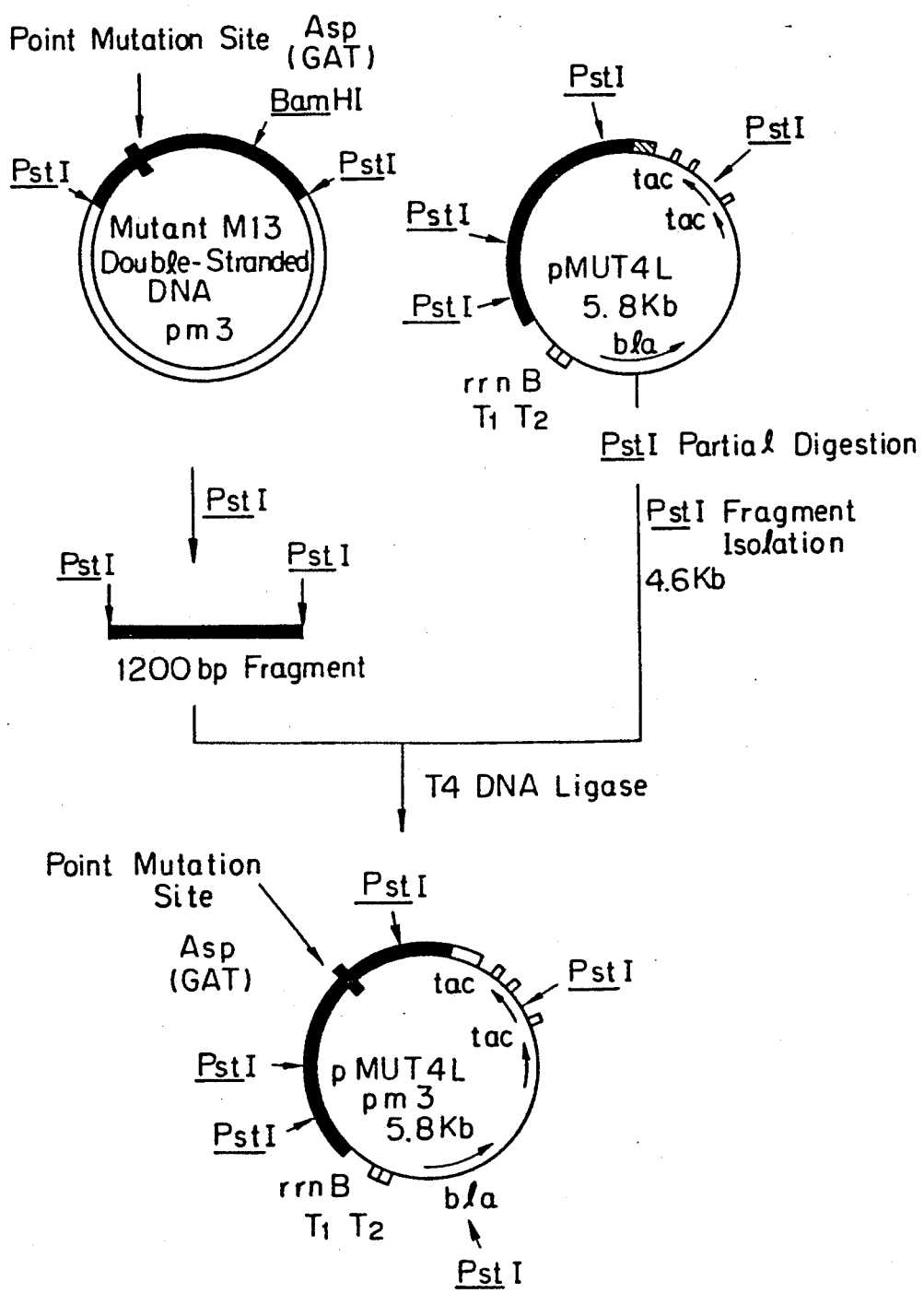
FIG. 12 represents the construction of plasmid pMUT4Lpm3 from a mutant phage M13 double stranded DNA (pm3) and plasmid pMUT4L.

REFERENCE EXAMPLE 15. CONSTRUCTION OF PLASMID pMUTb 4Lmp3 (FIG. 12)

Expression plasmid pMUT4Lpm3 wherein the human urokinase structural gene having the aforementioned point mutation had been inserted downstream of E. coli tac promoter was constructed in the following manner:

After complete digestion of 10 µg of mutant M13 double-strand DNA (pm3) with PstI, a fragment about 1.2 Kbp in length was isolated. On the other hand, 10 µg of plasmid pMUT4L was partially digested with PstI and a fragment about 4.6 Kbp in length was isolated from which a fragment about 1.2 Kbp in length had been eliminated.

Each of the above two fragments was recovered by treating with phenol and precipitating with ethanol and then the precipitates were mixed. The mixture was subjected to ligation reaction overnight at 12° C. using T4 DNA ligase and the reaction mixture was used to transform E. coli HB101. The transformants were then screened by the alkali lysis procedure and a clone containing plasmid pMUT4Lpm3 was obtained. Escherichia coli 1776/pMUT4Lpm3 carrying plasmid pMUT4Lpm3 was deposited on Jul. 11, 1985 with F.R.I. as FERM P-8341 and was placed under international deposition on Jan. 22, 1986 as FERM BP-971 pursuant to the provisions of the Budapest Treaty.

REFERENCE EXAMPLE 16. CONSTRUCTION OF PLASMID pMUT4Lpm1

Mutant double-stranded phage M13RFpml containing a DNA fragment wherein a codon AAA for 135th lysine is mutated to a codon CAA for glutamine was obtained by the same procedure as described in Reference Example 14, except that the following synthetic oligonucleotide:

5'GATGGACAAAAGCCC3' was used. The DNA sequence of the mutant DNA thus obtained was determined by dideoxy method using the mutant phage DNA as a template, and was confirmed to contain a desired point mutation.

Next, from the phage M13RFpml and the plasmid pMUT4L, pMUT4Lpml was constructed according to the same procedure described in Reference Example 15.

REFERENCE EXAMPLE 17. CONSTRUCTION OF PLASMID pMUT4Lpm4

A mutated double-strand phage containing a DNA fragment wherein a codon AAA for 135th lysine is mutated to a codon for glutamine was obtained by the same method as described in Reference Example 14, except that the following synthetic oligonucleotide:

5'GATGGACAAAAGCCC3' was used.

From the mutated phage thus obtained, a single-strand phage was obtained according to the same procedure as described in Reference Example 14. Using the single-strand phage as a template, a codon TTT for 157th phenylalanine was then mutated to a codon GAT for aspartic acid according to the same procedure as described above, except that the following synthetic oligonucleotide:

5'GGCCCCGCGATAAGATTA3' was used, to obtain a mutated double-strand phage M13RFpm4 containing a DNA fragment wherein a codon AAA for 135th lysine is mutated to a codon CAA for glutamine and a codon for 157th phenylalamine is mutated to a codon for aspargic acid.

Next, from the double mutated phage M13RFpm4 thus obtained and the plasmid PMUT4L, plasmid pMUT4Lpm4 was constructed according to the same procedure as described in Reference Example 15.

Figure 19:
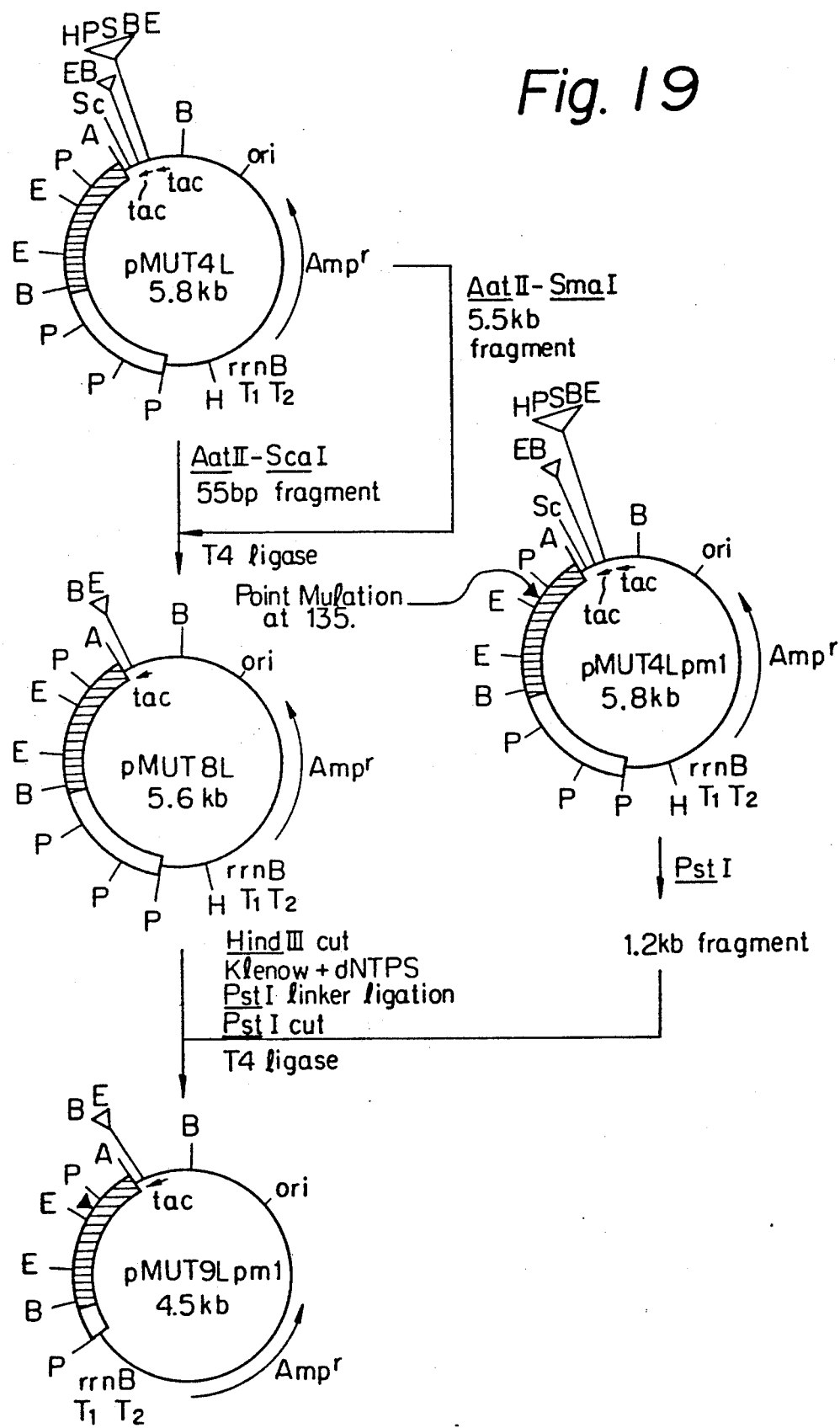
FIG. 19 represents the construction of plasmid pMUT9Lpml from plasmids pMUT4L and pMUT4pml.

REFERENCE EXAMPLE 18. CONSTRUCTION OF PLASMID pMUT9Lpml (FIG. 19)

5 µg of plasmid pMUT4L constructed in Reference Example 13 was digested with 50 units of ScaI and 100 units of AatII in 100 µl of a buffer containing 10 mM Tris-HCl (pH7.5), 7 mM MgCl$_2$, 125 mM NaCl, 7 mM β-mercaptoethanol at 37° C. for 6 hours. The reaction mixture was then subjected to 0.7% agarose gel electrophoresis, and a DNA fragment of about 5500 bp was recovered by a conventional means. On the other hand, 10 μg of the same plasmid pMUT4L was digested with 50 units of AatII and 50 units of SmaI in 100 μl of a buffer containing 10 mM Tris-HCl (pH7.5), 7 mM MgCl$_2$, 60 mMKCl, 7 mM β-mercaptoethanol at 37° C. for 6 hours. The reaction mixture was then subjected to 2.0% agarose gel electrophoresis, and a DNA fragment of 55 bp was recovered by a conventional means. Two DNA fragments thus obtained were reacted with 5 units of T4 DNA ligase in 10 μl of a buffer containing 66 mM Tris-HCl (pH7.6), 6.6 mM MgCl$_2$, 10 mM DTT and 1 mM ATP at 12° C. for 15 hours. The reaction mixture was used to transform *E. coli* JM103 according to a conventional procedure, and ampicillin resistant transformants thus obtained were screemed for a colony containing plasmid pMUT8L shown in FIG. 19, and from the selected colony, the plasmid pMUT8L was isolated by a conventional means.

5 μg of the plasmid pMUT84 thus obtained was digested with 50 units of HindIII in 100 μl of a buffer containing 10 mM Tris-HCl (pH7.5), 7 mM MgCl$_2$ and 60 mM NaCl at 37° C. for 2 hours. After phenol extraction and ethanol precipitation of the reaction mixture, the precipitate was treated with one unit of Klenow fragment in 20 μl of a buffer containing 50 mM Tris-HCl (pH7.2), 10 mM MgCl$_2$, 0.1 mM DTT and 80 μM dNTPs at 22° C. for 30 minutes. After phenol extract and ethanol precipitation of the reaction mixture, the precipitate was treated with 5 units of T4 DNA ligase in 20 μl of a buffer containing 1 μg of pSsTI linker, and 66 mM Tris-HCl (pH7.6), 6.6 mM MgCl$_2$, 10 mM DTT and 1 mM ATP at 12° C. for 2 hours. After phenol extraction and ethanol precipitation of the reaction mixture, the precipitate was digested with 50 units of PstI in 100 μl of a solution containing 20 mM Tris-HCl (pH7.5), 10 mM MgCl$_2$ and 100 mM NaCl at 37° C. for 2 hours. The reaction mixture was then subjected to 0.7% agarose gel electrophoresis, and a DNA fragment of about 4300 bp was recovered by a conventional means.

On the other hand, 5 μg of the plasmid pMUT4Lpml constructed in Reference Example 16 was digested with 50 units of PstI in 100 μl of a buffer containing 20 mM Tris-HCl (pH7.5), 10 mM MgCl$_2$ and 100 mM NaCl at 37° C. for 2 hours. The reaction mixture was then subjected to 0.7% agarose gel electrophoresis, and a DNA fragment of about 1200 bp was recovered by a conventional means.

Two DNA fragments thus obtained were mixed, and ligated using 5 units of T4 DNA ligase in 20 μl of a buffer containing 66 mM Tris-HCl (pH7.6), 6.6 mM MgCl$_2$, 10 mM DTT and 10 mM ATP for 15 hours at 12° C. The reaction mixture was used to transform *E. coli* JM103 according to a conventional procedure, and ampicillin resistant transformants thus obtained were screened for a colony containing plasmid pMUT9Lpml, and the plasmid pMUT9Lpml was isolated according to a conventional means.

EXAMPLE 1. CONSTRUCTION OF PLASMID pDPAT 2

Fifty μg of plasmid pDPA3 was digested with 75 units of BglII in 200 μl of a buffer containing 10 mM Tris-HCl (pH7.5), 7 mM MgCl$_2$, 100 mM NaCl, and 7 mM β-mercaptoethanol at 37° C. for 4 hours. After ethanol precipitation, the precipitate was reacted with 5 units of Klenow fragment in 50 μl of a buffer containing 50 mM Tris-HCl (pH7.2), 10 mM MgCl$_2$, 0.1 mM DTT and 80 mM dNTP at 22° C. for 30 minutes. The reaction mixture was subjected to 0.7% agarose gel electrophoresis, and a DNA fragment of about 1800 bp was recovered by a conventional means. This DNA fragment is designated as DNA fragment (A).

On the other hand, 10 μg of plasmid pYTU3 was digested with 20 units of SalI in 50 μl of a buffer containing 10 mM Tris-HCl (pH7.5), 7 mM MgCl$_2$, 150 mM NaCl, 0.2 mM EDTA and 7 mM β-mercaptoethanol at 37° C. for 4 hours. After ethanol precipitation, the precipitate was treated with 2 units of Klenow fragment in 20 μl of a buffer containing 50 mM Tris-HCl (pH7.2), 10 mM MgCl$_2$, 0.1 mM DTT, 80 μM dNTP at 22° C. for 30 minutes. After ethanol precipitation, the precipitate was treated with one unit of alkaline phosphatase (from bovine intestine) in 20 μl of a buffer containing 50 mM Tris-HCl (pH9.0), 1 mM MgCl$_2$, 0.1 mM ZnCl$_2$, 1 mM spermidine at 37° C. for 30 minutes. Phenol treatment and ethanol precipitation were carried out. The precipitate was dissolved in 20 μl of a solution containing 10 mM Tris-HCl (pH7.5) and 1 mM EDTA. The solution contains 0.5 μg/μl of DNA. 5 μg of this DNA and 5 μg of DNA fragment (A) described above were treated with 10 units of T4 DNA ligase in 30 μl of a buffer containing 66 mM Tris-HCl (pH7 6), 6.6 mM MgCl$_2$, 10 mM DTT and 1 mM ATP at 15° C. for 15 hours. After ethanol precipitation, the precipitate was digested with 15 units of ClaI in 30 μl of a buffer containing 6 mM Tris-HCl (pH7.9), 6 mM MgCl$_2$ and 50 mM NaCl at 37° C. for 4 hours. After ethanol precipitation, the precipitate was digested with 15 units of BamHI in 30 μl of a buffer containing 10 mM Tris-HCl (pH8.0), 7 mM MgCl$_2$, 100 mM NaCl and 2 mM β-mercaptoethanol at 37° C. for 4 hours. After DNA in the reaction mixture was precipitated with ethanol, the precipitate was treated with 2 units of Klenow fragment in 30 μl of a buffer containing 50 mM Tris-HCl (pH7.2), 10 mM MgCl$_2$, 0.1 mM DTT and 80 mM dNTP at 22° C. for 30 minutes. The reaction mixture was subjected to 0.7% agarose gel electrophoresis, and a DNA fragment of about 2,000 bp was recovered by a conventional means. This DNA fragment was designated as DNA fragment (B).

On the other hand, 2 μg of plasmid pK12 was digested with 10 units of SalI in 20 μl of a buffer containing mM Tris-HCl (pH7.5), 7 mM MgCl$_2$, 150 mM NaCl, 0.2 mM EDTA and 7 mM β-mercaptoethanol at 37° C. for hours. After ethanol precipitation, the precipitate was treated with 20 units of Klenow fragment in 20 μl of a buffer containing 50 mM Tris-HCl (pH7.2), 10 mM MgCl$_2$, 0.1 mM DTT and 80 mM dNTP at 22° C. for 30 minutes. After ethanol precipitation, the precipitate was treated with one unit of alkaline phosphatase (bovine intestine) in 20 μl of a buffer containing 50 mM Tris-HCl (pH9.0), 1 mM MgCl$_2$, 0.1 mM ZnCl and 1 mM spermidine at 7° C. for 30 minutes. After phenol treatment, ethanol precipitation was carried out. The precipitate was dissolved in 20 μl of a solution containing 10 mM Tris-HCl (pH7.5) and 1 mM EDTA. This solution contained 0.1 μg/μl of DNA. One μg of this DNA and 1 μg of the above-mentioned DNA fragment (B) were reacted with 1.5 units of T4 DNA ligase in 20 μl of a buffer containing 66 mM Tris-HCl (pH7.6), 6.6 mM MgCl$_2$, 10 mM DTT and 1 mM ATP at 15° C. for 15 hours. The reaction mixture was used to transform *E. coli* JM103 according to a conventional procedure, and obtained ampicillin resistant transformants were screened for colonies containing plasmid pDPAT2 shown in FIG. 13, and the plasmid was isolated according to a conventional procedure.

EXAMPLE 2. CONSTRUCTION OF PLASMID pHA00

5 μg of plasmid pPE3 (same as pMUT4L) was digested with 10 units of PvuI in 50 μl of a buffer containing 10 mM Tris-HCl (pH8.0), 7 mM MgCl$_2$, 150 mM KCl and 7 mM β-mercaptoethanol at 37° C. for 5 hours. After ethanol precipitation, the precipitate was digested with 10 units of EcoRI in 50 μl of a buffer containing Tris-HCl (pH7.5), 7 mM MgCl$_2$, 100 mM NaCl and 7 mM β-mercaptoethanol at 37° C. for 2 hours. The reaction mixture was subjected to 1.2% agarose gel electrophoresis, and a DNA fragment of about 2000 bp was recovered by a conventional means. The DNA fragment thus recovered was designated as DNA fragment (A).

Next, 10 μg of plasmid pPE3 was digested with 15 units of PvuI in 50 μl of a buffer containing 10 mM Tris-HCl (pH8.0), 7 mM MgCl$_2$, 150 mM KCl and 7 mM β-mercaptoethanol at 37° C. for 5 hours. After ethanol precipitation, the precipitate was digested with 15 units of BamHI in 50 μl of a buffer containing 10 mM Tris-HCl (pH8.0), 7 mM MgCl$_2$, 100 mM NaCl and 2 mM β-mercaptoethanol at 30° C. for 3 hours. The reaction mixture was subjected to 1.2% agarose gel electrophoresis, and DNA fragments of about 2300 bp and about 1346 bp were recovered according to a conventional means. The DNA fragment of about 2300 bp thus recovered was designated as DNA fragment (B). Two μg of the DNA fragment of about 1346 bp recovered as above was digested with 5 units of BalI in 30 μl of a buffer containing 20 mM Tris-HCl (pH8.5), 7 mM MgCl$_2$ and 7 mM β-mercaptoethanol at 37° C. for 8 hours. The reaction mixture was subjected to 1.2% agarose gel electrophoresis, and DNA fragment of about 750 bp was recovered by a conventional procedure. This DNA fragment was designated as DNA fragment (C).

On the other hand, 10 μg of plasmid pDPAT2 constructed in Example 1 was digested with 15 units of EcoRI in 100 μl of a buffer containing 50 mM Tris-HCl pH7.5), 7 mM MgCl$_2$, 100 mM NaCl and 7 mM β-mercaptoethanol at 37° C. for 3 hours. The reaction mixture was subjected to 1.2% agarose gel electrophoresis, and DNA fragment of about 472 bp was recovered by a conventional procedure. 2 μg of the DNA thus recovered was digested with one unit of HaeIII in 50 μl of a buffer containing 10 mM Tris-HCl (pH7.5), 7 mM MgCl$_2$, 60 mM NaCl and 7 mM β-mercaptoethanol at 37° C. for 30 minutes. The reaction mixture was subjected to 5% polyacrylamide gel electrophoresis, and a DNA fragment of about 180 bp was recovered by a conventional procedure. One μg of this DNA fragment and 1 μg of the above-mentioned DNA fragment (C) were reacted with one unit of T4 DNA ligase in 20 μl of a buffer containing 66 mM Tris-HCl (pH7.6), 6.6 mM MgCl$_2$, 10 mM DTT and 1 mM ATP at 15° C. for 12 hours. The reaction mixture was subjected to 1.2% agarose gel electrophoresis, and a DNA fragment of about 931 bp was recovered by a conventional means. One μg of this DNA fragment, 1 μg of DNA fragment (A) and 1 μg of DNA fragment (B) were ligated with 2 units of T4 DNA ligase in 20 μl of a buffer containing 66 mM Tris-HCl (pH7.6), 6.6 mM MgCl$_2$, 10 mM DTT and 1 mM ATP at 15° C. for 12 hours. The reaction mixture was used to transform *E. coli* JM103, and resulting ampicillin resistant transformants were screened for colonies containing plasmid pHA00 shown in FIG. 14, and the plasmid was isolated by a conventional means.

EXAMPLE 3. CONSTRUCTION OF PLASMID pHA03

Figure 14:
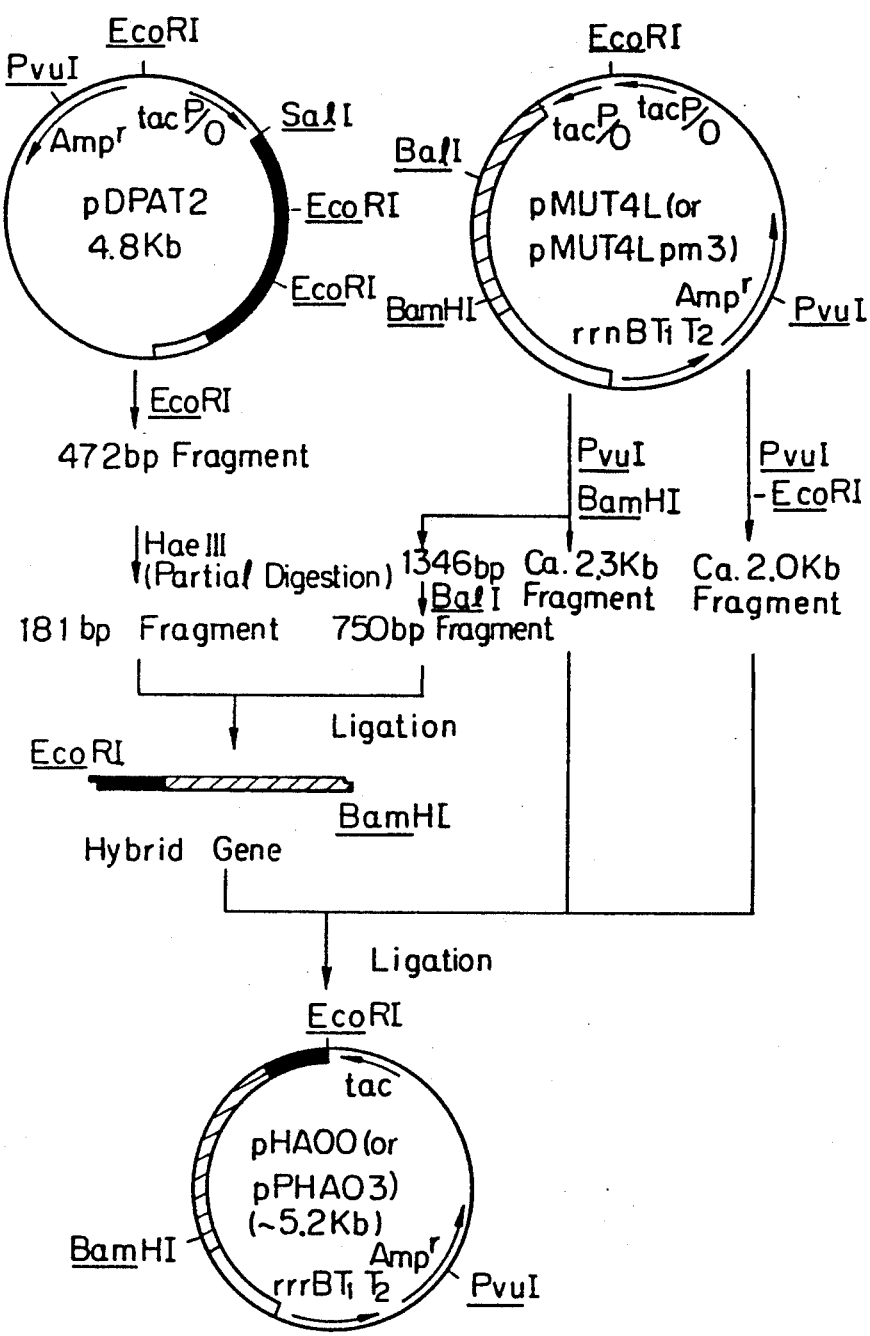
FIG. 14 represents the construction of plasmid pHA00 from plasmids pDPAT2 and pMUT4L (also designated as pPE3p), and the construction of plasmid pHAO3 from plasmids pDPAT2 and pMUT4Lpm3 (also designated as pPE3pm3)

Plasmid pHA03 was constructed according to the same procedure as described in Example 2 except that plasmid pPE3pm3 (same as pMUT4Lpm3) was used in place of plasmid pPE3 (FIG. 14).

EXAMPLE 4. CONSTRUCTION OF PLASMID pHA20

Five μg of the plasmid pHA00 constructed in Example 2 was digested with 7 units of PstI in 20 μl of a buffer containing 20 mM Tris-HCl (pH7.5), 10 mM MgCl$_2$ and 50 mM (NH4)$_2$SO$_4$ at 37° C. for 4 hours. The reaction mixture was subjected to ethanol precipitation, and the precipitate was then digested with 10 units of ScaI in 20 μl of a buffer containing 10 mM Tris-HCl (pH7.5), 7 mM MgCl$_2$, 125 mM NaCl and 7 mM β-mercaptoethanol at 37° C. for 8 hours. The reaction mixture was subjected to 1.2% agarose gel electrophoresis, and a DNA fragment of about 1100 bp was recovered by a conventional means. This DNA fragment was designated as DNA fragment (A).

Five μg of plasmid pHA00 was digested with 7 units of PstI in 20 μl of a buffer containing 20 mM Tris-HCl (pH7.6), 10 mM MgCl$_2$ and 50 mM (NH4)$_2$SO$_4$ at 37° C. for 4 hours. The reaction mixture was subjected to ethanol precipitation, and the precipitate was then digested with 10 units of EcoRI in 20 μl of a buffer containing 50 mM Tris-HCl (pH7.5), 7 mM MgCl$_2$, 100 mM NaCl and 9 mM β-mercaptoethanol at 37° C. for 3 hours. After ethanol precipitation, the precipitate was subjected to 0.7% agarose gel electrophoresis, and DNA fragment of about 3500 bp was recovered by a conventional means. This DNA fragment was designated as DNA fragment (B).

In the other hand, 15 μg of the plasmid pDPAT2 constructed in Example 1 was digested with 20 units of BglII in 100 μl of a buffer containing 10 mM Tris-HCl (pH7.5), 7 mM MgCl$_2$, 100 mM NaCl and 7 mM β-mercaptoethanol at 37° C. for 4 hours. After ethanol precipitation, the precipitate was digested with 25 units of ScaI in 100 μl of a buffer containing 10 mM Tris-HCl (pH7.5), 7 mM MgCl$_2$, 125 mM NaCl and 7 mM 8-mercaptoethanol at 37° C. for 10 hours. The reaction mixture was subjected to 1.2% agarose gel electrophoresis, and DNA fragment of about 625 bp was recovered by conventional means. This DNA fragment was designated as DNA fragment (C).

Ten μg of plasmid pDPAT2 was digested with 15 units of BglII in 100 μl of a buffer containing 10 mM Tris-HCl (pH7.5), 7 mM MgCl$_2$, 100 mM NaCl and 7 mM β-mercaptoethanol at 37° C. for 4 hours. After ethanol precipitation, the precipitate was digested with 10 units of EcoRI in 50 μl of a buffer containing 50 mM Tris-HCl (pH7.5), 7 mM MgCl$_2$, 100 mM NaCl and 7 mM β-mercaptoethanol at 37° C. for 3 hours. The reaction mixture was subjected to 5% polyacrylamide gel electrophoresis, and DNA fragment of about 150 bp was recovered according to a conventional procedure. This DNA fragment was designated as DNA fragment (D).

One μg of DNA fragment (A), 1 μg of DNA fragment (B), 1 μg of DNA fragment (C) and 1 μg of DNA fragment (D), all described above, were ligated with 4 units of T4 DNA ligase in 30 μl of a buffer containing 66 mM Tris-HCl (pH7.6), 6.6 mM $MgCl_2$, 10 mM DTT and 1 mM ATP at 15° C. for 16 hours. The reaction mixture was used to transform E. coli JM103 according to a conventional procedure, and resulting ampicillin resistant transformants were screened for colonies containing plasmid pHA20 shown in FIG. 15, and the plasmid was recovered by a conventional means.

EXAMPLE 5. CONSTRUCTION OF PLASMID pHA23

Figure 15:
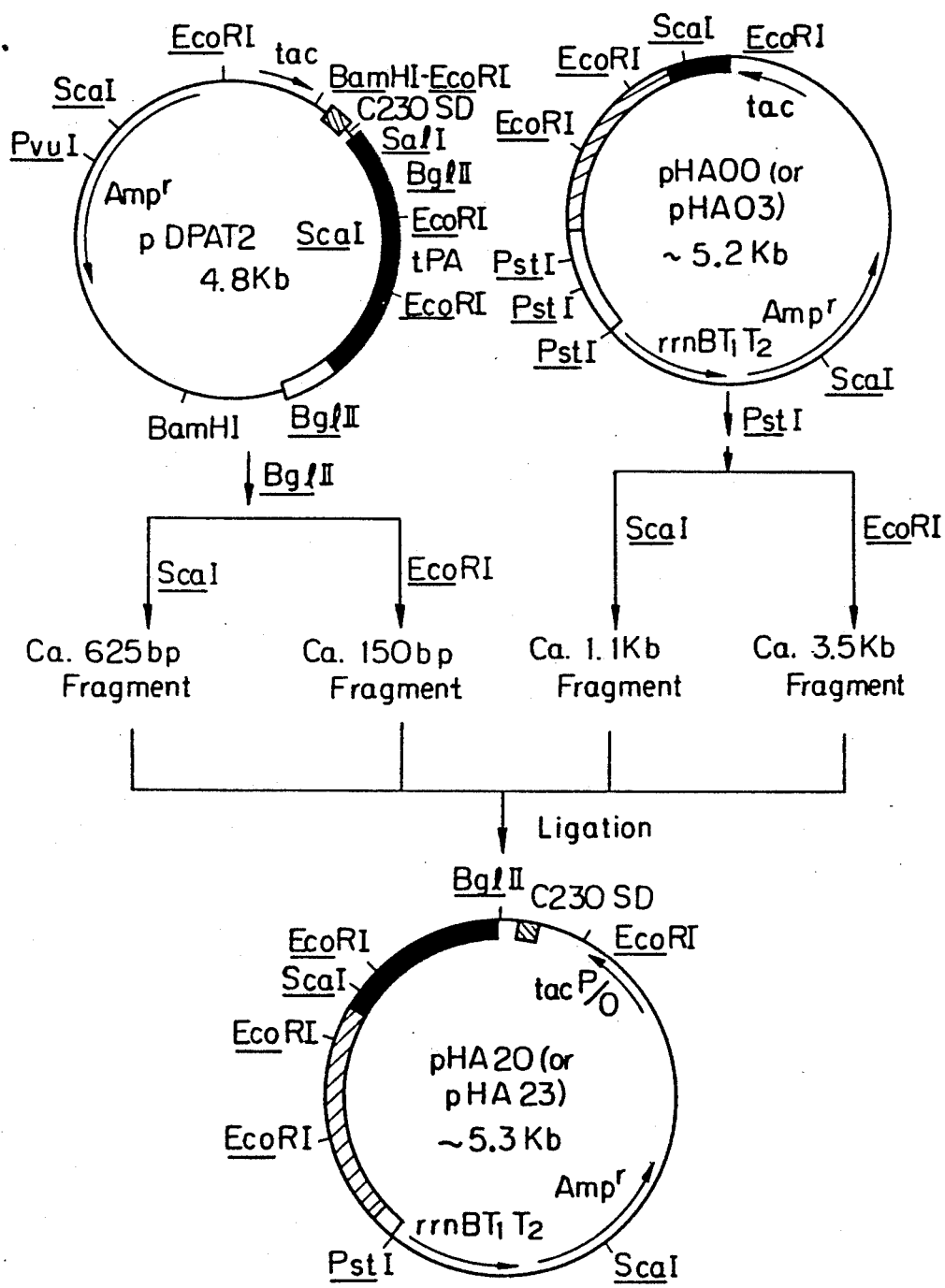
FIG. 15 represents the construction of plasmid pHA20 from plasmids pDPAT2 and pHA00, and the construction of plasmid pHA23 from plasmids pDPAT2 and pHAO3.

Plasmid pHA23 was constructed according to the same procedure as described in Example 4 except that plasmid pHA03 constructed in Example 3 was used in place of plasmid pHA00 used for construction of plasmid pHA20 (FIG. 15).

EXAMPLE 6. CONSTRUCTION OF PLASMID pHA13

Twenty-five μg of the plasmid pHA23 constructed in Example 5 was digested with 30 units of BglII in 200 μl of a buffer containing 10 mM Tris-HCl (pH7.5), 7 mM $MgCl_2$, 100 mM NaCl and 7 mM β-mercaptoethanol at 37° C. for 4 hours. After ethanol precipitation, the precipitate was treated with 4 units of Klenow fragment in 50 μl of a buffer containing 50 mM Tris-HCl (pH7.2), 10 mM $MgCl_2$, 0.1 mM DTT and 80 μM dNTP at 22° C. for 30 minutes. After phenol treatment, ethanol precipitation was carried out. The precipitate was digested with 30 units of PstI in 100 μl of a buffer containing 20 mM Tris-HCl (pH7.5), 10 mM $MgCl_2$ and 50 mM (N at 37° C. for 4 hours. The reaction mixture was subjected to 0.7% agarose gel electrophoresis, and DNA fragment of about 3500 bp designated as DNA fragment (A), and DNA fragment of about 1700 bp designated as DNA fragment (B) were recovered by a conventional means.

Seven μg of the DNA fragment (B) was digested with 10 units of RsaI in 50 μl of a buffer containing 10 mM Tris-HCl (pH8.0), 10 mM $MgCl_2$, 50 mM NaCl and 7 mM β-mercaptoethanol at 37° C. for 6 hours. The reaction mixture was subjected to 1.2% agarose gel electrophoresis, and DNA fragment of about 1100 bp designated as DNA fragment C, and DNA fragment of about 626 bp designated as DNA fragment D were recovered by a conventional means.

Figure 16:
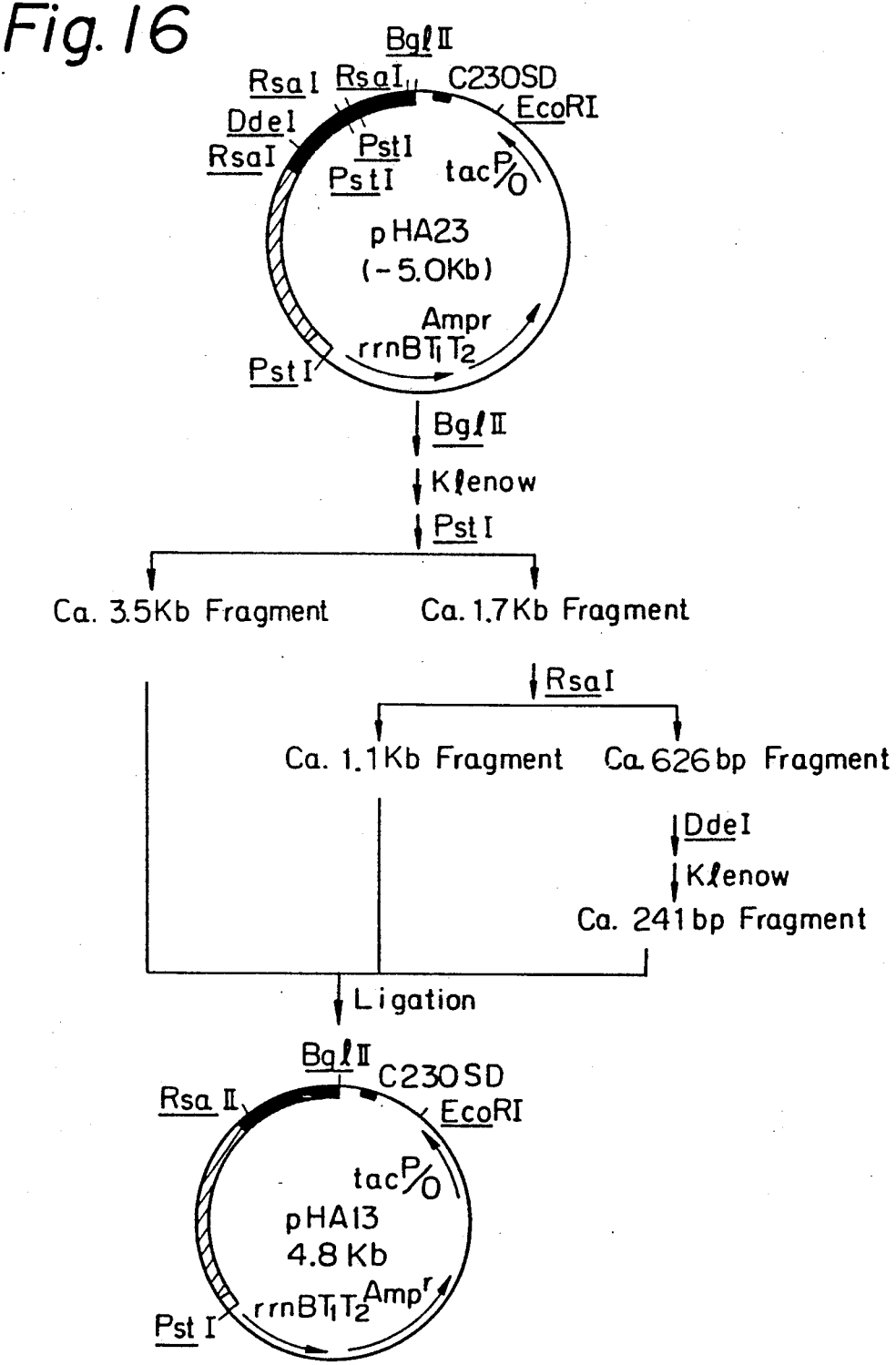
FIG. 16 represents the construction of plasmid pHA13 from plasmid pHA23.

Two μg of DNA fragment (D) was digested with 5 units of DdeI in 20 μl of a buffer containing 100 mM Tris-HCl (pH7.5), 5 mM $MgCl_2$, 100 mM NaCl and 7 mM β-mercaptoethanol at 37° C. for 8 hours. After ethanol precipitation, the precipitate was treated with one unit of Klenow fragment in 20 μl of a buffer containing 50 mM Tris-HCl (pH7.2), 10 mM $MgCl_2$, 0.1 mM DTT and 80 mM dNTP at 22° C. for 30 minutes. After phenol treatment, ethanol precipitation was carried out. The precipitate was subjected to 5% polyacrylamide gel electrophoresis, and DNA fragment of about 241 bp was recovered by a conventional procedure. One μg of this DNA fragment, 0.5 μg of DNA fragment (A), and 0.5 μg of DNA fragment (C) were ligated with 3 units of T4 DNA ligase in 20 μl of a buffer containing 66 mM Tris-HCl (pH7.6), 6.6 mM $MgCl_2$, 10 mM DTT and 1 mM ATP at 15° C. for 15 hours. The reaction mixture was used to transform E. coli JM103, and resulting ampicillin resistant transformants are screened for colonies containing plasmid pHA13 shown in FIG. 16, and the plasmid was isolated by a conventional means.

EXAMPLE 7. EXPRESSION AND EXTRACTION OF GENE PRODUCT (a) E. coli JM103/pDPAT2, JM103/pHA00, JM103/pHA03, JM103/pHA20, JM103/pHA23 and JM103/pHA13 prepared in Examples 1 to 5, and E. coli JM103/pMUTpm3 prepared in Reference Example 15 were cultured in 100 ml of LB medium supplemented with 100 μg/ml ampicillin at 37° C. with shaking. When $OD_{600}$ of the culture medium reached to 0.6, isopropyl-β,D-thiogalactopyranoside was added to the medium to 1 mM of the final concentration, and the culture was continued for additional 5 hours. The cultured broth was then transferred to an ice bath. The cooled broth was centrifuged at 3000 rpm for 10 minutes at 4° C. to collect cells, which were then suspended in 50 ml of a buffer containing 50 mM Tris-HCl (pH7.5) and 100 mM NaCl. The suspension was then centrifuged to collect cells, which were resuspended in 10 ml of the same buffer. Next, the cells were disrupted by sonication, and the disrupted cells were centrifuged at 15,000 rpm for 10 minutes at 4° C. to obtain a precipitate.

(b) Each of the precipitates prepared in step (a) was suspended in 10 ml of a buffer containing 7.5 M guanidine hydrochloride and 50 mM Tris-HCl (pH7.5), and the suspension was allowed to stand at a room temperature for 90 minutes. Next, the suspension was centrifuged at 10,000 rpm for 10 minutes, and the supernatant was diluted to 5 ml of solution containing 1 M guanidine hydrochloride, 0.05 M Tris-HCl (pH7.5), 2 mM reduced type glutathion and 0.2 mM oxidated type glutathion, and incubated overnight at a room temperature. Next, the solution was dialyzed against 100 volumes of a solution containing 10 mM Tris-HCl (pH7.4) and 0.4 M NaCl at 4° C. for 4 hours, and then 100 volumes of a solution containing 10 mM Tris-HCl (pH7.4) and 0.1 M NaCl for 2 hours to obtain an extract.

EXAMPLE 8

Each precipitate obtained from each transformant in Example 7(a), in an amount corresponding to 1 ml of cultured broth, was added with 20 μl of a sampling solution containing 3 M urea, 0.08 M dithiothreitol and 1% SDS, and the mixture was heated at 95° C. for 5 minutes. The heat-treated product was centrifuged to eliminate an insoluble matter, and 8 μl of the supernatant thus obtained was applied to an SDS-polyacrylamide gradient gel (Nature, 292 128, 1981), and electrophoresis was carried out at 50 V overnight. After the electrophoresis, the gel was stained by soaking it in a staining solution consisting of 1% Coomassie Blue, 10% acetic acid, 25% isopropanol and water for 1.5 hours, and then soaked in a destaining solution consisting of 10% acetic acid, 10% isopropanol and water for 2 hours followed by a solution consisting of 5% methanol and 7% acetic acid and water for 2 hours. An example of gel pattern thus obtained was shown in FIG. 17A. In FIG. 17A, a sample of an expression product from E. coli JM103/pHA03, which produces a hybrid plasminogen activator-like polypeptide of the present invention (HA03) (lane 2), was compared with a sample of an expression product from E. coli JM103/pPE3 (pMUT4L) (lane 1), which produces native human prourokinase (UK), and a sample of an expression product from E. coli JM103/pDPAT2, which produces native human tissue plasminogen activator (t-PA) (lane 3), by electrophoresis.

On the other hand, each sample prepared as above described was subjected to the same SDS-polyacrylamide gradient gel electrophoresis as described above, and separated proteins on the gel were then transferred to a nitrocellulose filter and the filter was subjected to an enzymeimmunoassay (EIA) (S. Tabe, *Saibo Kogaku,* Vol 2, p1061, 1983). That is, after proteins on the SDS-polyacrylamide gel were transferred to a nitrocellulose filter, to prevent non-specific adsorption, the nitrocellulose filter was soaked in a solution of 3% gelatin in TBS (20 mM Tris-HCl, pH7.5, and 500 mM NaCl), and then the filter was soaked for 2 hours in a solution containing anti-tissue plasminogen activator antiserum obtained from a rabbit immunized with tissue plasminogen activator. The filter was washed throughout with TBS solution, and then soaked in a solution containing a horseradish peroxidase-labeled anti-rabbit antibody IgG (goat) for an hour. After a thorough washing, the filter was soaked in a developing solution containing 20 mM Tris-HCl (pH7.5), 500 mM NaCl, 0.06% 4-chloro-1-naphtol and 0.015% H2O2 for 5 minutes. An example of the obtained results is shown in FIG. 17C. The same procedure as described above was applied to an anti-urokinase antiserum. An example of the obtained results is shown in FIG. 17B.

From the comparison of the patterns shown in FIGS. 17 A, B, and C, it is evident that the hybrid polypeptide of the present invention is immunoreative to both antiseum gainst tissue plasminogen activator and antiserum against urokinase.

EXAMPLE 9. PREPARATION OF FIBRIN AFFINITY SEPHAROSE COLUMN

Three g of fibrinogen (Daiichi Kagaku Yakuhin Kogyo, Japan; Type 2, plasminogen free) was dissolved in 100 ml of a linking buffer containing 0.1 M NaHCO3 (pH8.3) and 0.5 M NaCl. The solution was centrifuged to at 10000 ×g for 10 minutes eliminate insoluble materials, and the supernatant was used for subsequent reaction.

Two g of CNBr-activated Sepharose 4B (Pharmacia) was swallen with 30 ml of 1 mM HCl to obtain about 7 ml of a carrier. The carrier preparation thus obtained was loaded on a G3 glass filter, and was washed four times with 25 ml of 1 mM HCl. Moreover, the carrier was washed with 20 ml of the linking buffer and the washed carrier was suspended in 20 ml of the same buffer. Immediately after the preparation, the suspension was added to the above-mentioned fibrinogen solution, and the mixture was reacted at a room temperature for two hours with stirring. After the reaction, the supernatant was removed. The residual material was added with 50 ml of 0.2 M glycine (pH8.0) and the mixture was stirred at a room temperature for two hours to inactivate residual active groups. After removing the supernatant, the residual material was washed alternatively five times with 20 ml each of 0.2 M glycine solution (pH8.0) and an acetate buffer containing 0.1 M sodium acetate (pH5.0) and 0.5 M NaCl on a glass filter to finally obtain about 7 ml of a fibrinogen-linked carrier. This carrier was filled in a column φ16 mm ×70 mm.

Three-hundred units of bovine thrombin (Mochida Seiyaku, Japan) was dissolved in 3 ml of distilled water, and the solution was gradually run through the column, prepared as above, for two hours to convert the fibrinogen linked to the carrier to fibrin. The column was then equilibrated with 100 μl of a buffer containing 0.02 M Tris-HCl (pH7.5), 0.15 M NaCl and 0.05% Triton X-100.

EXAMPLE 10

The extract prepared in Example 7 (b), in an amount corresponding to 5 μg of the expression product, was adjusted to 100 μl of a final liquid volume containing 0.02 M Tris-HCl (pH7.5), 0.15 M NaCl and 0.05% Triton X-100. The solution thus prepared was run through the column prepared in Example 9 at a flow rate of 0.5 ml/minute allowing the reaction of the expression product in the applied solution with the fibrin linked on the carrier in the column. Subsequently, the column was washed with 40 ml of a buffer containing 0.02 M Tris-HCl (pH7.4), 0.15 M NaCl and 0.05% Triton X-100 at the above-mentioned flow rate. Next, the column was eluted with an eluting buffer containing 2 M KSCN, 0.02 M Tris-HCl (pH7.4) and 0.05% Triton X-100. During the above-mentioned washing and elution, all effluent was fractionated by 2 ml using a fraction collector. Each fraction was measured for plasminogen activator activity by fibrinolytic activity on a plasminogen-containing fibrin plate.

Fibrinolytic activity was measured as follows: A solution of 0.1 g of fibrinogen (Daiichi Kagaku Yakuhin, Japan; Fibrinogen Type 1) dissolved in 5 ml of 0.06 M phosphate buffer and a solution of 0.025 g of agarose (Sigma) dissolved in 5 ml of the same buffer was mixed. To the mixture bovine thrombin (Mochida Seiyaku, Japan) to give a final concentration of 3 NIH units/ml (1 mM), and after stirring, the mixture was poured onto a petri dish having an inner diameter of 8.5 cm to prepare a fibrin plate. Ten μl each of samples were spotted on the fibrin plate, and the plate was incubated at 37° C. for 14 hours. Diameters of developed lysis circles were measured. According to the same procedure as described above, standard samples having known units prepared from commercial urokinase of urine origin (UK) were spotted on the fibrin plate, and the plate was incubated at 37° C. for 14 hours, and the diameters of developed lysis circles were measured. From these measurements, a calibration curve of activity versus diameter of lysis circle was prepared. By applying the measurements of the lysis circle diameter of test samples to the calibration curve, the activity of the test sample was obtained.

Fractions eluted by the washing buffer which did not contain KSCN were designated as non-adsorbed fractions, while fractions eluted by the eluting buffer which contained 2 M KSCN were designated as adsorbed fractions. Elution profiles for each sample are shown in FIGS. 18-2 to 18-4. As controls, a commercially available tissue plasminogen activator (TPA), a commercially available urokinase derived from urine (UK) and recombinant TPA (DPAT2) derived from *E. coli* were treated by the same procedure as described above, and the control elution profiles are shown in FIG. 18-1.

As seen from these figures, while the commercially available urokinase (UK) is not adsorbed to a fibrin-sepharose carrier, hybrid plasminogen activator-like polypeptides of the present invention, which contain an entire or part of kringle region responsible for the affinity to fibrin of human tissue plasminogen activator, as well as a recombinant tissue plasminogen activator produced in *E. coli* and a commercially available tissue plasminogen activator, have the ability to bond to a fibrin-Sepharose carrier.

EXAMPLE 11. Km DETERMINATION USING SYNTHETIC SUBSTRATE S-2288

S-2288 (Kabi) was dissolved in a reaction buffer containing 0.1 M Tris-HCl (pH8.0), 0.01% Triton X-100 and 0.5 M NaCl, and finally, each solutions containing 0.1 mM, 0.25 mM, 0.5 mM, 0.75 mM and 1 mM S-2288 were prepared.

The extracts HA03 and HA20 prepared in Example 7(b) and a solution of commercially available urokinase (UK), each 10 µl was diluted with the reaction buffer to a final volume of 400 µl. To these samples, 2 µl of a solution of 1 mg/ml plasmin (Sigma) was added, and the reaction mixtures were allowed to stand at 37° C. for one hour in a incubator. Then, the reaction mixtures were promptly transferred to ice water, and added with 2 µl each of a solution of 5 mg/ml soybean trypsin inhibitor (Sigma) to terminate the reaction with plasmin. Five reaction mixtures were prepared for each test sample, and to each reaction mixture, the above-mentioned S-2288 solution having a different concentration was added. These reaction mixtures were allowed to stand at 37° C. for one hour in an incubator. After that, the reaction mixture were immediately transferred to an ice water bath and added with 50 µl each of 10% acetic acid solution to terminate the reaction. As a control, the same procedure as described above was carried out using 400 µl of the reaction buffer in place of the 400 µl of the test sample.

For each reaction mixture, absorbance at 405 nm was measured, and for each sample, the difference between sample absorbance and control absorbance, i.e., A value, was obtained. The reaction rate was $v = A/60$, therefore $1/v = 60/A$, wherein "60" denotes that the reaction was carried out for 60 minutes. A Lineweaver-Burk's reciprocal plot graph was formed by plotting the 1/v value on an ordinate axis and 1/S value on an abscissa axis, wherein S represents a concentration (M) of a substrate in the reaction mixture. From the graph, the Km values set forth in the following table were obtained.

TABLE

| Sample | Km measured (mol/l) | Km from Kabi S-2288 data sheet (mol/l) |
|---|---|---|
| HA03 | $2.0 \times 10^{-4}$ | |
| HA20 | $2.0 \times 10^{-4}$ | |
| Commercial UK | $2.0 \times 10^{-4}$ | $2.0 \times 10^{-4}$ |

As seen from the table, the present hybrid polypeptide HA03 consisting of a polypeptide region from 161th Met to 219th Gly corresponding to about a half of the kringle of a human tissue plasminogen activator and a polypeptide region from 150th Gln to 411th Leu of human prourokinase, wherein 157th Phe is replaced by Asp, and the present hybrid polypeptide HA20 consisting of a polypeptide region from first Ser to 219th Gly including an entire kringle region of human tissue plasminogen activator and a polypeptide region from 150th Gln to 411th Leu of human prourokinase exhibit the same Km value as commercially available urokinase.

This means that the region responsible for enzyme activity of the present hybrid polypeptide exhibits the same characteristic as the corresponding part of native urokinase, regardless of the length of the region responsible for fibrin affinity derived from the tissue plasminogen activator, and regardless of the presence or absence of point mutation in a serine protease region, i.e., at 157th amino acid.

Figure 20:
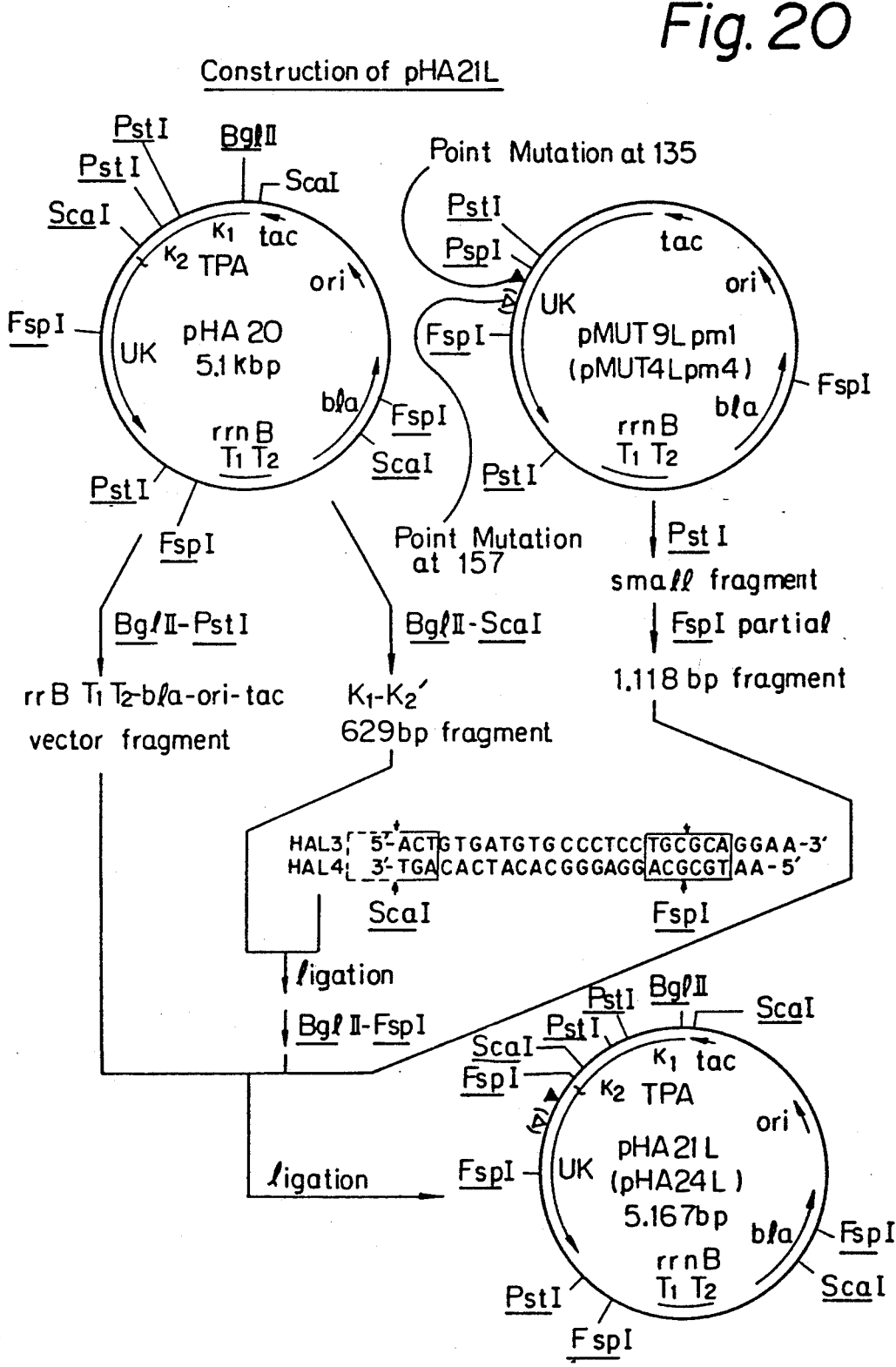
FIG. 20 represents the construction of plasmid pHA21L from plasmid pHA20 and pMUT9Lpml, and plasmid pHA24L from plasmids pHA20 and pMUT4Lpm4.

EXAMPLE 11. CONSTRUCTION OF PLASMID pHA21L (FIG. 20)

Ten µg of the plasmid pHA20 constructed in Example 4 was digested with 100 units of BqlII and 96 units of PstI in 200 µl of a buffer containing 20 mM Tris-Hcl (pH7.5), 10 mM MgCl₂ and 100 µM NaCl at 37° C. for 2 hours. The reaction mixture was subjected to 0.7% agarose gel electrophoresis, and a DNA fragment of about 3400 bp was recovered by a conventional means. This DNA fragment was designated as DNA fragment (E).

Moreover, 5 µg of the same plasmid pHA20 was digested with 100 units of BglII and 120 unit of ScaI in 200 µl of a buffer containing 10 mM Tris-Hcl (pH7.5), 7 mM Mgcl₂, 125 mM NaCl and 7 mM β-mercaptoethanol at 37° C. for 4 hours. The reaction mixture was then subjected to 0.7% agarose gel electrophoresis, and a DNA fragment of about 630 bp was recovered by a conventional means. This DNA fragemtn was designated us DNA fragment (F).

On the other hand, 5 µg of the plasmid pMUT9Lpml constructed in Reference Example 18 was digested with 30 units of PstI in 100 µl of a buffer containing 200 mM Tris-HCl (pH7.5), 10 mM MgCl₂ and 100 mM NaCl at 37° C. for 2 hours. The reaction mixture was then subjected to 0.7% ugarose gel electrophoresis, and a DNA fragment of about 1200 bp was recovered by a conventional means. This DNA fragment was partially digested with 40 unites of FspI in 100 µl of a buffer containing 10 mM Tris-HCl (pH7.4), 10 mM MgCl₂, 50 mM NaCl and 10 mM β-mercaptoethanol at 37° C. for 10 minutes. The reaction mixture was then subjected to 1.2% agarose gel electrophoresis, and a DNA fragment of about 1100 bp was recovered by a conventional means. This DNA fragemnt was designated as DNA fragement (G).

The following two oligonucleotides:

5'ACTGTGATGTGCCCTCCTGCACAGGAA 3'

3'TGACACTACACGGGAGGACGTGTCC 5' were synthesized by phospite method. 1 µg each of these syntetic oligonucleotides were mixed in 30 µl of n solution containing 50 mM Tris-HCl(pH7.6), 10 mM MgCl₂ and 10 mM β-mercaptoethanol, heated at 70° C. for 5 minutes, and then coaled on ice. The reaction mixture was added with 20 unites of T4 polynucleotide kinase, and incubated at 37° C. for one hour to phosphorylate 5'-end of the oligonucleotides. The reaction mixture was heated at 70° C. for 2 minutes and the allowed to stand at a room temperature for 5 minutes to anneal two synthetic oliganucleotides. After ethanol precipitation of the annealed product, the precipitate was mixed with the above-mentioned DNA fragment (F), and ligated by 5 units of T4 DNA ligase in 20 µl of a buffer containing 66 mM Tris-HCl (pH7.6), 6.6 mM MgCl₂, 10 mM DTT and 10 mM ATP at 12° C. for 15 hours. After phenal extraction and ethanol precipitation of the reaction mixture, the reaction mixture was digested with 10 units of FspI and 20 units of BglII in 50 µl of a buffer containing 10 mM Tris-HCl (pH7.4), 10 mM MgCl₂, 50 mM NaCl and 10 mM β-mercaptoethanol at 37° C. for 4 hours. The reaction mixture was subjected to 1.0% agarose gel electrophoresis, and DNA fragment of about 650 bp was recovered by a conventional means. This DNA fragment was designated as DNA fragment (H).

The DNA fragemtns (E), (G) and (H), all prepared as described above, were mixed, and ligated by 5 units of T4 DNA ligase in 20 μl of a buffer containing 66 mM Tris-HCl (pH7.6), 6.6 mM MgCl$_2$, 10 mM DTT and 10 mM ATP at 12° C. for 15 hours. The reaction mixture was used to transform E.coli JM103 according to a conventional means, and ampicillin resistant transformants thus obtained were screened for a colony containing plasmid pHA21L, and the plasmid pHA21L was isolated by a conventional means.

EXAMPLE 12. CONSTRUCTION OF PLASMID pHA24L

Five μg of the plasmid pMUT4Lpm4 constructed in Reference Example 17 was digested with 50 units of PstI in 100 μl of a buffer containing 20 mM Tris-HCl (pH7.5), 10 mM MgCl$_2$ and 100 mM NaCl at 37° C. for 2 hours. The reaction mixture was subjected to 0.7% agarose gel electrophoresis, and a DNA fragment of about 1200 bp was recovered by a conventional means. The DNA fragment was partially digested with 40 units of FspI in 100 μl of a buffer containing 10 mM Tris-HCl (pH7.4), 10 mM MgCl$_2$, 50 mM NaCl and 10 mM β-mercaptoethanol at 37° C. for 10 minutes. The mixture were then subjected to 1.2% agarose gel electrophoresis, and a DNA fragment of about 1100 bp was recovered by a conventional means. This DNA fragment was designated as DNA fragment (I).

On the other hand, DNA fragments (E) and (G) were prepared according to the same procedure as described in Example 11. These DNA fragments (E), (G) and (I) were mixed and ligated by T4 DNA ligase in 20 μl of a buffer containing 66 mM Tris-HCl (pH7.6), 6.6 mM MgCl$_2$, 10 mM DTT and 10 mM ATP at 12° C. for 15 hours. The reaction mixture was used to transform E.coli JM103 according to a conventional means, and ampicillin resistant transformants were screened for a colony containing plasmid pHA24L shown in FIG. 20, and the plasmid pHA24L was isolated according to a conventional means.

EXAMPLE 13. CONSTRUCTION OF PLASMID pHA11L

Five μg of the plasmid pHA21L constructed in Example 11 was digested with 50 units of ScaI and 50 units of PstI in 100 μl of a buffer containing 10 mM Tris-HCl (pH7.5), 7 mM MgCl$_2$, 125 mM NaCl and 7 mM β-mercaptoethanol at 37° C. for 6 hours. The reaction mixture was subjected to 1.0% afarose gel electrophoresis, and a DNA fragment of about 1100 bp was recovered by a conventional means. This DNA fragment was designated as DNA fragment (J).

Moreover, 10 μg of the same plasmid pHA21L was digested with 100 units of DdeI in 200 μl of a buffer containing 10 mM Tris-HCl (pH7.5), 7 mM MgCl$_2$, 150 mM NaCl and 7 mM β-mercaptoethanol at 37° C. for 15 hours. The reaction mixture was then subjected to 4.0% agarose gel electrophoresis, and a DNA fragment of about 330 bp was recovered by a conventional method. This DNA fragment was designated as DNA fragment (K).

The following two oligonucleotides:

5'ATGAAGAGGTGACGTCATGTC 3'

3'TACTTCTCCACTGCAGTACAGACT 5' were synthesized by phosphite method. 2 μg each of these two synthetic oligonucleotides were mixed, and phosphorylation of 5'-end and annealing ware carried out according to the same procedure described in Example 11. After ethanol precipitation of the annealed oligonucleotides, the precipitate was mixed with the above-prepared DNA fragment (K), and the ligation was carried out according to the same procedure as described in Example 11. After ethanol precipitation, the precipitate was digested with 100 units of ScaI and 100 units of AatII in 100 μl of a buffer containing 10 mM Tris-HCl (pH7.5), 7 mM MgCl$_2$, 125 mM NaCl and 7 mM β-mercaptoethanol at 37° C. for 15 hours. The reaction mixture was subjected to 4.0% agarose gel elecrrophoresis, and a DNA fragment of about 250 bp was reocvered by a conventional procedure. This dna fragment was designated as DNA fragment (L).

On the other hand, 5 μg of the plasmid pMUT9Lpml constructed in Reference Example 18 was digested with 50 units of AatII and 50 units of PstI in 100 μl of a buffer containing 10 mM Tris-HCl (pH7.5), 7 mM MgCl$_2$, 60 mM KCl and 7 mM β-mercaptoethanol at 37° C. for 4 hours. The reactin mixture was then subjected to 0.7% agarose gel electrophoresis, and a DNA fragment of about 3000 bp was recovered by a conventional procedure. This DNA fragment was designated as DNA fragment (M).

Figure 21:
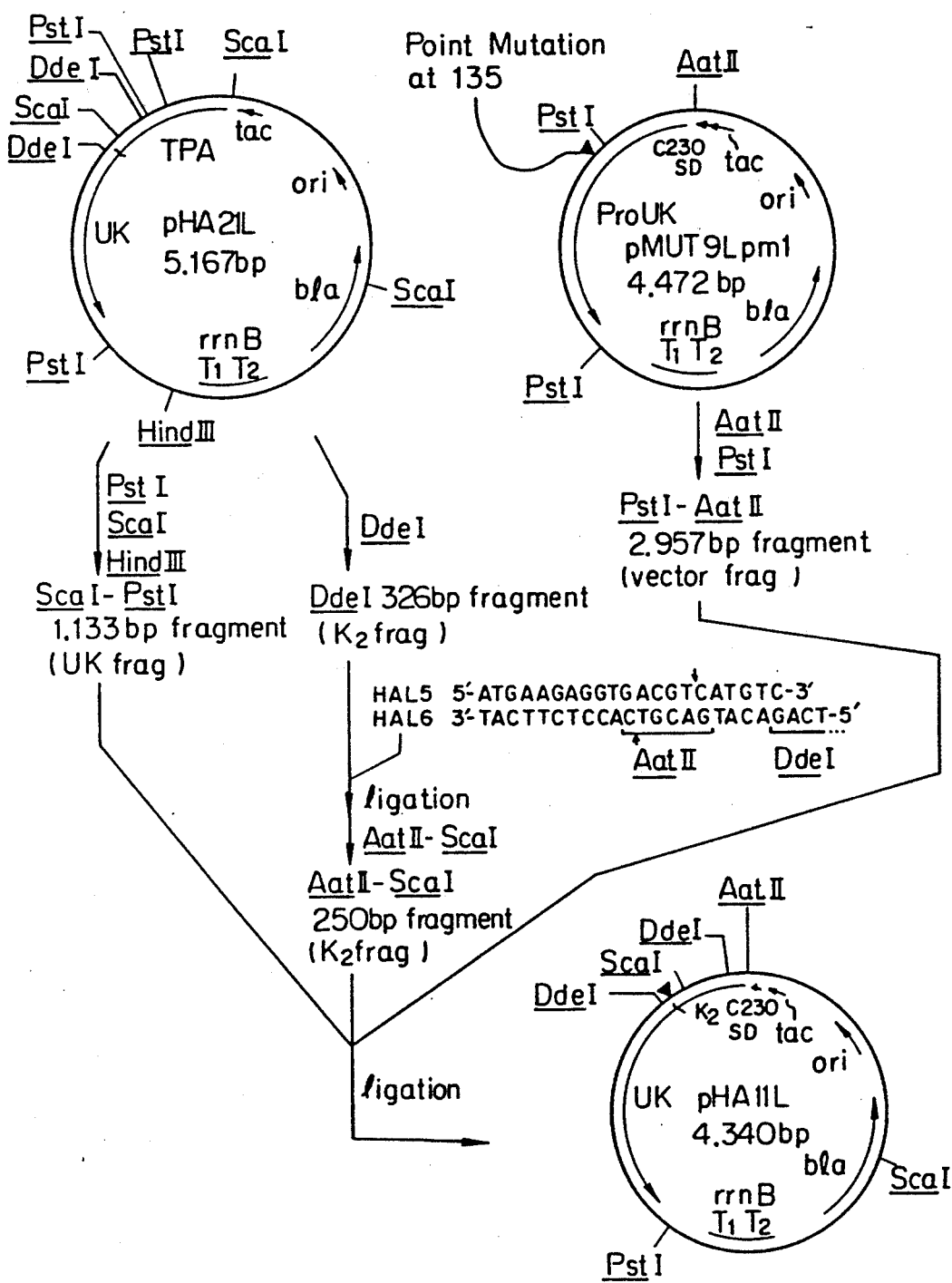
FIG. 21 represents the construction of plasmid pHA11L from plasmids pHA21L and pMUT9Lpml.

DNA fragments (J), (L) and (M), all prepared as described above, were mixed, and ligated by 5 units of T4 DNA ligase in 20 μl of a buffer containing 66 mM Tris-HCl (pH7.6), 6.6 mM MgCl$_2$, 10 M DTT and 10 mM ATP at 12° C. for 15 hours. The reaction mixture was used to transform E. coli JM103 according to a conventional procedure, and ampicillin resistant transformants were secreened for a colony containing plasmid pHA11L shown in FIG. 21, and the plasmid pHA11L was isolated according to a conventional procedure.

EXAMPLE 14. CONSTRUCTION OF PLASMID pHA14L

Five μg of the plasmid pHA24L constructed in Example 12 was digested with 50 units of ScaI and 50 units of PstI in 100 μl of abuffer containing 10 mM Tris-HCl (pH7.5), 7 mM MgCl , 125 mM NaCl and 7 mM β-mercaptoethanol at 37° C. for 6 hours. The reaction mixture was then subjected to 1.0% agarose gel electrophoresis, and a DNA fragment of about 1100 bp was recovered according to a conventional procedure. This DNA fragment was designated as DNA fragment (N).

On the other hand, DNA fragments (L) and (M) were prepared according to exactly the same procedure as decribed in Example 13. These DNA fragments (L), (M) and (N) were mixed, and ligated by 5 units of T4 DNA ligase in 20 μl of a buffer containing 66 mM Tris-HCl (pH7.6), 6.6 mM MgCl$_2$, 10 mM DTT and 10 mM ATP at 12° C. for 15 hours. The reaction mixture was used to transform E. coli JM103, and ampicillin resistant transformants were screened for a cology containing plasmid pHA14L, and the plasmid pHA14L was isolated according to a conventional procedure.

Figure 22:
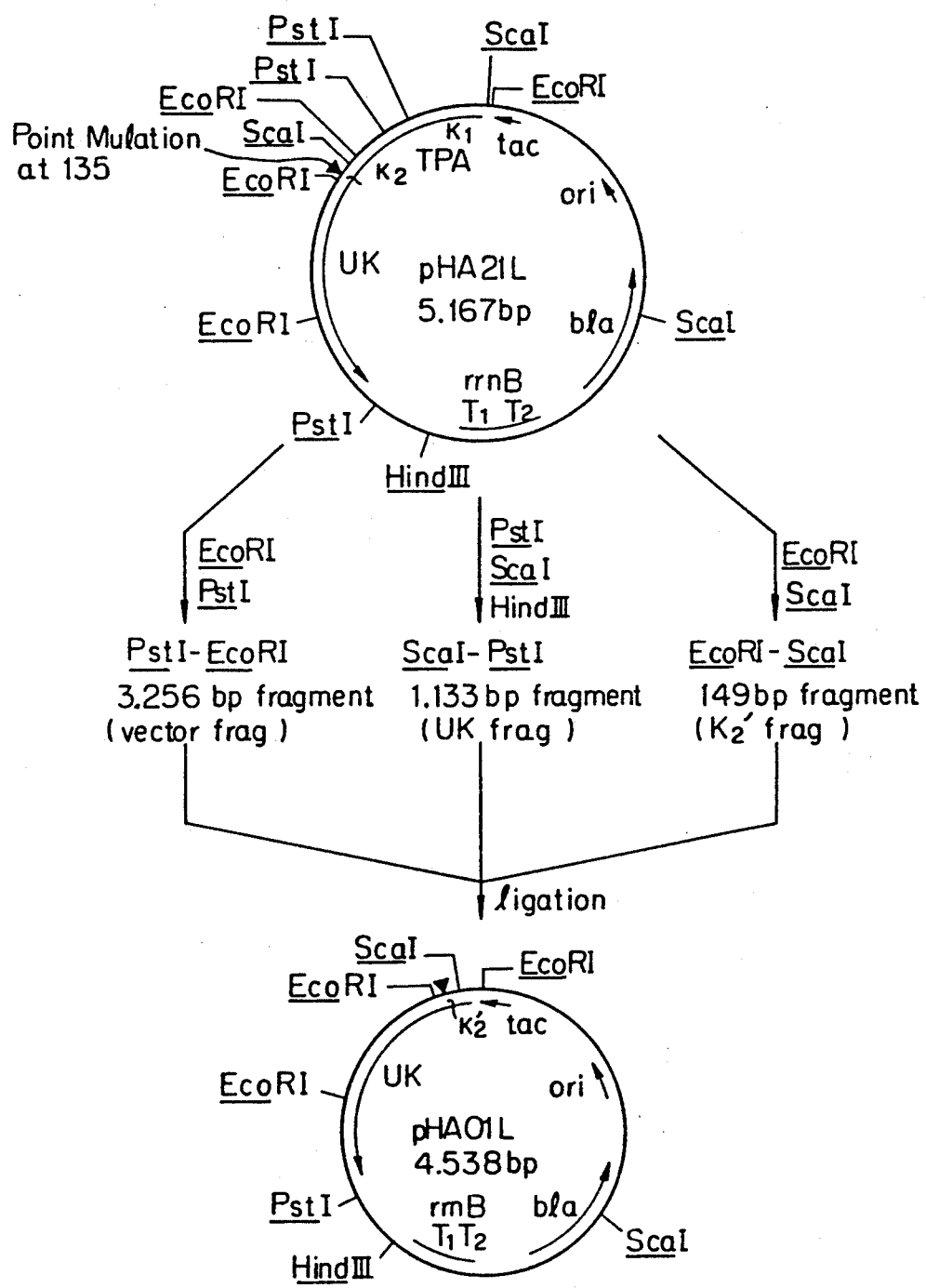
FIG. 22 represents the construction of plasmid pHA01L from plasmid pHA21L.

EXAMPLE 15. CONSTRUCTION OF PLASMID pHA01L (FIG. 22)

Five μg of the plasmid pHA21L constructed in Example 11 was digested with 50 units of EcoRI and 50 unit of PstI in 100 μl of a buffer containing 20 mM Tris-HCl (pH7.5), 10 mM MgCl₂ and 100 mM NaCl at 37° C. for 4 hours. The reaction mixture was subjected to 0.7% agarose gel electrophoresis, and a DNA fragment of about 3300 bp was recovered according to a cnventional procedure. This DNA fragment was designated as DNA fragment (O).

Five μg of the same plasmid pHA21L was digested with 50 units of ScaI and 50 units of PstI in 100 μl of a buffer containing 10 mM Tris-HCl (pH7.5), 7 mM MgCl₂, 125 mM NaCl and 7 mM β-mercaptoethanol at 37° C. for 15 hours. The reaction mixture was then subjected to 0.7% agarose gel electrophoresis, and a DNA of about 100 bp was recovered according to a conventional procedure. This DNA fragment was designated as DNA fragment (P).

Moreover, 10 μg of the same plasmid pHA21L was digested with 50 units of EcoRI and 50 units of ScaI in 100 μl of a buffer containing 10 mM Bris-HCl (pH7.5), 7 mM MgCl₂, 125 mM NaCl and 7 mM β-mercaptoethanol at 37° C. for 15 hours. The reaction mixture was then subjected to 2.0% agarose gel electrophoresis, and a DNA fragment of about 150 bp was recovered according to a conventional procedure. This DNA fragment was designated as DNA fragment (Q).

The DNA fragments (O), )P), and (Q), all prepared as described above, were mixed and ligated by 5 units of T4 DNA ligase in 20 μl of a buffer containing 66 mM Tris-HCl (pH7.6), 6.6 mM MgCl₂, 10 mM DTT and 10 mM ATP at 12° C. for 15 hours. The reaction mixture was used to transform E. coli JM103, and ampicillin resistant tranformants were screened for a colony containing plasmid pHA01 shown in FIG. 22, and the plasmid pHA01 was isolated according to a conventional procedure.

EXAMPLE 16. CONSTRUCTION OF PLASMID pHA04L

Plasmid pHA04L was constructed according to the same procedure as described in Example 15, except that the plasmid pHA24L constructed in Example 12 was used in place of the plasmid pHA21L.

EXAMPLE 17. EXPRESSION AND EXTRACTION OF HYBRID PLASMINOGEN ACTIVATOR-LIKE POLYPEPTID HPA24L

Plasmid pHA24L constructed in Example 12 was used to transform E. coli KY1436 according to a conventional procedure, and the transformant thus obtained was cultured in 5 ml of an L medium supplemented with 50 μg/ml of ampicillin in a test tube at 30° C. over night with shaking. 2 ml of the cultured broth was inoculated to 1 liter of an L medium supplemented with 50 μg/ml of ampicillin in a 5 liter conical flask, and culturing was carried out at 30° C. on an air-shaker at 250 rpm. When absorbance at 60 nm (OD₆₀₀) of the broth reached transfered to an incubator at 37° C., and culturing was carried out at 37° C. for an additional 5 hours with shaking to express a hybrid plasminogen activator-like polypeptide HPA24L gene.

Figure 23:
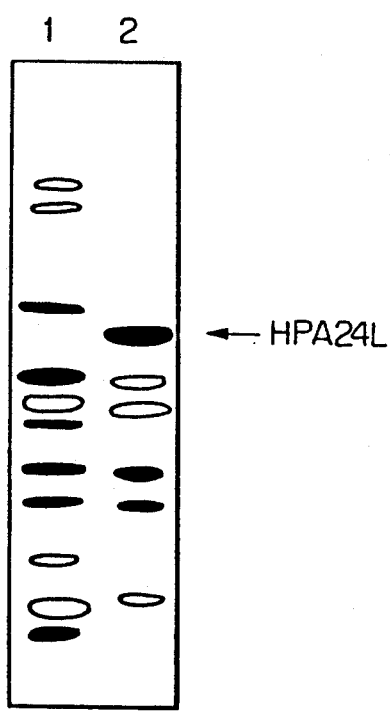
FIG. 23 represents SDS polyacrylamide gel electrophoresis for an insoluble fraction (lane 2) and supernatant (lane 1) of an expression product of plasmid pHA24L.

An amount of the cultured broth corresponding to 6 of OD₆₀₀ was transfered to plastic centrifuge tubes, and centrifuged to collect cells. The cells were suspended in 1.0 ml of a buffer containing 0.1 m NaCl and 50 mM Tris-HCl (pH8.0) and the suspension was sonicated to disrupt the cells. The sonicated suspension was then centrifuged to recover an insoluble fraction. An amount of the insoluble fraction corresponding to 1 of OD₆₀₀ was subjected to SDS-polyacrylamide gel electrophoresis according to a conventional procedure. The result is set forth in FIG. 23, wherein lane 2 represents the protein composition from the insoluble fraction and lane 1 represent that from the supenrmatant.

On the other hand, an amount of the insoluble fraction corresponding to 4 of OD₆₀₀ was suspended in 160 μl of a solution containing 6 M guanidine hydrochloride and 25 mM Tris-HCl (pH8.0), and the suspension was alllowed to stand at a room temperature for 30 minutes. The suspension was then adjusted to final concentrations of 50 mM Tris-HCl (pH8.0), 1 M guanidine hydrochloride, 2 mM reduced type glutathione, 0.2 mM oxidated type glutathione, 1 mM EDTA and 0.01% Tween 80, and allowed to stand for 15 hours at a room temperature to obtain a crude extract.

EXAMPLE 18. DETERMINATION OF ACTIVITY OF HPA24L CRUDE EXTRACT USING SYNTHETIC SUBSTRATE S-2444

Ten μl of the HPA24L crude extract prepared in Example 17 was added to a buffer containing 0.1 M Tris-HCl (pH8.0) and 0.01% Triton X-100 to make a total volume 99 μl. To the mixture 1 μl of 1 μg/μl plasmin solution was added, and the whole was incubated at 37° C. for 15 minutes, and then added with 1 μl of soybeen trypsin inhibitor solution. The mixture was completely mixed. The mixture was then added with 0.7 ml of a buffer containing 2 mM synthetic substrate X-2444, and 0.1 M Tris-CHl (pH8.0) and 0.01% Triton X-100, and the mixture was incubated at 37° C. for 30 minutes, and then 100 μl of glacial acetic acid was added to terminate the reaction.

Absorbance of the reaction mixture was measured at 405 nm. Enzyme activity in the reaction mixture was calculated according to the formula:

International Unit (I.U.) = (OD₄₀₅/0.395) × 6.5 and about 120 I.U. of the enzyme activity was obtained.

EXAMPLE 19. EXPRESSION AND EXTRACTION OF OTHER HYBLID PLASMINAGEN ACTIVATOR-LIKE POLYPEPTIDES

The same procedure as described in Examples 17 and 18 was repeated for plasmids pHA21L, pHA11L, pHA14L, pHA01L, and pHA04L, and similar results as described in Examples 17 and 18 were obtained.

LITERATURE (1) Japanese Unexamined Patent Publication No. 60-241889.
(2) Chirgwin, J.M., Przybyla, A.E., MacDonald, R.J. and Rutter, W.J. (1979) Biochemystry 18, 5294–5299.
(3) Aviv, H. and Leder, P., (1972) Proc. Natl, Acad. Sci. USA 69, 1408–1412.
(4) Okayama H. and Berg, P., (1982) Molec. Cell Biol. 2, 101–170.
(5) Norgard M.V. (1978) Gene 3, 279–292.
(6) Pennica D. (1983) Nature 301, 214—221.
(7) Denhart D. T. (1966) Biochem. Biophys. Res. Commun., 23, 643–646.
(8) A.M. Maxam, and W. Gilbert (1980) Methods Enzymol. 65, 499–560.
(9) Maniatis, T., Fritsch, E.F. and Sambrook, J. (1982) In: Molecular Cloning, Cold Spring Harbor Laboratory, Cold Spring Harbor, N.Y., pp. 254.

(10) Birnboim, H.C. and Doly, J. (1979) Nucl. Acids Res. 7, 1513–1523.
(11) Steffens, G.J., Güenzler, W.A. Öetting, F., Frankus, E. and Flohe, L. (1982) Hoppe-Seyler's Z. Physiol. Chem. 363, 1043–1058.
(12) Güenzler, W.A., supra, (1982) 1055.
(13) Grunstein M. and Hogness D.S., (1975) Proc. Natl. Acad. Sci., USA, 72, 3961–3965.
(114) Mesing, J., Grec, R. and Seeburg, P.H. (1981) Nucl. Acids Res. 9, 309–321.
(15) Agarwall, K.L., Brunstedt, J. and Noyes, B.E. (1981) J. Biol. Chem. 256, 1023–1028.
(16) Stewart A.G., Richards H., Roberts S., Marwick J., Edwards K., I. Bell, J. Smith and R. Derbyshire (1983) Nuc. Acids Res. 11, 6597–6609.
(17) Brousius J., Ullrich A., Raker M.A., Grey A., Dull T.J., Gutell R.R. and Noller H.F., (1981) plasmid 6, 112–118.
(18) Brousius, J. (1984) Gene 27, 151–160.
(19) Brousius, J. (1984) Gene 27, 161–172.
(20) Messing J., (1983) Methods in Enzymlogy, 101, 20–78.
(21) Benton W.D. and Davis R.W. (1977), Science 916, 180–182.

We claim:
1. The hybrid polypeptide HA20.
2. The hybrid polypeptide HA23.
3. The hybrid polypeptide HA13.
4. The hybrid polypeptide HPA21L.
5. The hybrid polypeptide HPA24L.

* * * * *